US011306077B2

(12) United States Patent
Craig, II et al.

(10) Patent No.: US 11,306,077 B2
(45) Date of Patent: Apr. 19, 2022

(54) COMPOUNDS, COMPOSITIONS AND METHODS

(71) Applicant: Denali Therapeutics Inc., South San Francisco, CA (US)

(72) Inventors: Robert A. Craig, II, South San Francisco, CA (US); Javier de Vicente Fidalgo, Foster City, CA (US); Anthony A. Estrada, Danville, CA (US); Jianwen A. Feng, San Mateo, CA (US); Brian M. Fox, Redwood City, CA (US); Maksim Osipov, Redwood City, CA (US); Arun Thottumkara, San Francisco, CA (US)

(73) Assignee: Denali Therapeutics Inc., South San Francisco, CA (US)

( * ) Notice: Subject to any disclaimer, the term of this patent is extended or adjusted under 35 U.S.C. 154(b) by 0 days.

(21) Appl. No.: 17/334,587

(22) Filed: May 28, 2021

(65) Prior Publication Data

US 2021/0292311 A1   Sep. 23, 2021

Related U.S. Application Data

(63) Continuation of application No. PCT/US2020/018007, filed on Feb. 12, 2020.

(60) Provisional application No. 62/877,232, filed on Jul. 22, 2019, provisional application No. 62/805,263, filed on Feb. 13, 2019.

(51) Int. Cl.
| | |
|---|---|
| *C07D 413/04* | (2006.01) |
| *C07D 271/113* | (2006.01) |
| *C07D 413/14* | (2006.01) |
| *C07D 417/04* | (2006.01) |
| *C07D 417/14* | (2006.01) |
| *C07D 493/08* | (2006.01) |

(52) U.S. Cl.
CPC ........ *C07D 413/04* (2013.01); *C07D 271/113* (2013.01); *C07D 413/14* (2013.01); *C07D 417/04* (2013.01); *C07D 417/14* (2013.01); *C07D 493/08* (2013.01)

(58) Field of Classification Search
CPC .. C07D 413/14; C07D 417/14; C07D 413/04; C07D 417/04; C07D 493/08; C07D 271/113
USPC ....................................................... 514/249
See application file for complete search history.

(56) References Cited

U.S. PATENT DOCUMENTS

| | | | |
|---|---|---|---|
| 7,053,104 B2 | 5/2006 | Van Wagenen et al. | |
| 8,193,179 B2 | 6/2012 | Hubschwerlen et al. | |
| 9,408,392 B2 | 8/2016 | O'Sullivan et al. | |
| 9,421,211 B2 | 8/2016 | Aktas et al. | |
| 9,447,025 B2 | 9/2016 | Bunker | |
| 9,693,975 B2 | 7/2017 | Bunker | |
| 9,708,247 B2 | 7/2017 | Walter et al. | |
| 10,343,981 B2 | 7/2019 | Walter et al. | |
| 2001/0047100 A1 | 11/2001 | Kjaersgaard et al. | |
| 2003/0149089 A1 | 8/2003 | Heerding et al. | |
| 2008/0221100 A1 | 9/2008 | Gless et al. | |
| 2009/0131444 A1 | 5/2009 | Reck et al. | |
| 2013/0225644 A1 | 8/2013 | Larsen et al. | |
| 2013/0324551 A1 | 12/2013 | Pulici et al. | |
| 2014/0121196 A1 | 5/2014 | Sugimoto et al. | |
| 2015/0259344 A1 | 9/2015 | Iwata et al. | |
| 2016/0075654 A1 | 3/2016 | Bunker et al. | |
| 2017/0100400 A1 | 4/2017 | Charifson et al. | |
| 2017/0183355 A1 | 6/2017 | Sprott et al. | |
| 2017/0342020 A1 | 11/2017 | Walter et al. | |
| 2017/0369486 A1 | 12/2017 | Acharya et al. | |
| 2020/0331900 A1 | 10/2020 | Craig, II et al. | |
| 2021/0130308 A1 | 5/2021 | Craig, II et al. | |
| 2021/0147435 A1 | 5/2021 | Craig, II et al. | |

FOREIGN PATENT DOCUMENTS

| | | |
|---|---|---|
| WO | WO-0023076 | 4/2000 |
| WO | WO-02080928 | 10/2002 |
| WO | WO-2004058730 | 7/2004 |
| WO | WO-2006028904 | 3/2006 |
| WO | WO-2010067332 | 6/2010 |
| WO | WO-2012088365 | 6/2012 |
| WO | WO-2012145569 | 10/2012 |
| WO | WO-2014144952 | 9/2014 |
| WO | WO-2015038778 | 3/2015 |
| WO | WO-2016044331 | 3/2016 |
| WO | WO-2016138288 | 9/2016 |
| WO | WO-2016169911 | 10/2016 |
| WO | WO-2016177658 | 11/2016 |
| WO | WO-2017059965 | 4/2017 |
| WO | WO-2017193030 | 11/2017 |
| WO | WO-2017193034 | 11/2017 |
| WO | WO-2017193041 | 11/2017 |
| WO | WO-2017193063 | 11/2017 |
| WO | WO-2017212423 | 12/2017 |
| WO | WO-2017212425 | 12/2017 |

(Continued)

OTHER PUBLICATIONS

Extended European Search Report for European Application No. 18844666.0 dated Mar. 26, 2021. 10 pages.

(Continued)

*Primary Examiner* — Kahsay Habte

(74) *Attorney, Agent, or Firm* — Sheppard Mullin Richter & Hampton LLP

(57) ABSTRACT

The present disclosure relates generally to eukaryotic initiation factor 2B modulators, or a pharmaceutically acceptable salt, stereoisomer, mixture of stereoisomers, or prodrug thereof, and methods of making and using thereof.

47 Claims, No Drawings

(56) References Cited

FOREIGN PATENT DOCUMENTS

| WO | WO-2018009615 | 1/2018 |
|---|---|---|
| WO | WO-2018107072 | 6/2018 |
| WO | WO-2018225093 | 12/2018 |
| WO | WO-2019008506 | 1/2019 |
| WO | WO-2019008507 | 1/2019 |
| WO | WO-2019032743 | 2/2019 |
| WO | WO-2019046779 | 3/2019 |
| WO | WO-2019090069 | 5/2019 |
| WO | WO-2019090074 | 5/2019 |
| WO | WO-2019090076 | 5/2019 |
| WO | WO-2019090078 | 5/2019 |
| WO | WO-2019090081 | 5/2019 |
| WO | WO-2019090082 | 5/2019 |
| WO | WO-2019090085 | 5/2019 |
| WO | WO-2019090088 | 5/2019 |
| WO | WO-2019090090 | 5/2019 |
| WO | WO-2019118785 | 6/2019 |
| WO | WO-2019183589 | 9/2019 |
| WO | WO-2019193540 | 10/2019 |
| WO | WO-2019193541 | 10/2019 |
| WO | WO-2020012339 | 1/2020 |
| WO | WO-2020031107 | 2/2020 |
| WO | WO-2020077217 | 4/2020 |
| WO | WO-2020167994 | 8/2020 |
| WO | WO-2020168011 | 8/2020 |
| WO | WO-2020181247 | 9/2020 |
| WO | WO-2020223536 | 11/2020 |
| WO | WO-2020223538 | 11/2020 |

OTHER PUBLICATIONS

Extended European Search Report for European Application No. 18850713.1 dated Mar. 30, 2021. 6 pages.
Hearn et al., Structure-Activity Studies of Bis-O-Arylglycolamides: Inhibitors of the Integrated Stress Response. ChemMedChem 2016, vol. 11, pp. 870-880.
International Search Report and Written Opinion for International Application No. PCT/US2018/045868 dated Nov. 26, 2018. 9 pages.
International Search Report and Written Opinion for International Application No. PCT/US2018/049197 dated Feb. 5, 2019. 12 pages.
International Search Report and Written Opinion for International Application No. PCT/US2019/023739 dated Jul. 11, 2019. 16 pages.
International Search Report and Written Opinion for International Application No. PCT/US2020/017985 dated Apr. 23, 2020. 15 pages.
International Search Report and Written Opinion for International Application No. PCT/US2020/018007 dated Apr. 21, 2020. 11 pages.
International Search Report and Written Opinion for International Application No. PCT/US2020/021534 dated May 1, 2020. 15 pages.
Joshi et al., Small molecule modulators of eukaryotic initiation factor 2a kinases, the key regulators of protein synthesis. Biochimie 2013, vol. 95, pp. 1980-1990, XP028731042.
Kashiwagi et al., Crystal structure of eukaryotic translation initiation factor 2B. Nature 2016, vol. 531, pp. 122-125.
Kim et al., Therapeutic modulation of elF2a phosphorylation rescues TDP-43 toxicity in amyotrophic lateral sclerosis disease models. Nature Genetics 2014, vol. 46, No. 2, pp. 152-160.
PubChem CID 13756165, 3,4-dihydro-2H-chromen-2-yl-(4-phenylpiperidin-1-yl)methanone, Feb. 8, 2007, 7 pages, retrieved from the internet: pubchem.ncbi.nlm.nih.gov/compound/13756165 on Sep. 17, 2020.
PubChem CID 65333682, 4-[2-(oxan-3-yl)-1,3-thiazol-4-yl]benzonitrile, Oct. 23, 2012, 8 pages, retrieved from the internet: pubchem.ncbi.nlm.nih.gov/compound/65333682 on Sep. 17, 2020.
PubChem CID 68023613, N-[5-Methoxy-6-(methoxymethyl)oxan-3-yl]heptanamide, Nov. 30, 2012, 12 pages, retrieved from the internet: pubchem.ncbi.nlm.nih.gov/compound/68023613 on Oct. 16, 2018.
PubChem CID 68310749, [(2S,5R)-5-Aminooxan-2-yl]-morpholin-4-ylmethanone, Nov. 30, 2012, 10 pages, retrieved from the internet: pubchem.ncbi.nlm.nih.gov/compound/68310749 on Sep. 17, 2020.
PubChem CID 79039022, N-[(4-hydroxyoxan-4-yl)methyl]-3-phenoxypropanamide, Oct. 19, 2014, 8 pages, retrieved from the internet: pubchem.ncbi.nlm.nih.gov/compound/79039022 on Sep. 17, 2020.
PubChem CID 828546, N-Cyclohexyl-1,2,3,4-tetrahydroisoquinoline-2-carboxamide, Jul. 9, 2005, 10 pages, retrieved from the internet: pubchem.ncbi.nlm.nih.gov/compound/828546#section=BioAssay-Results on Sep. 17, 2020.
PubChem CID 91786719, N-[(3R,4S)-4-(2-amino-2-oxoethoxy)oxan-3-yl]-4-phenoxybutanamide, Jun. 3, 2015, 9 pages, retrieved from the internet: pubchem.ncbi.nlm.nih.gov/compound/91786719 on Sep. 17, 2020.
RN 1449697-58-8, registry database compound, (2013). 1 page.
Sekine et al., Mutations in a translation initiation factor identify the target of a memory-enhancing compound. Science 2015, vol. 348, issue 6238, pp. 1027-1030.
Sidrauski et al., Pharmacological brake-release of mRNA translation enhances cognitive memory. eLife 2013;2:e00498 doi: 10.7554/eLife.00498. 22 pages.
Sidrauski et al., Pharmacological dimerization and activation of the exchange factor elF2B antagonizes the integrated stress response. eLife 2015;4:e07314, doi: 10.7554/eLife.07314. 27 pages.
Chemical Abstracts Registry No. 1135218-61-9, indexed in the Registry file on STN CAS Online Apr. 16, 2009. (Year: 2009).
Registry Database Compounds, 2021, listing of registry database compounds for RN 1398569-33-9 and RN 132587-45-2. 17 pages.

COMPOUNDS, COMPOSITIONS AND METHODS

CROSS REFERENCE TO RELATED APPLICATIONS

This application is a continuation application under 35 U.S.C. § 111(a) of the International Application No. PCT/US2020/018007, filed Feb. 12, 2020, which application claims the benefit under 35 U.S.C. § 119(e) to U.S. Provisional Application Numbers 62/805,263, filed Feb. 13, 2019 and 62/877,232, filed Jul. 22, 2019, all of which are incorporated herein by reference in their entireties.

FIELD

The present disclosure relates generally to small molecule modulators of eukaryotic initiation factor 2B and their use as therapeutic agents, for example, in treating diseases mediated thereby such as Alzheimer's, Parkinson's, ALS, frontotemporal dementia, and cancer.

BACKGROUND

Neurodegenerative diseases, such as Parkinson's disease (PD), amyotrophic lateral sclerosis (ALS), Alzheimer's disease (AD), and Frontotemporal dementia (FTD) have a negative effect on the lives of millions of people.

The multi-subunit protein complexes eukaryotic initiation factor 2B and eukaryotic initiation factor 2 are required for protein synthesis initiation and regulation in eukaryotic cells. Eukaryotic initiation factor 2B is composed of five subunits (α, β, γ, δ, and ε), and eukaryotic initiation factor 2 is composed of three subunits (α, β, and γ). Eukaryotic initiation factor 2B functions as a guanine nucleotide exchange factor (GEF) that catalyzes the exchange of guanosine-5'-diphosphate (GDP) with guanosine-5'-triphosphate (GTP) on eukaryotic initiation factor 2, thereby allowing the GTP bound eukaryotic initiation factor 2 to bind to the initiating methionine transfer RNA and initiate protein synthesis.

Eukaryotic initiation factor 2B is active when complexed as a ten subunit dimer. Eukaryotic initiation factor 2 is active when bound to GTP and inactive when bound to GDP. Moreover, when the a subunit of eukaryotic initiation factor 2 is phosphorylated on serine 51, it inhibits and regulates the guanine nucleotide exchange activity of eukaryotic initiation factor 2B. In its phosphorylated form, eukaryotic initiation factor 2 remains in an inactive GDP bound state and translation initiation is blocked.

The interaction between eukaryotic initiation factor 2B and eukaryotic initiation factor 2 plays an important role in the integrated stress response (ISR) pathway. Activation of this pathway leads in part to ATF4 (Activating Transcription Factor 4) expression and stress granule formation. Aberrant ISR activation is found in multiple neurodegenerative diseases, with a strong functional link to pathology characterized by the RNA-binding/stress-granule protein TAR DNA binding protein (TARDBP), also known as TDP43. Activation of eIF2B inhibits the ISR and ISR dependent stress granule formation and is found to be neuroprotective in multiple disease models.

Impairment of eukaryotic initiation factor 2B activity is correlated to activation of the ISR pathway that is implicated in a variety neurodegenerative diseases including Parkinson's disease, amyotrophic lateral sclerosis (ALS), Alzheimer's disease, and frontotemporal dementia. Mutations in TDP43 and other RNA-binding proteins/stress-granule proteins alter stress-granule dynamics and cause ALS. Inhibition of the ISR pathway can block and promote the dissolution of stress-granules. In addition, mutations in the human eukaryotic initiation factor 2B subunits have been identified as causing leukoencephalopathy with vanishing white matter (VWM) and childhood ataxia with central nervous system hypomyelination (CACH). In VWM/CACH patients, white matter lesions severely deteriorate and neurological disorders are exacerbated after stresses, and their eukaryotic initiation factor 2B guanine nucleotide exchange activities are generally lower than normal.

DESCRIPTION

Provided herein are compounds, or a pharmaceutically acceptable salt, isotopically enriched analog, stereoisomer, mixture of stereoisomers, or prodrug of the compounds, that are useful in treating and/or preventing diseases mediated, at least in part, by eukaryotic initiation factor 2B, such as neurodegenerative diseases (e.g., neurodegeneration in prion disease) and cancer.

In some embodiments, provided are compounds that modulate the activity of eukaryotic initiation factor 2B. In some embodiments, the compounds modulate the regulation of eukaryotic initiation factor 2B. In some aspects, the compounds modulate the inhibition of eukaryotic initiation factor 2B by phosphorylated eukaryotic initiation factor 2. In some embodiments, the compounds interfere with the interaction between eukaryotic initiation factor 2B and phosphorylated eukaryotic initiation factor 2. In some embodiments, the phosphorylated eukaryotic initiation factor 2 is phosphorylated on its alpha subunit (eukaryotic initiation factor 2α phosphate).

In some embodiments, provided are compounds that act as activators of eukaryotic initiation factor 2B by increasing its guanosine diphosphate/guanosine triphosphate (GDP/GTP) nucleotide exchange activity. In some embodiments, the compounds promote eukaryotic initiation factor 2B dimer formation. In other embodiments, the compounds enhances the guanine nucleotide exchange factor (GEF) activity of eukaryotic initiation factor 2B. In other embodiments, the compounds increases the guanine nucleotide exchange factor (GEF) activity of eukaryotic initiation factor 2B on its eukaryotic initiation factor 2/GDP substrate.

In some embodiments, provided are compounds that desensitizes cells to the deleterious effects of eukaryotic initiation factor 2B inhibition. In some embodiments the deleterious effects include ATF4 expression and stress granule formation.

In another embodiment, provided is a pharmaceutical composition comprising a compound as described herein, or a pharmaceutically acceptable salt, isotopically enriched analog, stereoisomer, mixture of stereoisomers, or prodrug thereof, and a pharmaceutically acceptable carrier.

In another embodiment, provided is a method for treating a disease or condition mediated, at least in part, by eukaryotic initiation factor 2B, the method comprising administering an effective amount of the pharmaceutical composition comprising a compound as described herein, or a pharmaceutically acceptable salt, isotopically enriched analog, stereoisomer, mixture of stereoisomers, or prodrug thereof.

In another embodiment, provided is a method for treating a disease or condition mediated, at least in part, by regulation of eukaryotic initiation factor 2B, the method comprising administering an effective amount of the pharmaceutical composition comprising a compound as described herein, or a pharmaceutically acceptable salt, isotopically enriched analog, stereoisomer, mixture of stereoisomers, or prodrug thereof, and a pharmaceutically acceptable carrier, to a subject in need thereof.

In another embodiment, provided is a method for promoting or stabilizing eukaryotic initiation factor 2B dimer formation, the method comprising administering an effective amount of the pharmaceutical composition comprising a compound as described herein, or a pharmaceutically acceptable salt, isotopically enriched analog, stereoisomer, mixture of stereoisomers, or prodrug thereof, and a pharmaceutically acceptable carrier, to a subject in need thereof.

In another embodiment, provided is a method for promoting eukaryotic initiation factor 2B activity, the method comprising administering an effective amount of the pharmaceutical composition comprising a compound as described herein, or a pharmaceutically acceptable salt, isotopically enriched analog, stereoisomer, mixture of stereoisomers, or prodrug thereof, and a pharmaceutically acceptable carrier, to a subject in need thereof.

In another embodiment, provided is a method for desensitizing cells to eukaryotic initiation factor 2 phosphorylation, the method comprising administering an effective amount of the pharmaceutical composition comprising a compound as described herein, or a pharmaceutically acceptable salt, isotopically enriched analog, stereoisomer, mixture of stereoisomers, or prodrug thereof, and a pharmaceutically acceptable carrier, to a subject in need thereof.

In another embodiment, provided is a method for inhibiting the integrated stress response pathway, the method comprising administering an effective amount of the pharmaceutical composition comprising a compound as described herein, or a pharmaceutically acceptable salt, isotopically enriched analog, stereoisomer, mixture of stereoisomers, or prodrug thereof, and a pharmaceutically acceptable carrier, to a subject in need thereof.

In another embodiment, provided is a method for inhibiting stress granule formation, the method comprising administering an effective amount of the pharmaceutical composition comprising a compound as described herein, or a pharmaceutically acceptable salt, isotopically enriched analog, stereoisomer, mixture of stereoisomers, or prodrug thereof, and a pharmaceutically acceptable carrier, to a subject in need thereof.

In another embodiment, provided is a method for inhibiting ATF4 expression, the method comprising administering an effective amount of the pharmaceutical composition comprising a compound as described herein, or a pharmaceutically acceptable salt, isotopically enriched analog, stereoisomer, mixture of stereoisomers, or prodrug thereof, and a pharmaceutically acceptable carrier, to a subject in need thereof.

In another embodiment, provided is a method for inhibiting ATF4 translation, the method comprising administering an effective amount of the pharmaceutical composition comprising a compound as described herein, or a pharmaceutically acceptable salt, isotopically enriched analog, stereoisomer, mixture of stereoisomers, or prodrug thereof, and a pharmaceutically acceptable carrier, to a subject in need thereof.

The disclosure also provides compositions, including pharmaceutical compositions, kits that include the compounds, and methods of using (or administering) and making the compounds. The disclosure further provides compounds or compositions thereof for use in a method of treating a disease, disorder, or condition that is mediated, at least in part, by eukaryotic initiation factor 2B. Moreover, the disclosure provides uses of the compounds or compositions thereof in the manufacture of a medicament for the treatment of a disease, disorder, or condition that is mediated, at least in part, by eukaryotic initiation factor 2B.

DETAILED DESCRIPTION

The following description sets forth exemplary embodiments of the present technology. It should be recognized, however, that such description is not intended as a limitation on the scope of the present disclosure but is instead provided as a description of exemplary embodiments.

1. Definitions

As used in the present specification, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl) or 1 to 4 carbon atoms (i.e., $C_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$), and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having a triple bond and a double bond, such as one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy, and 1,2-dimethylbutoxy.

"Alkylthio" refers to the group "alkyl-S—". "Alkylsulfinyl" refers to the group "alkyl-S(O)—". "Alkylsulfonyl" refers to the group "alkyl-S(O)$_2$—". "Alkylsulfonylalkyl" refers to -alkyl-S(O)$_2$-alkyl.

"Acyl" refers to a group —C(O)R$^y$, wherein R$^y$ is hydrogen, alkyl, alkenyl, alkynyl, cycloalkyl, heterocyclyl, aryl, heteroalkyl, or heteroaryl; each of which may be optionally substituted, as defined herein. Examples of acyl include, e.g., formyl, acetyl, cyclohexylcarbonyl, cyclohexylmethylcarbonyl, and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein, or R$^y$ and R$^z$ are taken together to form a cycloalkyl or heterocyclyl; each of which may be optionally substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Aminoalkyl" refers to the group "-alkyl-NR$^y$R$^z$," wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Amidino" refers to —C(NR$^y$)(NR$^z$$_2$), wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include, e.g., phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Arylalkyl" or "Aralkyl" refers to the group "aryl-alkyl-".

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Carboxyl ester" or "ester" refer to both —OC(O)R$^x$ and —C(O)OR$^x$, wherein R$^x$ is alkyl, alkenyl, alkynyl, cycloalkyl, heterocyclyl, aryl, heteroalkyl, or heteroaryl; each of which may be optionally substituted, as defined herein.

"Cyanoalkyl" refers to refers to an alkyl group as defined above, wherein one or more (e.g., 1 or 2) hydrogen atoms are replaced by a cyano (—CN) group.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond) and carbocyclic fused ring systems having at least one sp$^3$ carbon atom (i.e., at least one non-aromatic ring). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Monocyclic groups include, for example, cyclopropyl, cyclobutyl, cyclopentyl, cyclohexyl, cycloheptyl, and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl, and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Cycloalkoxy" refers to "—O-cycloalkyl."

"Cycloalkylalkyl" refers to the group "cycloalkyl-alkyl-".

"Cycloalkylalkoxy" refers to "—O-alkyl-cycloalkyl."

"Guanidino" refers to —NR$^y$C(=NR$^z$)(NR$^y$R$^z$), wherein each R$^y$ and R$^z$ are independently hydrogen, alkyl, alkenyl, alkynyl, cycloalkyl, heterocyclyl, aryl, heteroalkyl, or heteroaryl; each of which may be optionally substituted, as defined herein.

"Hydrazino" refers to —NHNH$_2$.

"Imino" refers to a group —C(NR$^y$)R$^z$, wherein R$^y$ and R$^z$ are each independently hydrogen, alkyl, alkenyl, alkynyl, cycloalkyl, heterocyclyl, aryl, heteroalkyl, or heteroaryl; each of which may be optionally substituted, as defined herein.

"Imido" refers to a group —C(O)NR$^y$C(O)R$^z$, wherein R$^y$ and R$^z$ are each independently hydrogen, alkyl, alkenyl, alkynyl, cycloalkyl, heterocyclyl, aryl, heteroalkyl, or heteroaryl; each of which may be optionally substituted, as defined herein.

"Halogen" or "halo" refers to atoms occupying group VIIA of the periodic table, such as fluoro, chloro, bromo, or iodo.

"Haloalkyl" refers to an unbranched or branched alkyl group as defined above, wherein one or more (e.g., 1 to 6 or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Haloalkoxy" refers to an alkoxy group as defined above, wherein one or more (e.g., 1 to 6 or 1 to 3) hydrogen atoms are replaced by a halogen.

"Hydroxyalkyl" refers to an alkyl group as defined above, wherein one or more (e.g., 1 to 6 or 1 to 3) hydrogen atoms are replaced by a hydroxy group.

"Heteroalkyl" refers to an alkyl group in which one or more of the carbon atoms (and any associated hydrogen atoms) are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocyclyl, aryl, heteroalkyl, or heteroaryl; each of which may be optionally substituted, as defined herein. Examples of heteroalkyl groups include, e.g., ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.), and amines (e.g., —CH$_2$NR$^y$CH$_3$, —CH(CH$_3$)NR$^y$CH$_3$, —CH$_2$CH$_2$NR$^y$CH$_3$, —CH$_2$CH$_2$NR$^y$CH$_2$CH$_2$NR$^y$CH$_3$, etc., where R$^y$ is independently hydrogen, alkyl, alkenyl, alkynyl, cycloalkyl, heterocyclyl, aryl, heteroalkyl, or heteroaryl; each of which may be optionally substituted, as defined herein). As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroalkylene" refers to a divalent alkyl group (i.e., alkylene) in which one or more (e.g., one to five or one to three) of the carbon atoms (and any associated hydrogen atoms) are each independently replaced with the same or different heteroatomic group, provided that when L is heteroalkylene then the point of attachment of the heteroalkylene to the pyran is through a carbon atom. "Heteroalkylene" groups must have at least one carbon and at least one heteroatomic group within the chain. Further to when L is heteroalkylene, the point of attachment of the heteroalkylene to —R$^2$ may be through a carbon atom or a heteroatom. The term "heteroalkylene" includes unbranched or branched saturated chain having carbon and heteroatoms. By way of example, 1, 2, or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocyclyl, aryl, heteroalkyl, or heteroaryl; each of which may be optionally substituted, as defined herein. Examples of heteroalkylene groups include, e.g., —CH$_2$OCH$_2$—, —CH(CH$_3$)OCH$_2$—, —CH$_2$CH$_2$OCH$_2$—, —CH$_2$CH$_2$OCH$_2$CH$_2$OCH$_2$—, —CH$_2$SCH$_2$—, —CH(CH$_3$)SCH$_2$—, —CH$_2$CH$_2$SCH$_2$—, —CH$_2$CH$_2$SCH$_2$CH$_2$SCH$_2$—, —CH$_2$S(O)$_2$CH$_2$—, —CH(CH$_3$)S(O)$_2$CH$_2$—, —CH$_2$CH$_2$S(O)$_2$CH$_2$—, —CH$_2$CH$_2$S(O)$_2$CH$_2$CH$_2$OCH$_2$—, —CH$_2$NR$^y$CH$_2$—, —CH(CH$_3$)NR$^y$CH$_2$—, —CH$_2$CH$_2$NR$^y$CH$_2$—, —CH$_2$CH$_2$NR$^y$CH$_2$CH$_2$NR$^y$CH$_2$—, etc., where R$^y$ is hydrogen, alkyl, alkenyl, alkynyl, cycloalkyl, heterocyclyl, aryl, heteroalkyl, or heteroaryl; each of which may be optionally substituted, as defined herein). As used herein, heteroalkylene includes 1 to 10 carbon atoms, 1 to 8 carbon atoms, or 1 to 4 carbon atoms; and 1 to 3 heteroatoms, 1 to 2 heteroatoms, or 1 heteroatom. As used herein, the term "heteroalkylene" does not include groups such as amides or other functional groups having an oxo present on one or more carbon atoms.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, imidazolyl, indazolyl, indolyl, isoindolyl, isoquinolyl, isoxazolyl, isothiazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, thiazolyl, thiadiazolyl, triazolyl, tetrazolyl, and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heteroarylalkyl" refers to the group "heteroaryl-alkyl-".

"Heterocyclyl" refers to a saturated or partially unsaturated cyclic alkyl group, with one or more ring heteroatoms independently selected from nitrogen, oxygen, and sulfur. The term "heterocyclyl" includes heterocycloalkenyl groups (i.e., the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro, and may comprise one or more (e.g., 1 to 3) oxo (=O) or N-oxide (—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring carbon atoms (i.e., C$_{2-20}$ heterocyclyl), 2 to 12 ring carbon atoms (i.e., C$_{2-12}$ heterocyclyl), 2 to 10 ring carbon atoms (i.e., C$_{2-10}$ heterocyclyl), 2 to 8 ring carbon atoms (i.e., C$_{2-8}$ heterocyclyl), 3 to 12 ring carbon atoms (i.e., $C_{3-12}$ heterocyclyl), 3 to 8 ring carbon atoms (i.e., $C_{3-8}$ heterocyclyl), or 3 to 6 ring carbon atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur, or oxygen. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), thiomorpholinyl, thiamorpholinyl, 1-oxo-thiomorpholinyl, and 1,1-dioxothiomorpholinyl. The term "heterocyclyl" also includes "spiroheterocyclyl" when there are two positions for substitution on the same carbon atom. Examples of the spiroheterocyclyl rings include, e.g., bicyclic and tricyclic ring systems, such as oxabicyclo[2.2.2]octanyl, 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system.

"Heterocyclylalkyl" refers to the group "heterocyclylalkyl-."

"Oxime" refers to the group —$CR^y$(=NOH) wherein $R^y$ is hydrogen, alkyl, alkenyl, alkynyl, cycloalkyl, heterocyclyl, aryl, heteroalkyl, or heteroaryl; each of which may be optionally substituted, as defined herein.

"Sulfonyl" refers to the group —$S(O)_2R^y$, where $R^y$ is hydrogen, alkyl, alkenyl, alkynyl, cycloalkyl, heterocyclyl, aryl, heteroalkyl, or heteroaryl; each of which may be optionally substituted, as defined herein. Examples of sulfonyl are methylsulfonyl, ethylsulfonyl, phenylsulfonyl, and toluenesulfonyl.

"Sulfinyl" refers to the group —$S(O)R^y$, where $R^y$ is hydrogen, alkyl, alkenyl, alkynyl, cycloalkyl, heterocyclyl, aryl, heteroalkyl, or heteroaryl; each of which may be optionally substituted, as defined herein. Examples of sulfinyl are methylsulfinyl, ethylsulfinyl, phenylsulfinyl, and toluenesulfinyl.

"Sulfonamido" refers to the groups —$SO_2NR^yR^z$ and —$NR^ySO_2R^z$, where $R^y$ and $R^z$ are each independently hydrogen, alkyl, alkenyl, alkynyl, cycloalkyl, heterocyclyl, aryl, heteroalkyl, or heteroaryl; each of which may be optionally substituted, as defined herein.

Certain commonly used alternative chemical names may be used. For example, a divalent group such as a divalent "alkyl" group, a divalent "aryl" group, a divalent heteroaryl group, etc., may also be referred to as an "alkylene" group or an "alkylenyl" group (for example, methylenyl, ethylenyl, and propylenyl), an "arylene" group or an "arylenyl" group (for example, phenylenyl or napthylenyl, or quinolinyl for heteroarylene), respectively. Also, unless indicated explicitly otherwise, where combinations of groups are referred to herein as one moiety, e.g., arylalkyl or aralkyl, the last mentioned group contains the atom by which the moiety is attached to the rest of the molecule.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5 or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one (e.g., 1 to 5 or 1 to 3) hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, —$NHNH_2$, =$NNH_2$, imino, imido, hydroxy, oxo, oxime, nitro, sulfonyl, sulfinyl, alkylsulfonyl, alkylsulfinyl, thiocyanate, —$S(O)OH$, —$S(O)_2OH$, sulfonamido, thiol, thioxo, N-oxide, or —$Si(R^y)_3$, wherein each $R^y$ is independently hydrogen, alkyl, alkenyl, alkynyl, heteroalkyl, cycloalkyl, aryl, heteroaryl, or heterocyclyl.

In certain embodiments, "substituted" includes any of the above alkyl, alkenyl, alkynyl, cycloalkyl, heterocyclyl, aryl, or heteroaryl groups in which one or more (e.g., 1 to 5 or 1 to 3) hydrogen atoms are independently replaced with deuterium, halo, cyano, nitro, azido, oxo, alkyl, alkenyl, alkynyl, haloalkyl, cycloalkyl, heterocyclyl, aryl, heteroaryl, —$NR^gR^h$, —$NR^gC(=O)R^h$, —$NR^gC(=O)NR^gR^h$, —$NR^gC(=O)OR^h$, —$NR^gS(=O)_{1-2}R^h$, —$C(=O)R^g$, —$C(=O)OR^g$, —$OC(=O)OR^g$, —$OC(=O)R^g$, —$C(=O)NR^gR^h$, -$OC(=O)NR^gR^h$, —$OR^g$, —$SR^g$, —$S(=O)R^g$, —$S(=O)_2R^g$, —$OS(=O)_{1-2}R^g$, —$S(=O)_{1-2}R^g$, —$NR^gS(=O)_{1-2}NR^gR^h$, =$NSO_2R^g$, =$NOR^g$, —$S(=O)_{1-2}NR^gR^h$, —$SF_5$, —$SCF_3$, or —$OCF_3$. In certain embodiments, "substituted" also means any of the above groups in which one or more (e.g., 1 to 5 or 1 to 3) hydrogen atoms are replaced with —$C(=O)R^g$, —$C(=O)OR^g$, —$C(=O)NR^gR^h$, —$CH_2SO_2R^g$, or —$CH_2SO_2NR^gR^h$. In the foregoing, $R^g$ and $R^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. In certain embodiments, "substituted" also means any of the above groups in which one or more (e.g., 1 to 5 or 1 to 3) hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl, or two of $R^g$ and $R^h$ and $R^i$ are taken together with the atoms to which they are attached to form a heterocyclyl ring optionally substituted with oxo, halo, or alkyl optionally substituted with oxo, halo, amino, hydroxyl, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)

substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein, is also intended to represent unlabeled forms as well as isotopically labeled forms of the compounds. These forms of compounds may also be referred to as "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Various isotopically labeled compounds of the present disclosure, for example those into which radioactive isotopes such as $^3$H and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life, reduced dosage requirements, and/or an improvement in therapeutic index. An $^{18}$F, $^3$H, $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino, and/or carboxyl groups, or groups similar thereto.

Provided are also or a pharmaceutically acceptable salt, isotopically enriched analog, deuterated analog, stereoisomer, mixture of stereoisomers, and prodrugs of the compounds described herein. "Pharmaceutically acceptable" or "physiologically acceptable" refer to compounds, salts, compositions, dosage forms, and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids, and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic or organic acids. Salts derived from inorganic acids include, e.g., hydrochloric acid, hydrobromic acid, sulfuric acid, nitric acid, phosphoric acid, and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic or organic bases. Salts derived from inorganic bases include, by way of example only, sodium, potassium, lithium, aluminum, ammonium, calcium, and magnesium salts. Salts derived from organic bases include, but are not limited to, salts of primary, secondary, and tertiary amines, such as alkyl amines (i.e., NH$_2$(alkyl)), dialkyl amines (i.e., HN(alkyl)$_2$), trialkyl amines (i.e., N(alkyl)$_3$), substituted alkyl amines (i.e., NH$_2$(substituted alkyl)), di(substituted alkyl) amines (i.e., HN(substituted alkyl)$_2$), tri(substituted alkyl) amines (i.e., N(substituted alkyl)$_3$), alkenyl amines (i.e., NH$_2$(alkenyl)), dialkenyl amines (i.e., HN(alkenyl)$_2$), trialkenyl amines (i.e., N(alkenyl)$_3$), substituted alkenyl amines (i.e., NH$_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., NH$_2$(cycloalkyl), HN(cycloalkyl)$_2$, N(cycloalkyl)$_3$), mono-, di- or tri-arylamines (i.e., NH$_2$(aryl), HN(aryl)$_2$, N(aryl)$_3$), or mixed amines, etc. Specific examples of suitable amines include, by way of example only, isopropylamine, trimethyl amine, diethyl amine, tri (iso-propyl) amine, tri(n-propyl) amine, ethanolamine, 2-dimethylaminoethanol, piperazine, piperidine, morpholine, N-ethylpiperidine, and the like.

The term "hydrate" refers to the complex formed by the combining of a compound described herein and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid, and ethanolamine.

Some of the compounds disclosed herein may exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Some of the compounds disclosed herein, or their pharmaceutically acceptable salts, may include an asymmetric center and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and/or fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present disclosure contemplates various stereoisomers, or mixtures thereof, and includes "enantiomers," which refers to two stereoisomers whose molecules are nonsuperimposeable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds described herein, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

2. Compounds

Provided herein are compounds that are modulators of eukaryotic initiation factor 2B. In certain embodiments, provided is a compound of Formula I:

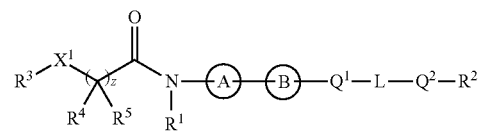

or a pharmaceutically acceptable salt, isotopically enriched analog, stereoisomer, mixture of stereoisomers, or prodrug thereof, wherein:

ring A is cycloalkyl or heterocyclyl, provided ring A is not a bicyclo[1.1.1]pentane or bicyclo[2.1.1]hexane; wherein each is optionally substituted with one to six $R^{14}$;

ring B is a 5- or 6-membered heteroaryl or phenyl; wherein each is optionally substituted with one to three $R^{13}$;

$Q^1$ and $Q^2$ are each independently O, S or $NR^{15}$;

L is a $C_{1-6}$ alkylene linker, optionally substituted with one to three substituents independently selected from halo, cyano, nitro, —$OR^6$, —$SR^6$, —$SF_5$, —$NR^6R^7$, $C_{1-6}$ alkyl, $C_{2-6}$ alkenyl, $C_{2-6}$ alkynyl, —$C(O)R^6$, —$C(O)OR^6$, —OC(O)$OR^6$, —OC(O)$R^6$, —C(O)$NR^6R^7$, —OC(O)$NR^6R^7$, —$NR^6C(O)NR^7R^8$, —$S(O)_{1-2}R^6$, —$S(O)_{1-2}NR^6$, —$NR^6S(O)_{1-2}R^7$, —$NR^6S(O)_{1-2}NR^7R^8$, —$NR^6C(O)R^7$, and —$NR^6C(O)OR^7$;

z is 0 or 1;

$X^1$ is O, $NR^9$ or a bond;

$R^1$ is hydrogen, $C_{1-12}$ alkyl, $C_{2-12}$ alkenyl, $C_{2-12}$ alkynyl, $C_{3-10}$ cycloalkyl, or heterocyclyl, each of which, other than hydrogen, is optionally substituted with one to three $R^{11}$;

$R^2$ is $C_{1-6}$ haloalkyl;

$R^3$ is hydrogen, $C_{1-12}$ alkyl, $C_{2-12}$ alkenyl, $C_{2-12}$ alkynyl, $C_{3-10}$ cycloalkyl, heterocyclyl, aryl, or heteroaryl, each of which, other than hydrogen, is optionally substituted with one to five $R^{11}$;

$R^4$ and $R^5$ are independently hydrogen, $C_{1-12}$ alkyl, $C_{2-12}$ alkenyl or $C_{2-12}$ alkynyl, each of which, other than hydrogen, is independently optionally substituted with one to five $R^1$;

or $R^3$ and $R^4$, together with the atoms to which they are attached, join to form a $C_{3-10}$ cycloalkyl or heterocyclyl, each of which is optionally substituted with one to five $R^{11}$;

or $R^4$ and $R^5$, together with the atoms to which they are attached, join to form a $C_{3-10}$ cycloalkyl or heterocyclyl, each of which is optionally substituted with one to five $R^{11}$;

each of $R^6$, $R^7$, and $R^8$ is independently hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —C(O)R$^{20}$, —C(O)OR$^{20}$, —C(O)NR$^{20}$R$^{21}$, —S(O)$_{1-2}$R$^{20}$ or —S(O)$_{1-2}$NR$^{20}$, wherein each alkyl, alkenyl, alkynyl, cycloalkyl, heterocyclyl, aryl, and heteroaryl of $R^6$, $R^7$, and R is independently optionally substituted with one to five $R^{12}$; or two of $R^6$, $R^7$, and $R^8$ are taken together with the atoms to which they are attached to form heterocyclyl independently optionally substituted by one to three halo, oxo, or $C_{1-12}$ alkyl independently optionally substituted by one to three oxo, halo, hydroxyl, or amino;

$R^9$ is hydrogen, $C_{1-12}$ alkyl, $C_{2-12}$ alkenyl, $C_{2-12}$ alkynyl, $C_{3-10}$ cycloalkyl, or heterocyclyl, each of which, other than hydrogen, is optionally substituted with one to three $R^{11}$;

each $R^{11}$ is independently halo, cyano, nitro, oxo, —OR$^6$, —SR$^6$, —SF$_5$, —NR$^6$R$^7$, $C_{1-2}$ alkyl, $C_{2-12}$ alkenyl, $C_{2-12}$ alkynyl, $C_{3-10}$ cycloalkyl, heterocyclyl, aryl, heteroaryl, —C(O)R$^6$, —C(O)OR$^6$, —OC(O)OR$^6$, —OC(O)R$^6$, —C(O)NR$^6$R$^7$, —OC(O)NR$^6$R$^7$, —NR$^6$C(O)NR$^7$R$^8$, —S(O)$_{1-2}$R$^6$, —S(O)$_{1-2}$NR$^6$, —NR$^6$S(O)$_{1-2}$R$^7$, —NR$^6$S(O)$_{1-2}$NR$^7$R$^8$, —NR$^6$C(O)R$^7$, or —NR$^6$C(O)OR$^7$, wherein each alkyl, alkenyl, alkynyl, cycloalkyl, heterocyclyl, aryl, and heteroaryl of $R^{11}$ is independently optionally substituted with one to five $R^{12}$;

each $R^{12}$ is independently halo, cyano, nitro, oxo, —OR$^{30}$, —SR$^{30}$, —SF$_5$, —NR$^{30}$R$^{31}$, $C_{1-12}$ alkyl, $C_{2-12}$ alkenyl, $C_{2-12}$ alkynyl, $C_{3-10}$ cycloalkyl, heterocyclyl, aryl, heteroaryl, —C(O)R$^{30}$, —C(O)OR$^{30}$, —OC(O)OR$^{30}$, —OC(O)R$^{30}$, —C(O)NR$^{30}$R$^{31}$, —OC(O)NR$^{30}$R$^{31}$, —NR$^{30}$C(O)NR$^{30}$R$^{31}$, —S(O)$_{1-2}$R$^{30}$, —S(O)$_{1-2}$NR$^{30}$, —NR$^{30}$S(O)$_{1-2}$R$^{31}$, —NR$^{30}$S(O)$_{1-2}$NR$^{30}$R$^{31}$, —NR$^{30}$C(O)R$^{31}$, or —NR$^{30}$C(=O)OR$^{31}$, wherein each alkyl, alkenyl, alkynyl, cycloalkyl, heterocyclyl, aryl, and heteroaryl of $R^2$ is independently optionally substituted with one to three halo or $C_{1-12}$ alkyl independently optionally substituted by one to three oxo, halo, hydroxyl, or amino;

each $R^{13}$ is independently halo, cyano, nitro, oxo, —OR$^{30}$, —SR$^{30}$, —SF$_5$, —NR$^{30}$R$^{31}$, $C_{1-12}$ alkyl, $C_{2-12}$ alkenyl, $C_{2-12}$ alkynyl, $C_{3-10}$ cycloalkyl, heterocyclyl, aryl, heteroaryl, —C(O)R$^{30}$, —C(O)OR$^{30}$, —OC(O)OR$^{30}$, —OC(O)R$^{30}$, —C(O)NR$^{30}$R$^{31}$, —OC(O)NR$^{30}$R$^{31}$, —NR$^{30}$C(O)NR$^{30}$R$^{31}$, —S(O)$_{1-2}$R$^{30}$, —S(O)$_{1-2}$NR$^{30}$, —NR$^{30}$S(O)$_{1-2}$R$^{31}$, —NR$^{30}$S(O)$_{1-2}$NR$^{30}$R$^{31}$, —NR$^{30}$C(O)R$^{31}$, or —NR$^{30}$C(=O)OR$^{31}$, wherein each alkyl, alkenyl, alkynyl, cycloalkyl, heterocyclyl, aryl, and heteroaryl of $R^{13}$ is independently optionally substituted with one to three halo or $C_{1-12}$ alkyl independently optionally substituted by one to three oxo, halo, hydroxyl, or amino;

each $R^{14}$ is independently halo, cyano, —NR$^6$R$^7$, $C_{1-6}$ alkyl, $C_{1-6}$ alkoxy, or $C_{1-6}$ haloalkyl, or two $R^{14}$ together with the atoms to which they are attached form a ring or a C=O;

each $R^{15}$ is independently hydrogen, $C_{1-6}$ alkyl, or $C_{1-6}$ haloalkyl;

each $R^{20}$ and $R^{21}$ is independently hydrogen or $C_{1-12}$ alkyl independently optionally substituted with one to three oxo, halo, hydroxyl, or amino; or $R^{20}$ and $R^{21}$ are taken together with the atoms to which they are attached to form heterocyclyl independently optionally substituted by one to three halo or $C_{1-12}$ alkyl independently optionally substituted by one to three oxo, halo, hydroxyl, or amino; and each $R^{30}$ and $R^{31}$ is independently hydrogen or $C_{1-12}$ alkyl independently optionally substituted with one to three oxo, halo, hydroxyl, or amino; or $R^{30}$ and $R^{31}$ are taken together with the atoms to which they are attached to form heterocyclyl independently optionally substituted by one to three halo or $C_{1-12}$ alkyl independently optionally substituted by one to three oxo, halo, hydroxyl, or amino.

In certain embodiments, ring A is $C_{3-10}$ cycloalkyl or heterocyclyl, provided ring A is not a bicyclo[1.1.1]pentane or bicyclo[2.1.1]hexane; wherein each is optionally substituted with one to six $R^{14}$.

In certain embodiments, ring A is monocyclic cycloalkyl, fused bicyclic cycloalkyl, or spiro bicyclic cycloalkyl, wherein each is optionally substituted with one to six $R^{14}$. In certain embodiments, ring A is monocyclic $C_{3-8}$ cycloalkyl, fused bicyclic $C_{4-10}$ cycloalkyl, or spiro $C_{4-10}$ bicyclic cycloalkyl, wherein each is optionally substituted with one to six $R^{14}$.

In the embodiments disclosed herein, ring A is not optionally substituted bicyclo[1.1.1]pentane or optionally substituted bicyclo[2.1.1]hexane, where the terms "bicyclo[1.1.1]pentane" and "bicyclo[2.1.1]hexane" are represented by

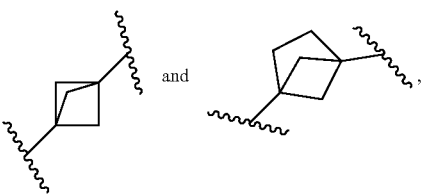 [SMILES: *C12CC(*)(C1)C2 ; *C12CCC(*)(C1)C2]

respectively.

In certain embodiments, ring A is heterocyclyl, wherein each is optionally substituted with one to six $R^{14}$.

In certain embodiments, each $R^{14}$ is independently halo, cyano, —NR$^6$R$^7$, $C_{1-6}$ alkyl, or $C_{1-6}$ haloalkyl.

In certain embodiments, ring A is selected from:

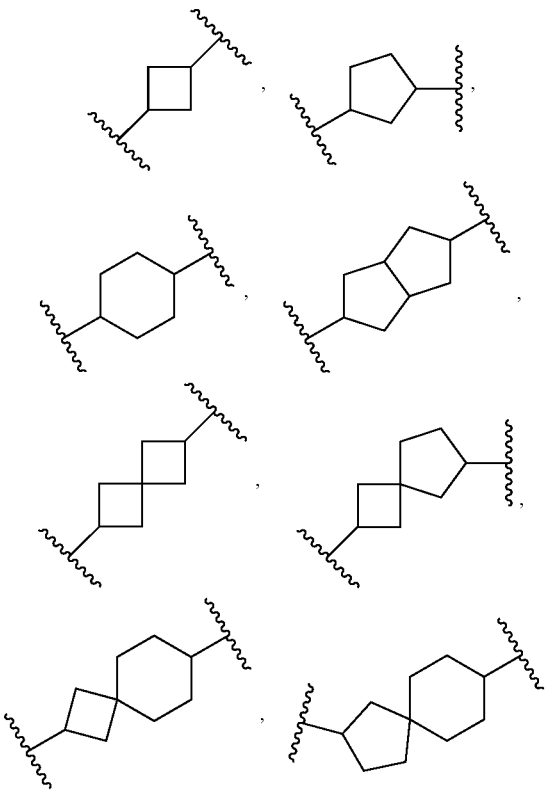

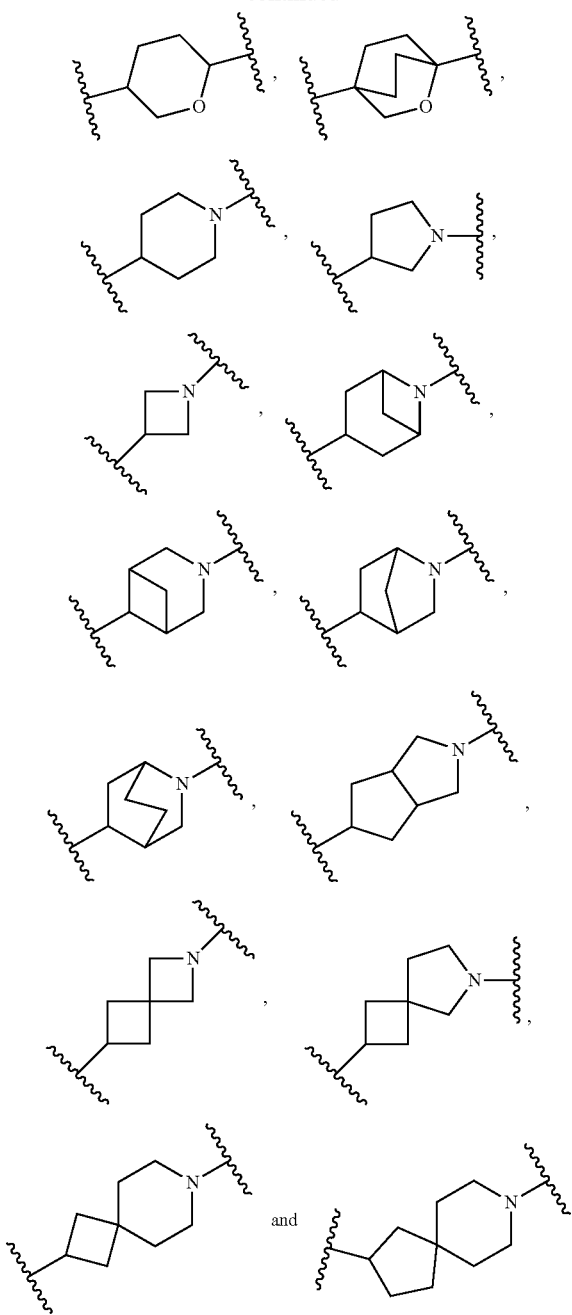

wherein each is optionally substituted with one to four halo.

In certain embodiments, provided is a compound of Formula II:

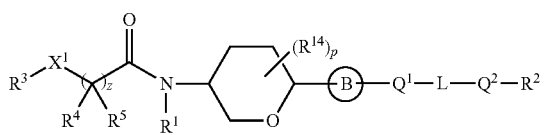

or a pharmaceutically acceptable salt, isotopically enriched analog, stereoisomer, mixture of stereoisomers, or prodrug thereof, wherein:

p is 0, 1, 2, 3, 4, 5 or 6;

ring B is a 5- or 6-membered heteroaryl or phenyl, wherein each is optionally substituted with one to three $R^{13}$;

$Q^1$ and $Q^2$ are each independently O, S or $NR^{15}$;

L is a $C_{1-6}$ alkylene linker, optionally substituted with one to three substituents independently selected from halo, cyano, nitro, —$OR^6$, —$SR^6$, —$SF_5$, —$NR^6R^7$, $C_{1-6}$ alkyl, $C_{2-6}$ alkenyl, $C_{2-6}$ alkynyl, —$C(O)R^6$, —$C(O)OR^6$, —$OC(O)OR^6$, —$OC(O)R^6$, —$C(O)NR^6R^7$, —$OC(O)NR^6R^7$, —$NR^6C(O)NR^7R^8$, —$S(O)_{1-2}R^6$, —$S(O)_{1-2}NR^6$, —$NR^6S(O)_{1-2}R^7$, —$NR^6S(O)_{1-2}NR^7R^8$, —$NR^6C(O)R^7$, and —$NR^6C(O)OR^7$;

z is 0 or 1;

$X^1$ is O, $NR^9$ or a bond;

$R^1$ is hydrogen, $C_{1-12}$ alkyl, $C_{2-12}$ alkenyl, $C_{2-12}$ alkynyl, $C_{3-10}$ cycloalkyl, or heterocyclyl, each of which, other than hydrogen, is optionally substituted with one to three $R^{11}$;

$R^2$ is $C_{1-6}$ haloalkyl;

$R^3$ is hydrogen, $C_{1-12}$ alkyl, $C_{2-12}$ alkenyl, $C_{2-12}$ alkynyl, $C_{3-10}$ cycloalkyl, heterocyclyl, aryl, or heteroaryl, each of which, other than hydrogen, is optionally substituted with one to five $R^{11}$;

$R^4$ and $R^5$ are independently hydrogen, $C_{1-12}$ alkyl, $C_{2-12}$ alkenyl or $C_{2-12}$ alkynyl, each of which, other than hydrogen, is independently optionally substituted with one to five $R^1$;

or $R^3$ and $R^4$, together with the atoms to which they are attached, join to form a $C_{3-10}$ cycloalkyl or heterocyclyl, each of which is optionally substituted with one to five $R^{11}$;

or $R^4$ and $R^5$, together with the atoms to which they are attached, join to form a $C_{3-10}$ cycloalkyl or heterocyclyl, each of which is optionally substituted with one to five $R^{11}$;

each of $R^6$, $R^7$, and $R^8$ is independently hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{20}$, —$C(O)OR^{20}$, —$C(O)NR^{20}R^{21}$, —$S(O)_{1-2}R^{20}$ or —$S(O)_{1-2}NR^{20}$, wherein each alkyl, alkenyl, alkynyl, cycloalkyl, heterocyclyl, aryl, and heteroaryl of $R^6$, $R^7$, and $R^8$ is independently optionally substituted with one to five $R^{12}$; or two of $R^6$, $R^7$, and $R^8$ are taken together with the atoms to which they are attached to form heterocyclyl independently optionally substituted by one to three halo, oxo, or $C_{1-12}$ alkyl independently optionally substituted by one to three oxo, halo, hydroxyl, or amino;

$R^9$ is hydrogen, $C_{1-12}$ alkyl, $C_{2-12}$ alkenyl, $C_{2-12}$ alkynyl, $C_{3-10}$ cycloalkyl, or heterocyclyl, each of which, other than hydrogen, is optionally substituted with one to three $R^{11}$;

each $R^{11}$ is independently halo, cyano, nitro, oxo, —$OR^6$, —$SR^6$, —$SF_5$, —$NR^6R^7$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^6$, —$C(O)OR^6$, —$OC(O)OR^6$, —$OC(O)R^6$, —$C(O)NR^6R^7$, —$OC(O)NR^6R^7$, —$NR^6C(O)NR^7R^8$, —$S(O)_{1-2}R^6$, —$S(O)_{1-2}NR^6$, —$NR^6S(O)_{1-2}R^7$, —$NR^6S(O)_{1-2}NR^7R^8$, —$NR^6C(O)R^7$, or —$NR^6C(O)OR^7$, wherein each alkyl, alkenyl, alkynyl, cycloalkyl, heterocyclyl, aryl, and heteroaryl of $R^{11}$ is independently optionally substituted with one to five $R^{12}$;

each $R^{12}$ is independently halo, cyano, nitro, oxo, —$OR^{30}$, —$SR^{30}$, —$SF_5$, —$NR^{30}R^{31}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{30}$, —$C(O)OR^{30}$, —$OC(O)OR^{30}$, —$OC(O)R^{30}$, —$C(O)NR^{30}R^{31}$, —$OC(O)NR^{30}R^{31}$, —$NR^{30}C(O)NR^{30}R^{31}$, —$S(O)_{1-2}R^{30}$, —$S(O)_{1-2}NR^{30}$, —$NR^{30}S(O)_{1-2}R^{31}$, —$NR^{30}S(O)_{1-2}NR^{30}R^{31}$, —$NR^{30}C(O)R^{31}$, or —NR$^{30}$C(=O)OR$^{31}$, wherein each alkyl, alkenyl, alkynyl, cycloalkyl, heterocyclyl, aryl, and heteroaryl of R$^{12}$ is independently optionally substituted with one to three halo or C$_{1-12}$ alkyl independently optionally substituted by one to three oxo, halo, hydroxyl, or amino;

each R$^{13}$ is independently halo, cyano, nitro, oxo, —OR$^{30}$, —SR$^{30}$, —SF$_5$, —NR$^{30}$R$^{31}$, C$_{1-12}$ alkyl, C$_{2-12}$ alkenyl, C$_{2-12}$ alkynyl, C$_{3-10}$ cycloalkyl, heterocyclyl, aryl, heteroaryl, —C(O)R$^{30}$, —C(O)OR$^{30}$, —OC(O)OR$^{30}$, —OC(O)R$^{30}$, —C(O)NR$^{30}$R$^{31}$, —OC(O)NR$^{30}$R$^{31}$, —NR$^{30}$C(O)NR$^{30}$R$^{31}$, —S(O)$_{1-2}$R$^{30}$, —S(O)$_{1-2}$NR$^{30}$, —NR$^{30}$S(O)$_{1-2}$R$^{31}$, —NR$^{30}$S(O)$_{1-2}$NR$^{30}$R$^{31}$, —NR$^{30}$C(O)R$^{31}$, or —NR$^{30}$C(=O)OR$^{31}$, wherein each alkyl, alkenyl, alkynyl, cycloalkyl, heterocyclyl, aryl, and heteroaryl of R$^{13}$ is independently optionally substituted with one to three halo or C$_{1-12}$ alkyl independently optionally substituted by one to three oxo, halo, hydroxyl, or amino;

each R$^{14}$ is independently halo, cyano, —NR$^6$R$^7$, C$_{1-6}$ alkyl, C$_{1-6}$ alkoxy, or C$_{1-6}$ haloalkyl, or two R$^{14}$ together with the atoms to which they are attached form a ring or a C=O;

each R$^{15}$ is independently hydrogen, C$_{1-6}$ alkyl, or C$_{1-6}$ haloalkyl;

each R$^{20}$ and R$^{21}$ is independently hydrogen or C$_{1-12}$ alkyl independently optionally substituted with one to three oxo, halo, hydroxyl, or amino; or R$^{20}$ and R$^{21}$ are taken together with the atoms to which they are attached to form heterocyclyl independently optionally substituted by one to three halo or C$_{1-12}$ alkyl independently optionally substituted by one to three oxo, halo, hydroxyl, or amino; and each R$^{30}$ and R$^{31}$ is independently hydrogen or C$_{1-12}$ alkyl independently optionally substituted with one to three oxo, halo, hydroxyl, or amino; or R$^{30}$ and R$^{31}$ are taken together with the atoms to which they are attached to form heterocyclyl independently optionally substituted by one to three halo or C$_{1-12}$ alkyl independently optionally substituted by one to three oxo, halo, hydroxyl, or amino.

In certain embodiments, when z is 0, X$^1$ is not O.

In certain embodiments, each R$^{14}$ is independently hydrogen, halo, or C$_{1-6}$ alkoxy.

In certain embodiments, p is 0, 1, 2, 3, 4, or 5. In certain embodiments, p is 0, 1, 2, 3, or 4. In certain embodiments, p is 0, 1, 2, or 3. In certain embodiments, p is 0, 1, or 2. In certain embodiments, p is 1. In certain embodiments, p is 0.

In certain embodiments, two R$^{14}$ together with the atoms to which they are attached form a C$_{3-6}$ cycloalkyl ring. In certain embodiments, two R$^{14}$ together with the atoms to which they are attached form a C$_3$ cycloalkyl ring.

In certain embodiments, two R$^{14}$ together form an ethylene bridge. In certain embodiments, two R$^{14}$ together form a methylene bridge.

In certain embodiments, provided is a compound of Formula IIA:

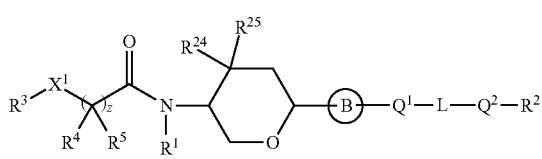

IIA or a pharmaceutically acceptable salt, isotopically enriched analog, stereoisomer, mixture of stereoisomers, or prodrug thereof, wherein z, R$^1$, R$^2$, R$^3$, R$^4$, R$^5$, ring B, Q$^1$, Q$^2$, L and X$^1$ are as defined herein, and R$^{24}$ and R$^{25}$ are each independently hydrogen, halo, or C$_{1-6}$ alkoxy. In certain embodiments, R$^{24}$ and R$^{25}$ are each independently halo. In certain embodiments, R$^{24}$ and R$^{25}$ are fluoro. In certain embodiments, R$^{24}$ and R$^{25}$ are independently hydrogen or C$_{1-6}$ alkoxy. In certain embodiments, one of R$^{24}$ and R$^{25}$ is hydrogen and one is methoxy.

In certain embodiments, provided is a compound of Formula IIB:

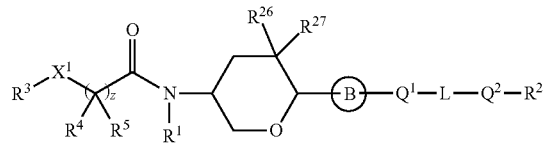

IIB or a pharmaceutically acceptable salt, isotopically enriched analog, stereoisomer, mixture of stereoisomers, or prodrug thereof, wherein z, R$^1$, R$^2$, R$^3$, R$^4$, R$^5$, ring B, Q$^1$, Q$^2$, L and X$^1$ are as defined herein, and R$^{26}$ and R$^{27}$ are each independently hydrogen, halo, or C$_{1-6}$ alkoxy. In certain embodiments, R$^{26}$ and R$^{27}$ are each independently halo. In certain embodiments, R$^{26}$ and R$^{27}$ are fluoro. In certain embodiments, R$^{26}$ and R$^{27}$ are independently hydrogen or C$_{1-6}$ alkoxy. In certain embodiments, one of R$^{26}$ and R$^{27}$ is hydrogen and one is methoxy.

In certain embodiments, provided is a compound of Formula IIC:

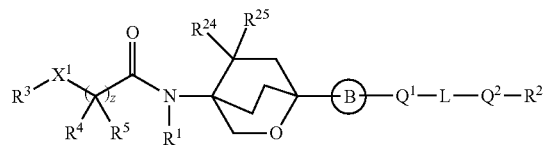

IIC or a pharmaceutically acceptable salt, isotopically enriched analog, stereoisomer, mixture of stereoisomers, or prodrug thereof, wherein z, R$^1$, R$^2$, R$^3$, R$^4$, R$^5$, ring B, Q$^1$, Q$^2$, L and X$^1$ are as defined herein, and R$^{24}$ and R$^{25}$ are each independently hydrogen, halo, or C$_{1-6}$ alkoxy. In certain embodiments, R$^{24}$ and R$^{25}$ are each independently halo. In certain embodiments, R$^{24}$ and R$^{25}$ are fluoro. In certain embodiments, R$^{24}$ and R$^{25}$ are independently hydrogen or C$_{1-6}$ alkoxy. In certain embodiments, one of R$^{24}$ and R$^{25}$ is hydrogen and one is methoxy.

In certain embodiments, provided is a compound of Formula IID:

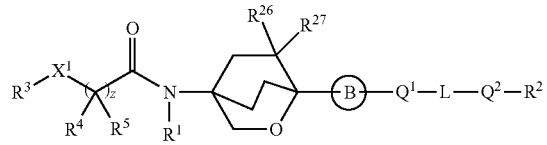

IID or a pharmaceutically acceptable salt, isotopically enriched analog, stereoisomer, mixture of stereoisomers, or prodrug thereof, wherein z, $R^1$, $R^2$, $R^3$, $R^4$, $R^5$, ring B, $Q^1$, $Q^2$, L and $X^1$ are as defined herein, and $R^{26}$ and $R^{27}$ are each independently hydrogen, halo, or $C_{1-6}$ alkoxy. In certain embodiments, $R^{26}$ and $R^{27}$ are each independently halo. In certain embodiments, $R^{26}$ and $R^{27}$ are fluoro. In certain embodiments, $R^{26}$ and $R^{27}$ are independently hydrogen or $C_{1-6}$ alkoxy. In certain embodiments, one of $R^{26}$ and $R^{27}$ is hydrogen and one is methoxy.

In certain embodiments, ring B is an optionally substituted five membered $C_{2-4}$ heteroaryl ring. In certain embodiments, ring B is a five membered $C_{2-4}$ heteroaryl ring optionally substituted with one to three $R^{13}$.

In certain embodiments, ring B is an optionally substituted five membered $C_{2-4}$ heteroaryl ring having 1 to 3 nitrogen ring atoms. In certain embodiments, ring B is a five membered $C_{2-4}$ heteroaryl ring having 1 to 3 nitrogen ring atoms optionally substituted with one to three $R^{13}$.

In certain embodiments, ring B is an optionally substituted triazolyl, oxazolyl, imidazolyl, oxadiazolyl, or isoxazolyl. In certain embodiments, ring B is triazolyl, oxazolyl, imidazolyl, oxadiazolyl, or isoxazolyl optionally substituted with one to three $R^{13}$.

In certain embodiments, ring B is

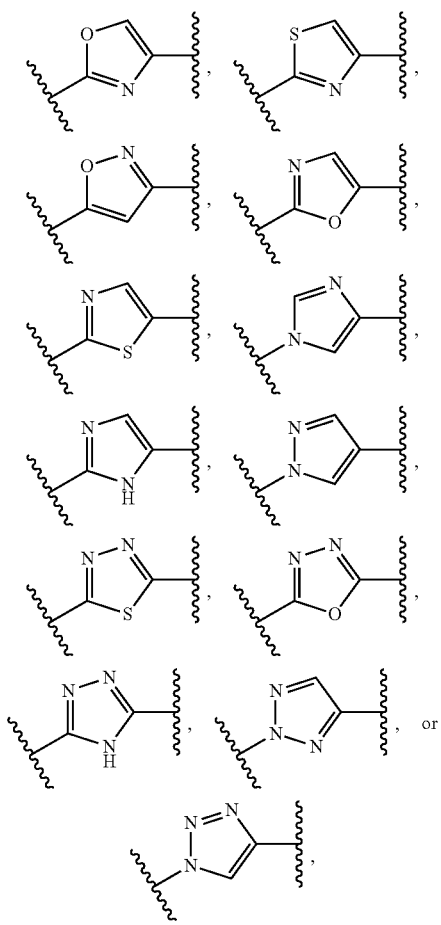

optionally substituted with one to three $R^{13}$.

In certain embodiments, ring B is a phenyl ring optionally substituted with one to three $R^{13}$.

In certain embodiments, ring B is optionally substituted with one to three $R^{13}$, where each $R^{13}$ is independently selected from halo, cyano, oxo, $C_{1-6}$ alkyl, $C_{1-6}$ alkoxy, $C_{1-6}$ haloalkyl, or $C_{1-6}$ haloalkoxy.

In certain embodiments, $R^2$ is —$CHF_2$, —$CF_3$ or —$CH_2CF_3$.

In certain embodiments, $Q^1$ is O.
In certain embodiments, $Q^2$ is O.
In certain embodiments, $Q^1$ is $NR^{15}$ and $Q^2$ is O.
In certain embodiments, $Q^1$ and $Q^2$ are each O.
In certain embodiments, L is a $C_{1-6}$ alkylene linker, optionally substituted with one or two methyl and optionally one to three halo. In certain embodiments, L is a $C_{1-6}$ alkylene linker, optionally substituted with one to three halo.

In certain embodiments, L is an ethylene linker, optionally substituted with one or two methyl and optionally one to three halo.

In certain embodiments, L is an ethylene linker, optionally substituted with one to three halo.

In certain embodiments, L is —$CH_2CH_2$—.
In certain embodiments, the moiety -$Q^1$-L-$Q^2$-$R^2$ is —$OCH_2CH_2OCH_2CF_3$. In certain embodiments, the moiety -$Q^1$-L-$Q^2$-$R^2$ is —$OCH_2CH_2OCF_3$. In certain embodiments, the moiety -$Q^1$-L-$Q^2$-$R^2$ is —$NR^{15}CH_2CH_2OCF_3$.

In certain embodiments, $R^4$ and $R^5$ are hydrogen.
In certain embodiments, $R^1$ is hydrogen.
In certain embodiments, $X^1$ is O.
In certain embodiments, $X^1$ is a bond.
In certain embodiments, $X^1$ is O or $NR^9$.
In certain embodiments, $X^1$ is $NR^9$. In certain embodiments, $R^9$ is hydrogen, $C_{1-12}$ alkyl, $C_{2-12}$ alkenyl, $C_{2-12}$ alkynyl, $C_{3-10}$ cycloalkyl, or heterocyclyl, each of which, other than hydrogen, is optionally substituted with one to three halo, oxo, acetyl, amino, hydroxyl or $C_{1-12}$ alkyl.

In certain embodiments, $R^3$ is $C_{1-12}$ alkyl, $C_{2-12}$ alkenyl, $C_{2-12}$ alkynyl, $C_{3-10}$ cycloalkyl, heterocyclyl, aryl, or heteroaryl, each of which is optionally substituted with one to five $R^{11}$. In certain embodiments, $R^3$ is $C_{1-12}$ alkyl, $C_{2-12}$ alkenyl, $C_{2-12}$ alkynyl, $C_{3-10}$ cycloalkyl, heterocyclyl, aryl, or heteroaryl, each of which is optionally substituted with one to three $R^{11}$.

In certain embodiments, $R^3$ is hydrogen, $C_{1-12}$ alkyl, $C_{2-12}$ alkenyl, $C_{2-12}$ alkynyl, $C_{3-10}$ cycloalkyl, 4-15 membered heterocyclyl, $C_{6-10}$ aryl, or 5-15 membered heteroaryl, each of which, other than hydrogen, is optionally substituted with one to five $R^{11}$. In certain embodiments, $R^3$ is hydrogen, $C_{1-12}$ alkyl, $C_{2-12}$ alkenyl, $C_{2-12}$ alkynyl, $C_{3-10}$ cycloalkyl, 4-15 membered heterocyclyl, $C_{6-10}$ aryl, or 5-15 membered heteroaryl, each of which, other than hydrogen, is optionally substituted with one to three $R^{11}$.

In certain embodiments, $R^3$ is $C_{3-10}$ cycloalkyl, heterocyclyl, aryl, or heteroaryl, each of which is optionally substituted with one to five $R^{11}$. In certain embodiments, $R^3$ is $C_{3-10}$ cycloalkyl, heterocyclyl, aryl, or heteroaryl, each of which is optionally substituted with one to three $R^{11}$.

In certain embodiments, $R^3$ is $C_{3-10}$ cycloalkyl, 4-15 membered heterocyclyl, aryl, or 5-15 membered heteroaryl, each of which is optionally substituted with one to five $R^{11}$. In certain embodiments, $R^3$ is $C_{3-10}$ cycloalkyl, 4-15 membered heterocyclyl, aryl, or 5-15 membered heteroaryl, each of which is optionally substituted with one to three $R^{11}$.

In certain embodiments, $R^3$ is $C_{3-10}$ cycloalkyl, aryl, or heteroaryl, each of which is optionally substituted with one to five $R^{11}$. In certain embodiments, $R^3$ is $C_{3-10}$ cycloalkyl, aryl, or heteroaryl, each of which is optionally substituted with one to three $R^{11}$.

In certain embodiments, $R^3$ is aryl or heteroaryl, each of which is optionally substituted with one to five $R^{11}$. In certain embodiments, $R^3$ is aryl or heteroaryl, each of which is optionally substituted with one to three $R^{11}$.

In certain embodiments, $R^3$ is aryl or heteroaryl, each of which is optionally substituted with one to five substituents independently selected from halo, cyano, $C_{1-12}$ haloalkyl, and $C_{1-12}$ haloalkoxy. In certain embodiments, $R^3$ is aryl or heteroaryl, each of which is optionally substituted with one to three substituents independently selected from halo, cyano, $C_{1-12}$ haloalkyl, and $C_{1-12}$ haloalkoxy.

In certain embodiments, $R^3$ is aryl or heteroaryl, each of which is optionally substituted with one to three chloro, fluoro, bromo, —$CF_3$, or a combination thereof. In certain embodiments, $R^3$ is aryl or heteroaryl, each of which is optionally substituted with one to three chloro, fluoro, —$CF_3$, or a combination thereof.

In certain embodiments, $R^3$ is

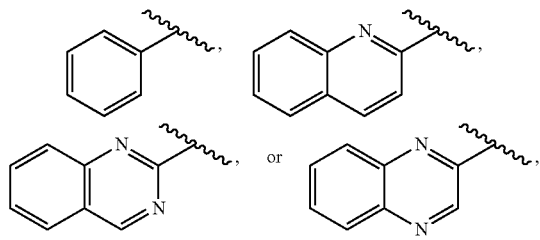

each of which is optionally substituted with one to five $R^{11}$. In certain embodiments, $R^3$ is

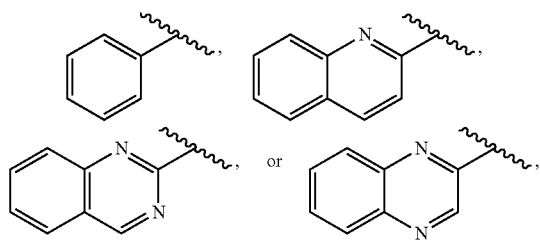

each of which is optionally substituted with one to three $R^{11}$.
In certain embodiments, $R^3$ is

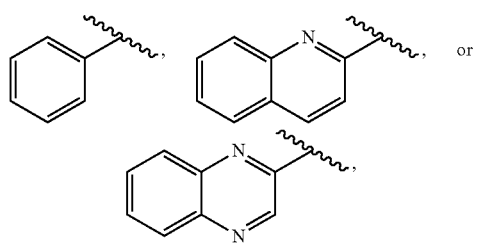

each of which is optionally substituted with one to five $R^{11}$. In certain embodiments, $R^3$ is

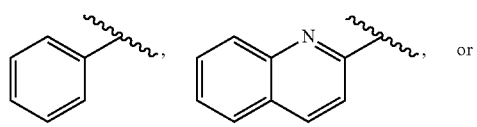

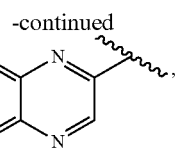

each of which is optionally substituted with one to three $R^{11}$.

In certain embodiments, $R^3$ is optionally substituted phenyl. In certain embodiments, $R^3$ is phenyl optionally substituted with one to five $R^{11}$. In certain embodiments, $R^3$ is phenyl optionally substituted with one to three $R^{11}$.

In certain embodiments, $R^3$ is optionally substituted heteroaryl. In certain embodiments, $R^3$ is heteroaryl optionally substituted with one to five $R^{11}$. In certain embodiments, $R^3$ is heteroaryl optionally substituted with one to three $R^{11}$.

In certain embodiments, $R^3$ is cyclobutyl, pyridinyl, triazolyl, or phenyl, each of which is optionally substituted with one to five $R^{11}$. In certain embodiments, $R^3$ is cyclobutyl, pyridinyl, triazolyl, or phenyl, each of which is optionally substituted with one to three $R^{11}$.

In certain embodiments, $R^3$ is cyclobutyl, triazolyl, or phenyl, each of which is optionally substituted with one to three $R^{11}$.

In certain embodiments, at least one $R^{11}$ is halo.
In certain embodiments, at least one $R^{11}$ is $C_{1-6}$ haloalkyl.
In certain embodiments, at least one $R^{11}$ is —$CF_3$.
In certain embodiments, at least one $R^{11}$ is —$CHF_2$.
In certain embodiments, at least one $R^{11}$ is —$OCF_3$.
In certain embodiments, at least one $R^{11}$ is —$OCHF_2$.

In certain embodiments, $R^3$ is phenyl independently optionally substituted with one to five halo, cyano, $C_{1-12}$ alkyl optionally substituted with one to three halo, or $C_{1-12}$ alkoxy optionally substituted with one to three halo. In certain embodiments, $R^3$ is phenyl independently optionally substituted with one to five halo, cyano, $C_{1-12}$ alkyl optionally substituted with one to three halo, or $C_{1-12}$ alkoxy optionally substituted with one to three halo.

In certain embodiments, $R^3$ is phenyl optionally substituted with one to five substituents independently selected from halo, cyano, $C_{1-12}$ haloalkyl, and $C_{1-12}$ haloalkoxy. In certain embodiments, $R^3$ is phenyl optionally substituted with one to three substituents independently selected from halo, cyano, $C_{1-12}$ haloalkyl, and $C_{1-12}$ haloalkoxy.

In certain embodiments, $R^3$ is phenyl substituted with chloro, fluoro, bromo, —$CF_3$, or a combination thereof. In certain embodiments, $R^3$ is phenyl substituted with chloro, fluoro, bromo, or a combination thereof. In certain embodiments, $R^3$ is phenyl substituted with chloro, fluoro, —$CF_3$, or a combination thereof. In certain embodiments, $R^3$ is phenyl substituted with chloro, fluoro, or a combination thereof.

In certain embodiments, $R^3$ is heteroaryl independently optionally substituted with one to five halo, cyano, $C_{1-12}$ alkyl optionally substituted with one to three halo, or $C_{1-12}$ alkoxy optionally substituted with one to three halo. In certain embodiments, $R^3$ is heteroaryl independently optionally substituted with one to three halo.

In certain embodiments, $R^3$ is 4-chlorophenyl, 4-chloro-3-fluorophenyl, 2-((trifluoromethoxy)methyl)cyclopropyl, or 3-(trifluoromethoxy)cyclobutyl.

In certain embodiments, $R^3$ is 4-chlorophenyl, 4-fluorophenyl, 4-chloro-3-fluorophenyl, 2-((trifluoromethoxy)methyl)cyclopropyl, or 3-(trifluoromethoxy)cyclobutyl.

In certain embodiments, $R^3$ is 4-chlorophenyl, 4-fluorophenyl, 4-chloro-3-fluorophenyl, 4-chloro-2-fluorophenyl, 2,4-difluorophenyl, 3,4-difluorophenyl, 4-methylphenyl, 2-((trifluoromethoxy)methyl)cyclopropyl, or 3-(trifluoromethoxy)cyclobutyl.

In certain embodiments, $R^3$ is 4-chlorophenyl, 4-fluorophenyl, 4-chloro-2-fluorophenyl, 4-chloro-3-fluorophenyl, 4-chloro-2-fluorophenyl, 2,4-difluorophenyl, 3,4-difluorophenyl, 4-methylphenyl, 2-((trifluoromethoxy)methyl)cyclopropyl, 6-(trifluoromethyl)pyridin-3-yl, 4-(trifluoromethyl)phenyl, 7-bromoimidazo[1,2-a]pyridin-2-yl, 5-chlorobenzo[d]thiazol-2-yl, 7-chloroisoquinolin-3-yl, 6-chlorochroman-2-yl, 3-(trifluoromethoxy)pyrrolidin-1-yl, or 3-(trifluoromethoxy)cyclobutyl.

In certain embodiments, $R^3$ is 4-chlorophenyl, 4-fluorophenyl, 4-chloro-2-fluorophenyl, 4-chloro-3-fluorophenyl, 4-chloro-2-fluorophenyl, 2,4-difluorophenyl, 3,4-difluorophenyl, 4-methylphenyl, 2-((trifluoromethoxy)methyl)cyclopropyl, 6-(trifluoromethyl)pyridin-3-yl, 4-(trifluoromethyl)phenyl, 7-bromoimidazo[1,2-a]pyridin-2-yl, 5-chlorobenzo[d]thiazol-2-yl, 7-chloroisoquinolin-3-yl, 6-chloroquinolin-2-yl, 6-fluoroisoquinolin-2-yl, 6-(trifluoromethyl)quinolin-2-yl, 6-chlorochroman-2-yl, 6-fluorochroman-2-yl, 6,7-difluoroquinolin-2-yl, 5,6-difluoroquinolin-2-yl, 3-(trifluoromethoxy)pyrrolidin-1-yl, or 3-(trifluoromethoxy)cyclobutyl.

In certain embodiments, $R^3$ is 4-chlorophenyl, 4-bromophenyl, 3-fluoro-4-(trifluoromethyl)phenyl, 6-(trifluoromethyl)quinazolin-2-yl, 6-(trifluoromethyl)quinolin-2-yl, 6-(trifluoromethyl)quinoxalin-2-yl, 6-chloro-7-fluoro-quinoxalin-2-yl, 6-fluoro-7-(trifluoromethyl)quinoxalin-2-yl, 7-fluoro-6-(trifluoromethyl)quinoxalin-2-yl, 7-fluoro-6-(trifluoromethyl)quinolin-2-yl, or 6-chloro-7-fluoro-quinolin-2-yl.

In certain embodiments, z is 0. In certain embodiments, z is 1.

In certain embodiments, z is 0, $X^1$ is a bond, and R is optionally substituted heteroaryl. In certain embodiments, z is 0, $X^1$ is a bond, and R is heteroaryl optionally substituted with one to three $R^{11}$.

In certain embodiments, $R^4$ and $R^5$ are independently hydrogen, $C_{1-12}$ alkyl, $C_{2-12}$ alkenyl or $C_{2-12}$ alkynyl, each of which, other than hydrogen, is independently optionally substituted with one to three (e.g., one to three) halo, oxo, acetyl, amino, or hydroxyl.

In certain embodiments, $R^4$ and $R^5$ are hydrogen.

In certain embodiments, provided is a compound of Formula IIIA:

IIIA

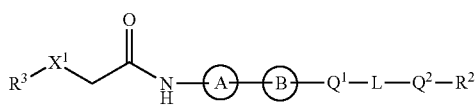

wherein each of $R^2$, $R^3$, ring A, ring B, $Q^1$, $Q^2$, L and $X^1$ are as defined herein.

In certain embodiments, provided is a compound of Formula IIIB:

IIIB

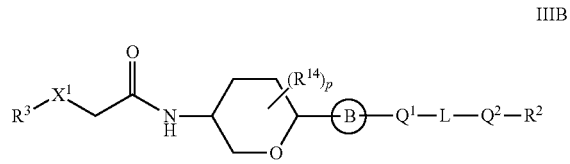

wherein each of $R^2$, $R^3$, $R^{14}$, p, ring B, $Q^1$, $Q^2$, L and $X^1$ are as defined herein.

In certain embodiments, provided is a compound of Formula IIIC:

IIIC

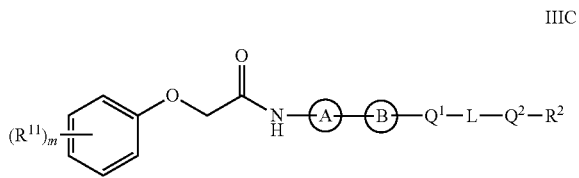

wherein each of $R^2$, $R^{11}$, m, ring A, ring B, $Q^1$, $Q^2$, and L are as defined herein.

In certain embodiments, provided is a compound of Formula IIID:

IIID

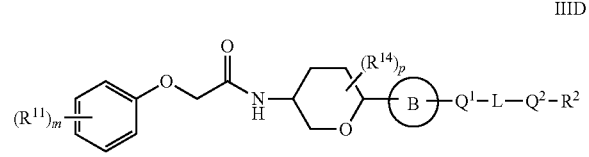

wherein each of $R^2$, $R^{11}$, m, $R^{14}$, p, ring B, $Q^1$, $Q^2$, and L are as defined herein.

In certain embodiments, provided is a compound of Formula IIIE:

IIIE

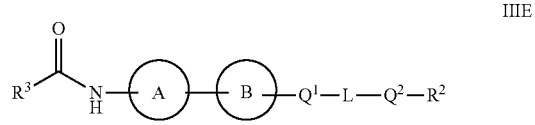

wherein each of $R^2$, $R^3$, ring A, ring B, $Q^1$, $Q^2$, and L are as defined herein.

In certain embodiments, provided is a compound of Formula IIIF:

IIIF

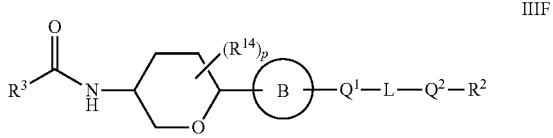

wherein each of $R^2$, $R^3$, $R^{14}$, p, ring B, $Q^1$, $Q^2$, and L are as defined herein.

In certain embodiments, provided is a compound selected from Table 1:
TABLE 1
| Ex. | Structure |
|---|---|
| 1 | 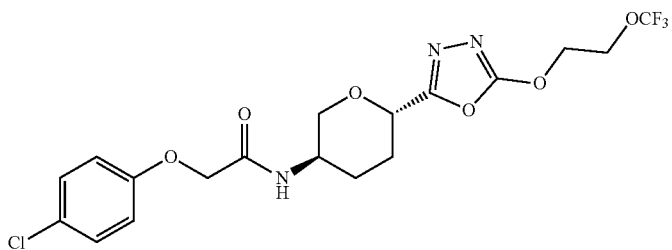 |
| 2 | 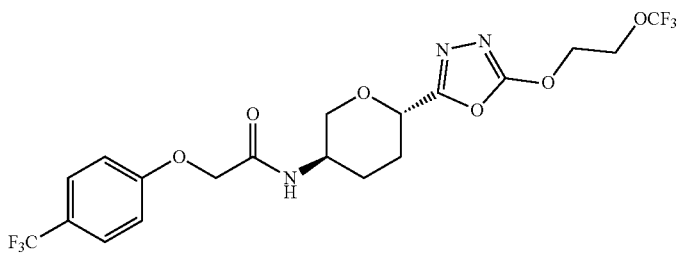 [SMILES: O=C(COc1ccc(C(F)(F)F)cc1)N[C@@H]1CC[C@@H](c2nnc(OCCOC(F)(F)F)o2)OC1] |
| 3 | 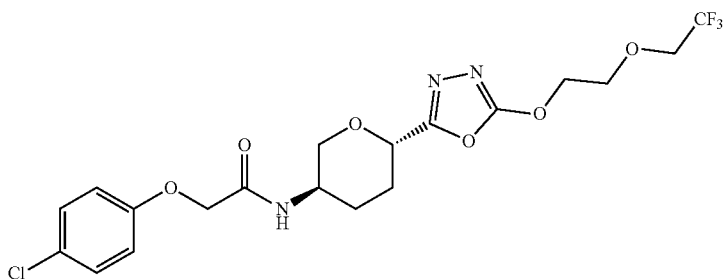 [SMILES: O=C(COc1ccc(Cl)cc1)N[C@@H]1CC[C@@H](c2nnc(OCCOCC(F)(F)F)o2)OC1] |
| 4 | 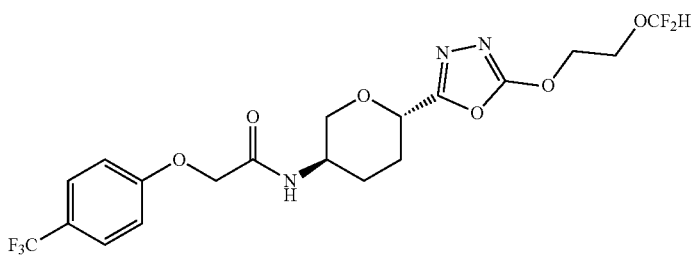 |
| 5 | 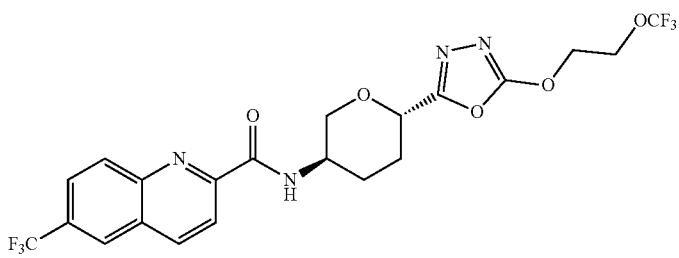 [SMILES: O=C(N[C@@H]1CC[C@@H](c2nnc(OCCOC(F)(F)F)o2)OC1)c1ccc2cc(C(F)(F)F)ccc2n1] |

TABLE 1-continued
| Ex. | Structure |
|---|---|
| 6 | 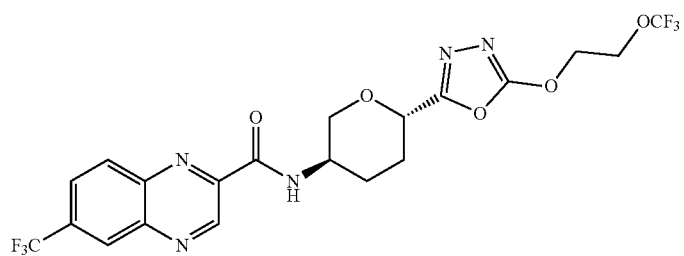 [SMILES: O=C(N[C@@H]1CC[C@@H](c2nnc(OCCOC(F)(F)F)o2)OC1)c1cnc2cc(C(F)(F)F)ccc2n1] |
| 7 | 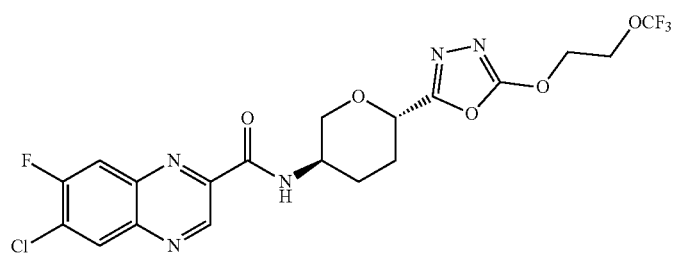 [SMILES: O=C(N[C@@H]1CC[C@@H](c2nnc(OCCOC(F)(F)F)o2)OC1)c1cnc2cc(Cl)c(F)cc2n1] |
| 8 | 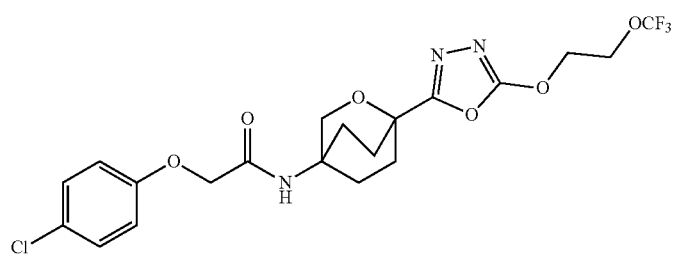 [SMILES: O=C(COc1ccc(Cl)cc1)NC12CCC(c3nnc(OCCOC(F)(F)F)o3)(CC1)OC2] |
| 9 | 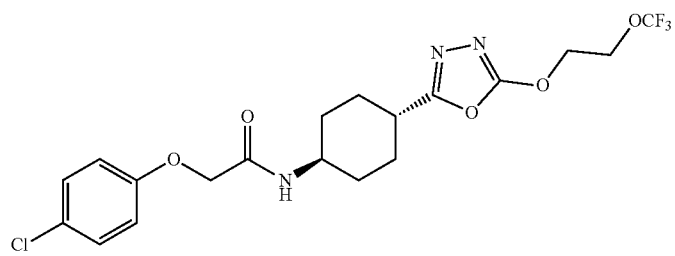 [SMILES: O=C(COc1ccc(Cl)cc1)N[C@H]1CC[C@H](c2nnc(OCCOC(F)(F)F)o2)CC1] |
| 10 | 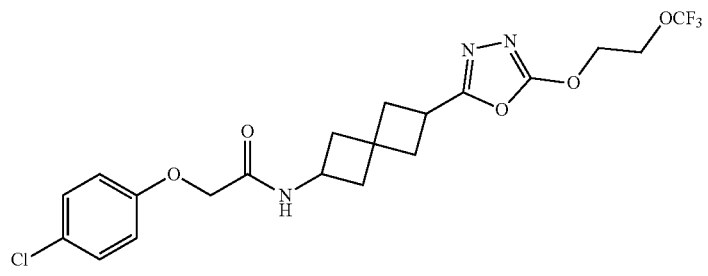 [SMILES: O=C(COc1ccc(Cl)cc1)NC1CC2(C1)CC(c1nnc(OCCOC(F)(F)F)o1)C2] |
| 11 | 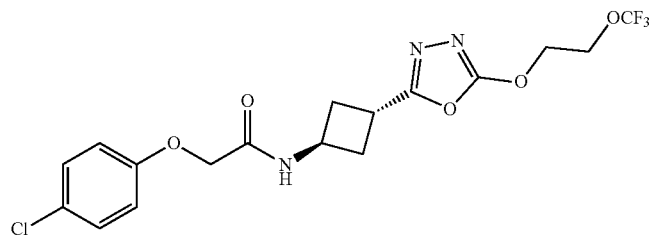 [SMILES: O=C(COc1ccc(Cl)cc1)N[C@H]1C[C@H](c2nnc(OCCOC(F)(F)F)o2)C1] |

TABLE 1-continued
| Ex. | Structure |
|---|---|
| 12 | 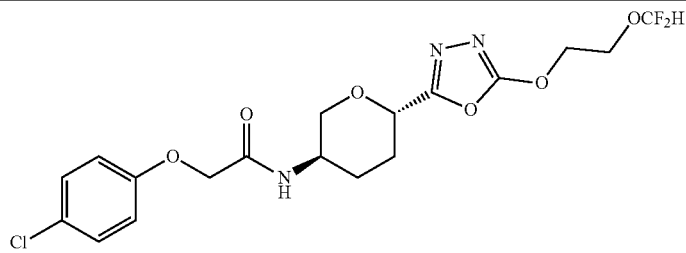 |
| 13 | 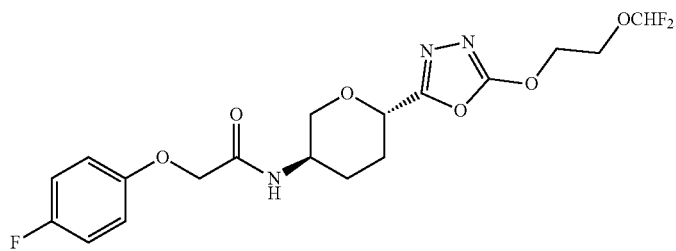 [SMILES: O=C(COc1ccc(F)cc1)N[C@@H]1CC[C@@H](c2nnc(OCCOC(F)F)o2)OC1] |
| 14 | 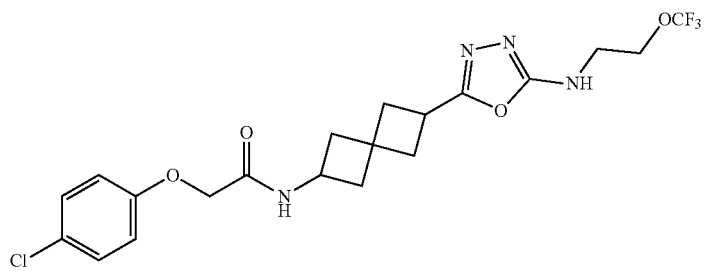 [SMILES: O=C(COc1ccc(Cl)cc1)NC1CC2(C1)CC(c1nnc(NCCOC(F)(F)F)o1)C2] |
| 15 | 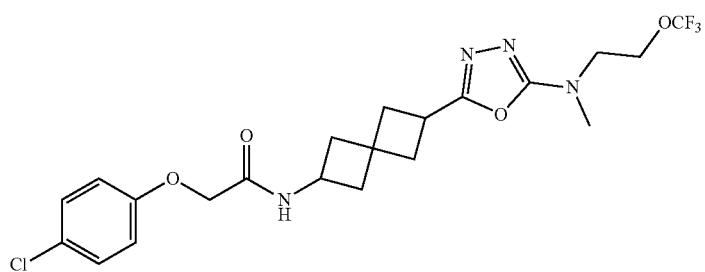 [SMILES: CN(CCOC(F)(F)F)c1nnc(C2CC3(CC(NC(=O)COc4ccc(Cl)cc4)C3)C2)o1] |
| 16 | 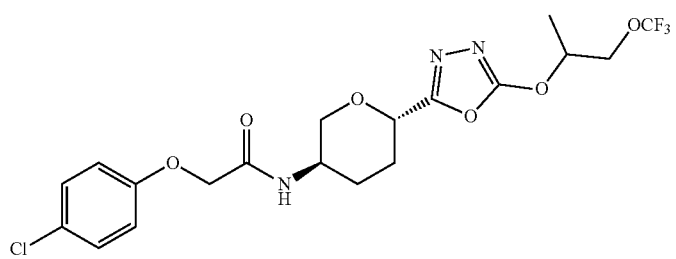 [SMILES: CC(COC(F)(F)F)Oc1nnc([C@@H]2CC[C@@H](NC(=O)COc3ccc(Cl)cc3)CO2)o1] |
| 17 | 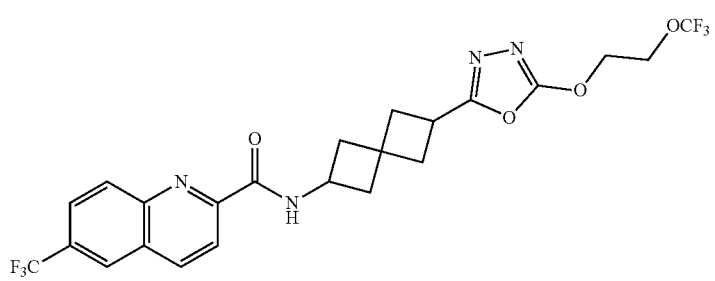 |

TABLE 1-continued
| Ex. | Structure |
|---|---|
| 18 | 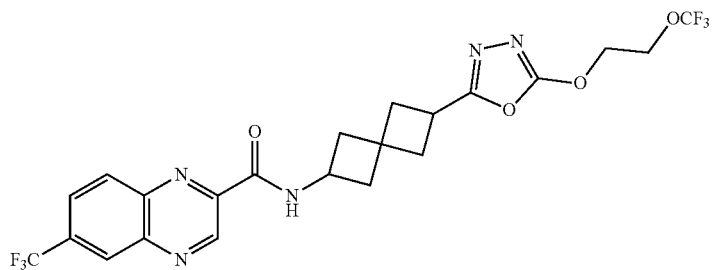 |
| 19 | 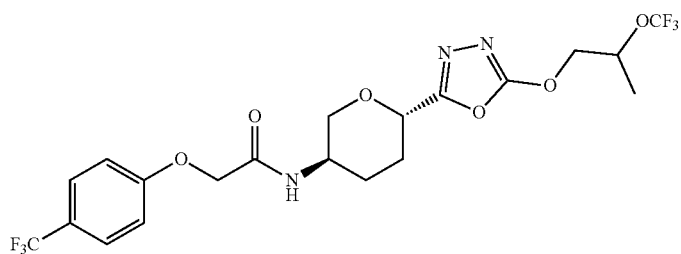 [SMILES: CC(COc1nnc([C@@H]2CC[C@@H](NC(=O)COc3ccc(C(F)(F)F)cc3)CO2)o1)OC(F)(F)F] |
| 20 | 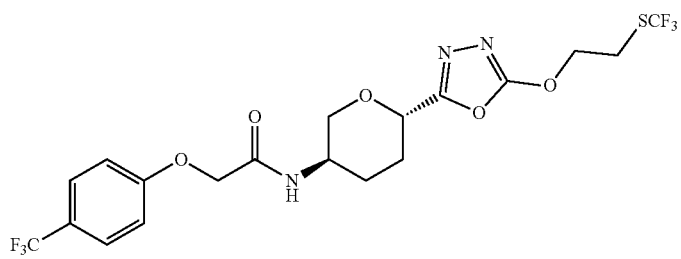 |
| 23 | 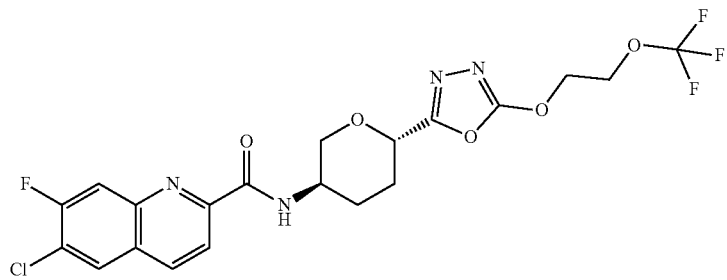 [SMILES: O=C(N[C@@H]1CC[C@@H](c2nnc(OCCOC(F)(F)F)o2)OC1)c1ccc2cc(Cl)c(F)cc2n1] |
| 24 | 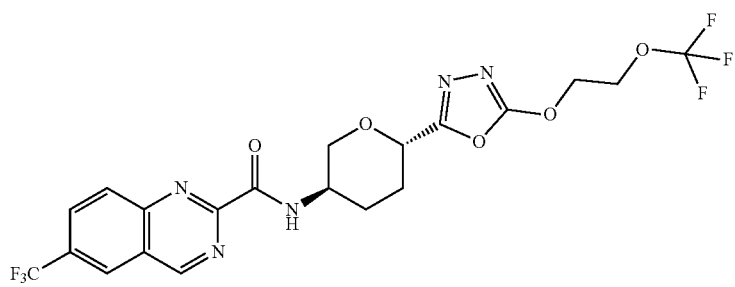 [SMILES: O=C(N[C@@H]1CC[C@@H](c2nnc(OCCOC(F)(F)F)o2)OC1)c1ncc2cc(C(F)(F)F)ccc2n1] |

TABLE 1-continued
| Ex. | Structure |
|---|---|
| 25 | 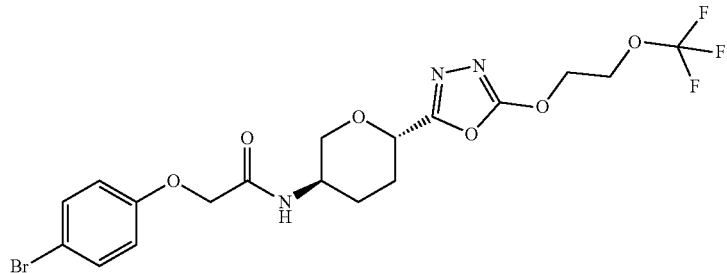 [SMILES: O=C(COc1ccc(Br)cc1)N[C@@H]1CC[C@@H](c2nnc(OCCOC(F)(F)F)o2)OC1] |
| 26 | 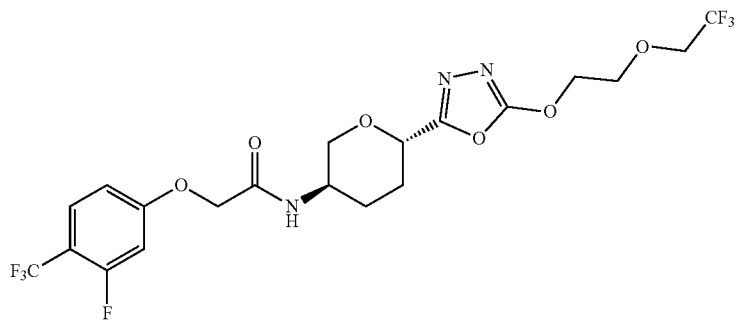 [SMILES: O=C(COc1ccc(C(F)(F)F)c(F)c1)N[C@@H]1CC[C@@H](c2nnc(OCCOCC(F)(F)F)o2)OC1] |
| 27 | 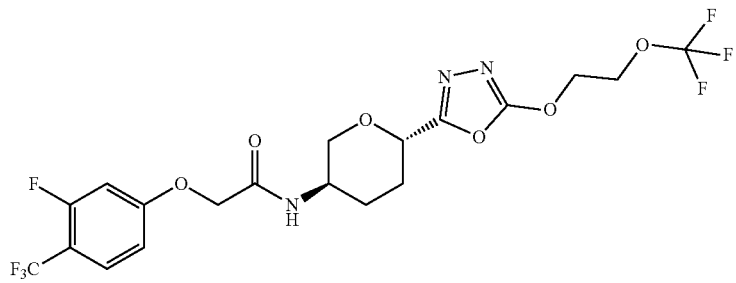 [SMILES: O=C(COc1ccc(C(F)(F)F)c(F)c1)N[C@@H]1CC[C@@H](c2nnc(OCCOC(F)(F)F)o2)OC1] |
| 28 | 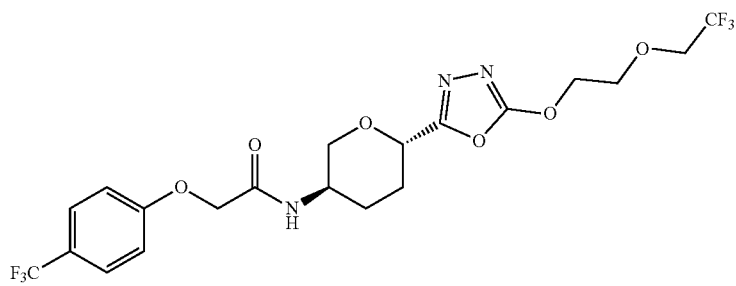 [SMILES: O=C(COc1ccc(C(F)(F)F)cc1)N[C@@H]1CC[C@@H](c2nnc(OCCOCC(F)(F)F)o2)OC1] |
| 29 | 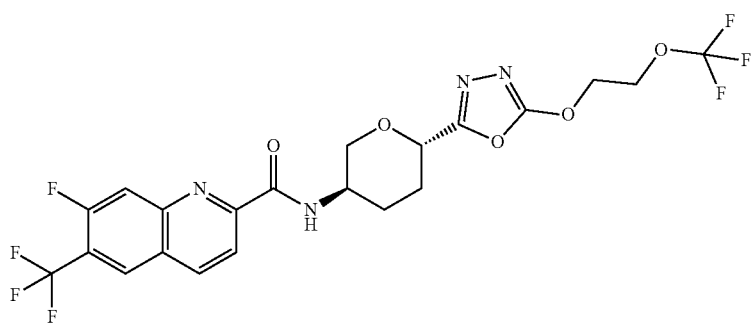 [SMILES: O=C(N[C@@H]1CC[C@@H](c2nnc(OCCOC(F)(F)F)o2)OC1)c1ccc2cc(C(F)(F)F)c(F)cc2n1] |

TABLE 1-continued
| Ex. | Structure |
|---|---|
| 30 | 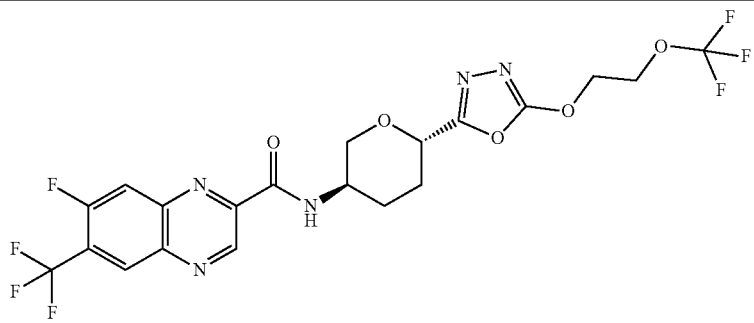 |
| 31 | 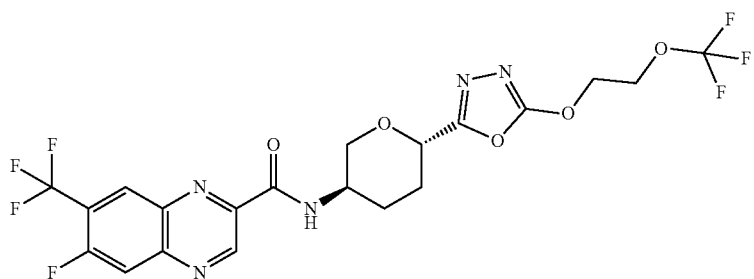 [SMILES: O=C(N[C@@H]1CC[C@@H](c2nnc(OCCOC(F)(F)F)o2)OC1)c1cnc2cc(F)c(C(F)(F)F)cc2n1] |
| 32 | 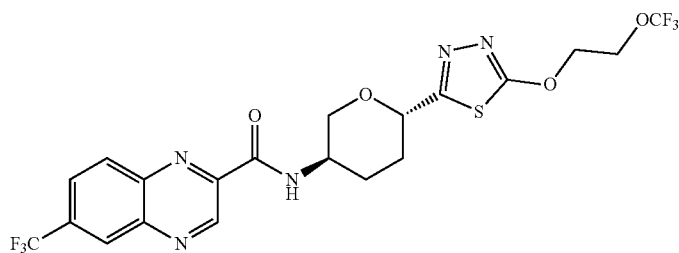 |
| 33 | 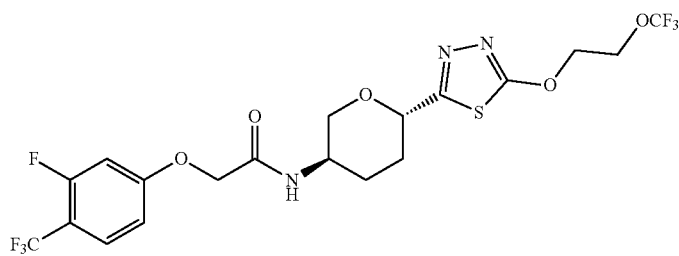 [SMILES: O=C(COc1ccc(C(F)(F)F)c(F)c1)N[C@@H]1CC[C@@H](c2nnc(OCCOC(F)(F)F)s2)OC1] |
or a pharmaceutically acceptable salt, isotopically enriched analog, prodrug, stereoisomer, or a mixture of stereoisomers thereof.
In certain embodiments, provided is a compound selected from Table 2.
TABLE 2
| Structure |
|---|
| 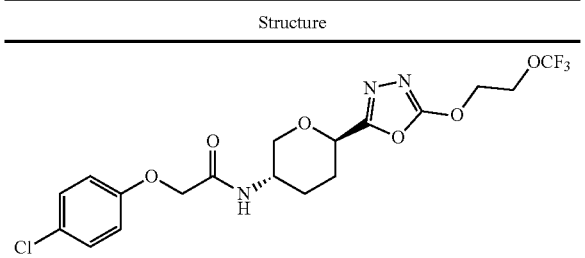 |
TABLE 2-continued
| Structure |
|---|
| 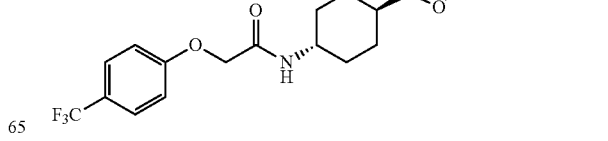 |

TABLE 2-continued
Structure
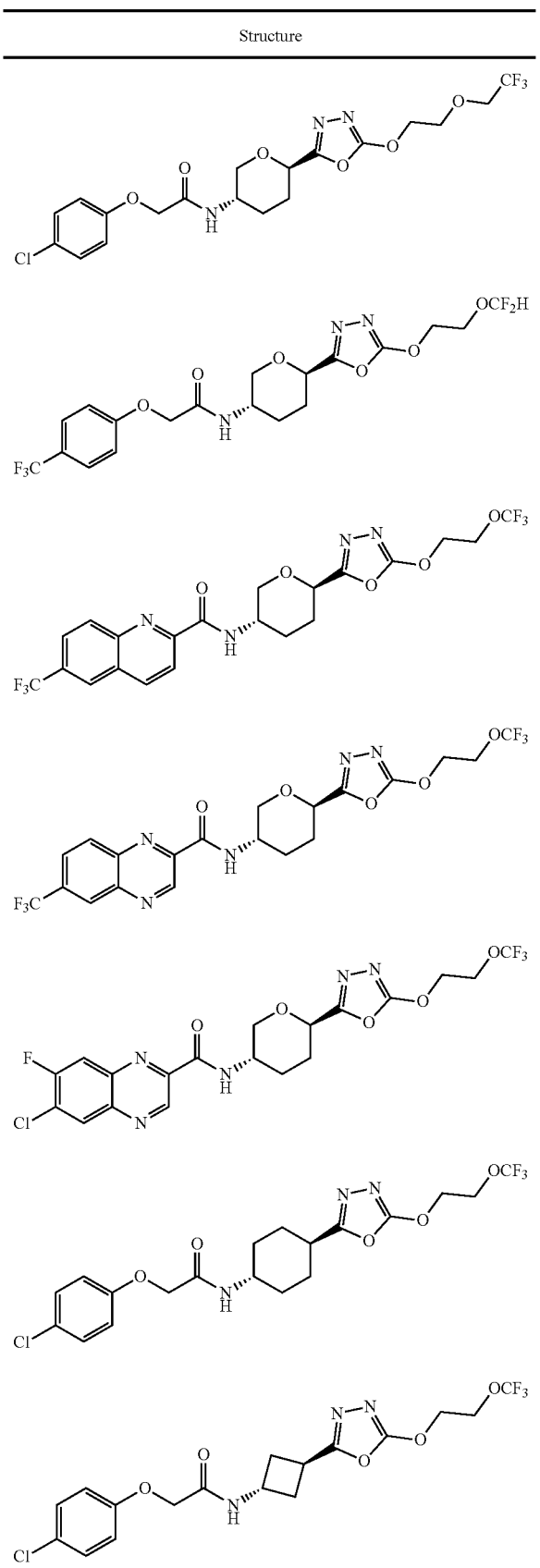
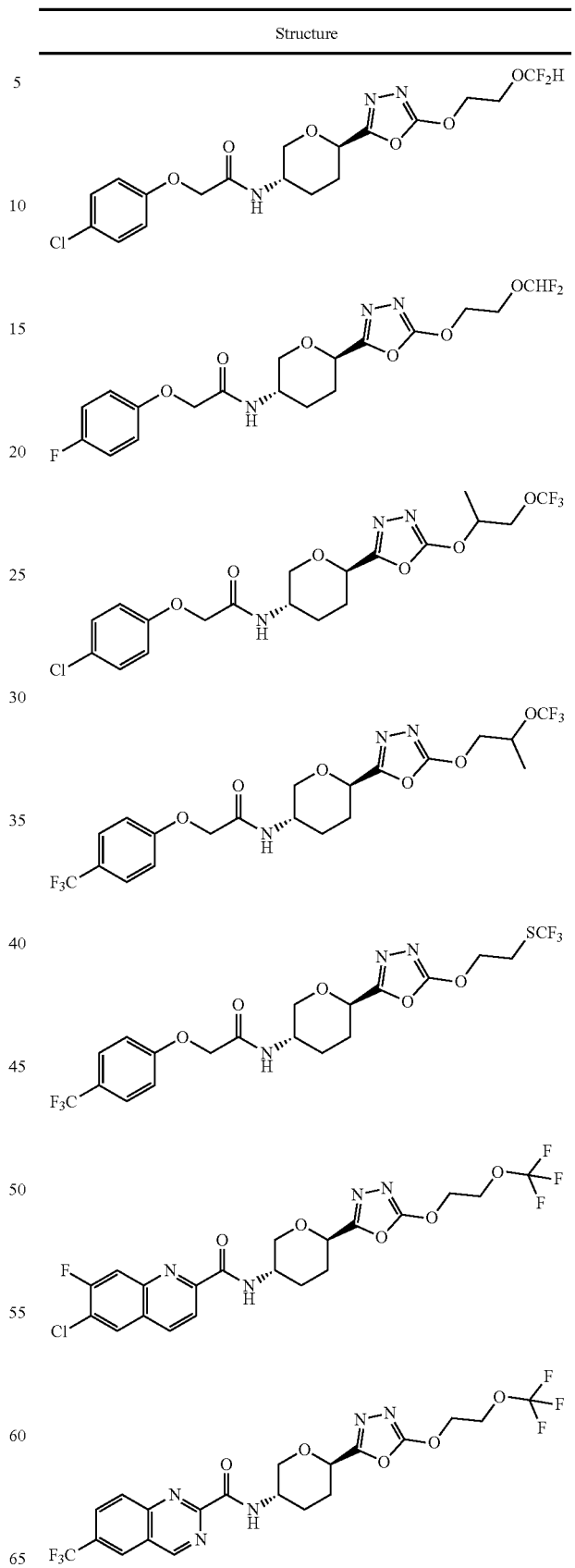

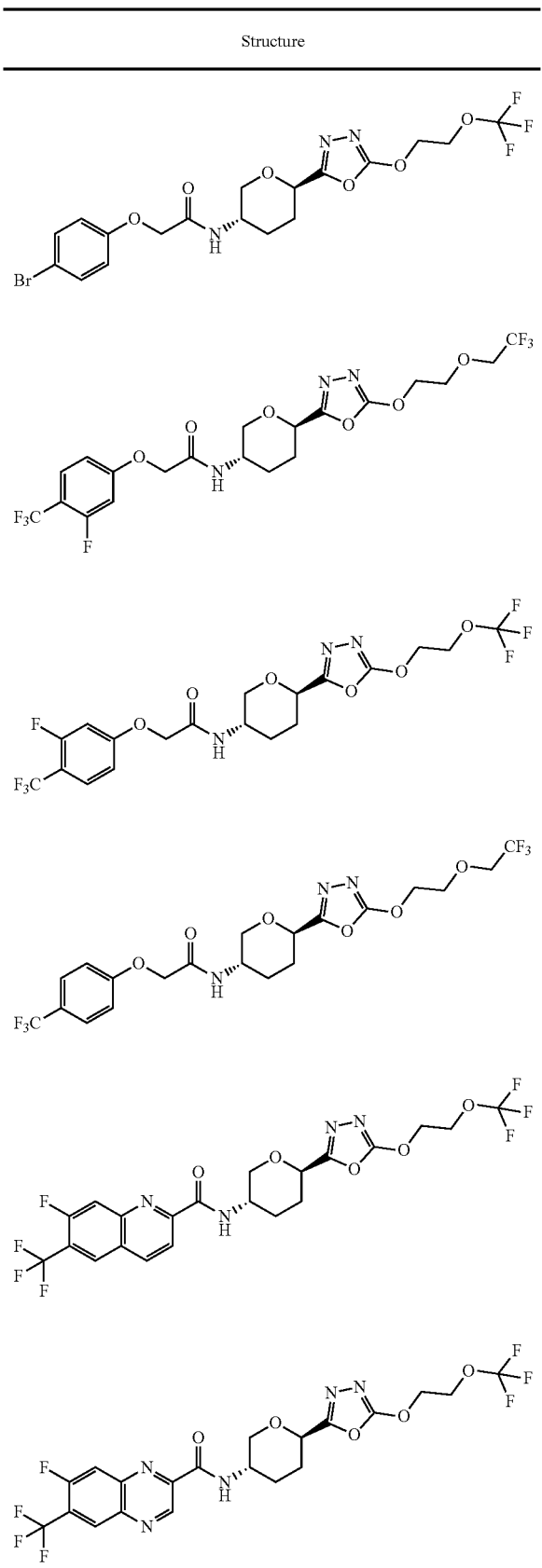
or a pharmaceutically acceptable salt, isotopically enriched analog, prodrug, stereoisomer, or a mixture of stereoisomers thereof.
In certain embodiments, provided is a compound selected from Table 1A:
TABLE 1A
| Ex. | Structure |
|---|---|
| 21 | 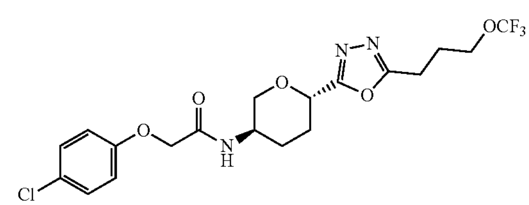 [SMILES: O=C(COc1ccc(Cl)cc1)N[C@@H]1CC[C@@H](c2nnc(CCCOC(F)(F)F)o2)OC1] |
| 22 | 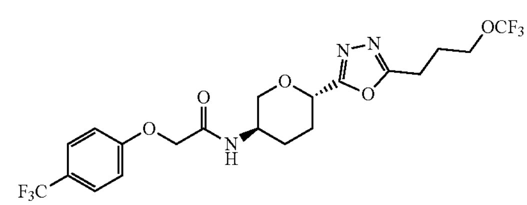 [SMILES: O=C(COc1ccc(C(F)(F)F)cc1)N[C@@H]1CC[C@@H](c2nnc(CCCOC(F)(F)F)o2)OC1] |
or a pharmaceutically acceptable salt, isotopically enriched analog, prodrug, stereoisomer, or a mixture of stereoisomers thereof.

In certain embodiments, provided is a compound selected from Table 2A:

TABLE 2A

Structure

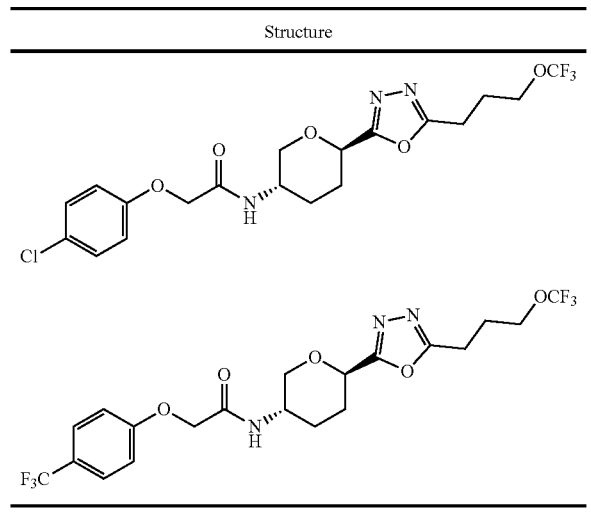

or a pharmaceutically acceptable salt, isotopically enriched analog, prodrug, stereoisomer, or a mixture of stereoisomers thereof.

3. Methods

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy, and/or veterinary applications. In some embodiments, the subject is a mammal. In certain embodiments, the subject is a human.

The term "therapeutically effective amount" or "effective amount" of a compound described herein or a pharmaceutically acceptable salt, isotopically enriched analog, stereoisomer, mixture of stereoisomers, or prodrug thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition of as described herein. The therapeutically effective amount may vary depending on the subject, and disease or condition being treated, the weight and age of the subject, the severity of the disease or condition, and the manner of administering, which can readily be determined by one of ordinary skill in the art.

The methods described herein may be applied to cell populations in vivo or ex vivo. "In vivo" means within a living individual, as within an animal or human. In this context, the methods described herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. In this context, the compounds and compositions described herein may be used for a variety of purposes, including therapeutic and experimental purposes. For example, the compounds and compositions described herein may be used ex vivo to determine the optimal schedule and/or dosing of administration of a compound of the present disclosure for a given indication, cell type, individual, and other parameters. Information gleaned from such use may be used for experimental purposes or in the clinic to set protocols for in vivo treatment. Other ex vivo uses for which the compounds and compositions described herein may be suited are described below or will become apparent to those skilled in the art. The selected compounds may be further characterized to examine the safety or tolerance dosage in human or non-human subjects. Such properties may be examined using commonly known methods to those skilled in the art.

In certain embodiments, the compounds disclosed herein can be used to treat cellular proliferative disorders, including both cancerous and non-cancerous cellular proliferative disorders. Treatment of cellular proliferative disorders may comprise, but is not limited to, inhibiting cellular proliferation, including rapid proliferation. It is contemplated that the compounds described herein can be used to treat any type of cancer, including, but not limited to, carcinomas, sarcomas, lymphomas, leukemias, and germ cell tumors. Exemplary cancers include, but are not limited to, adrenocortical carcinoma, anal cancer, appendix cancer, basal cell carcinoma, cholangiocarcinoma, bladder cancer, bone cancer, osteosarcoma or malignant fibrous histiocytoma, brain cancer (e.g., brain stem glioma, astrocytoma (e.g., cerebellar, cerebral, etc.), atypical teratoid/rhabdoid tumor, central nervous system embryonal tumors, malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors, etc.), breast cancer, bronchial tumors, carcinoid tumor (e.g., gastrointestinal, etc.), carcinoma of unknown primary, cervical cancer, chordoma, chronic myeloproliferative disorders, colon cancer, colorectal cancer, embryonal tumors, cancers of the central nervous system, endometrial cancer, ependymoma, esophageal cancer, Ewing family of tumors, eye cancer (e.g., intraocular melanoma, retinoblastoma, etc.), gallbladder cancer, gastric cancer, gastrointestinal tumor (e.g., carcinoid tumor, stromal tumor (gist), stromal cell tumor, etc.), germ cell tumor (e.g., extracranial, extragonadal, ovarian, etc.), gestational trophoblastic tumor, head and neck cancer, hepatocellular cancer, hypopharyngeal cancer, hypothalamic and visual pathway glioma, intraocular melanoma, islet cell tumors, Kaposi sarcoma, kidney cancer, large cell tumors, laryngeal cancer (e.g., acute lymphoblastic, acute myeloid, etc.), leukemia (e.g., myeloid, acute myeloid, acute lymphoblastic, chronic lymphocytic, chronic myelogenous, multiple myelogenous, hairy cell, etc.), lip and/or oral cavity cancer, liver cancer, lung cancer (e.g., non-small cell, small cell, etc.), lymphoma (e.g., AIDS-related, Burkitt, cutaneous Tcell, Hodgkin, non-Hodgkin, primary central nervous system, cutaneous T-cell, Waldenström macroglobulinemia, etc.), malignant fibrous histiocytoma of bone and/or osteosarcoma, medulloblastoma, medulloepithelioma, merkel cell carcinoma, mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases (e.g., myeloproliferative disorders, chronic, etc.), nasal cavity and/or paranasal sinus cancer, nasopharyngeal cancer, neuroblastoma, oral cancer; oral cavity cancer, oropharyngeal cancer; osteosarcoma and/or malignant fibrous histiocytoma of bone; ovarian cancer (e.g., ovarian epithelial cancer, ovarian germ cell tumor, ovarian low malignant potential tumor, etc.), pancreatic cancer (e.g., islet cell tumors, etc.), papillomatosis, paranasal sinus and/or nasal cavity cancer, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm/multiple myeloma, pleuropulmonary blastoma, prostate cancer, rectal cancer, renal cell cancer, transitional cell cancer, respiratory tract carcinoma involving the nut gene on chromosome 15, retinoblastoma, rhabdomyosarcoma, salivary gland cancer, sarcoma (e.g., Ewing family of tumors, Kaposi, soft tissue, uterine, etc.), Sézary syndrome, skin cancer (e.g., non-melanoma, melanoma, merkel cell, etc.), small intestine cancer, squamous cell carcinoma, squamous neck cancer with occult primary, metastatic, stomach cancer, supratentorial primitive neuroectodermal tumors, testicular cancer, throat cancer, thymoma and/or thymic carcinoma, thyroid cancer, transitional cell cancer of the renal, pelvis and/or ureter (e.g., trophoblastic tumor, unknown primary site carcinoma, urethral cancer, uterine cancer, endometrial, uterine sarcoma, etc.), vaginal cancer, visual pathway and/or hypothalamic glioma, vulvar cancer, Wilms tumor, and the like. Examples of noncancerous cellular proliferative disorders include, but are not limited to, fibroadenoma, adenoma, intraductal papilloma, nipple adenoma, adenosis, fibrocystic disease or changes of breast, plasma cell proliferative disorder (PCPD), restenosis, atherosclerosis, rheumatoid arthritis, myofibromatosis, fibrous hamartoma, granular lymphocyte proliferative disorders, benign hyperplasia of prostate, heavy chain diseases (HCDs), lymphoproliferative disorders, psoriasis, idiopathic pulmonary fibrosis, scleroderma, cirrhosis of the liver, IgA nephropathy, mesangial proliferative glomerulonephritis, membranoproliferative glomerulonephritis, hemangiomas, vascular and non-vascular intraocular proliferative disorders, and the like.

In certain embodiments, the compounds disclosed herein can be used to treat lung injury and/or lung inflammation.

In certain embodiments, the compounds disclosed herein can be used to treat cancer, pre-cancerous syndromes and diseases/injuries associated with activated unfolded protein response pathways, such as Alzheimer's disease, neuropathic pain, spinal cord injury, traumatic brain injury, ischemic stroke, stroke, Parkinson's disease, diabetes, metabolic syndrome, metabolic disorders, Huntington's disease, Creutzfeldt-Jakob Disease, fatal familial insomnia, Gerstmann-Straussler-Scheinker syndrome, and related prion diseases, amyotrophic lateral sclerosis, progressive supranuclear palsy, myocardial infarction, cardiovascular disease, inflammation, organ fibrosis, chronic and acute diseases of the liver, fatty liver disease, liver steatosis, liver fibrosis, chronic and acute diseases of the lung, lung fibrosis, chronic and acute diseases of the kidney, kidney fibrosis, chronic traumatic encephalopathy (CTE), neurodegeneration, dementias, frontotemporal dementias, tauopathies, Pick's disease, Neimann-Pick's disease, amyloidosis, cognitive impairment, atherosclerosis, ocular diseases, arrhythmias, in organ transplantation and in the transportation of organs for transplantation.

In embodiments, the compounds disclosed herein can be used to treat or lessen the severity of cancer, Alzheimer's disease, stroke, Type 1 diabetes, Parkinson disease, Huntington's disease, amyotrophic lateral sclerosis, myocardial infarction, cardiovascular disease, atherosclerosis, arrhythmias, or age-related macular degeneration.

In certain embodiments, the compounds disclosed herein can be used to treat neuropathic pain.

In certain embodiments, the compounds disclosed herein can be used to treat or lessen the severity of ocular diseases/angiogenesis. In certain embodiments, the ocular disease includes vascular leakage (e.g., edema or neovascularization for any occlusive or inflammatory retinal vascular disease, such as rubeosis irides, neovascular glaucoma, pterygium, vascularized glaucoma filtering blebs, conjunctival papilloma), choroidal neovascularization (e.g., neovascular age-related macular degeneration (AMD), myopia, prior uveitis, trauma, or idiopathic), macular edema (e.g., post surgical macular edema, macular edema secondary to uveitis including retinal and/or choroidal inflammation, macular edema secondary to diabetes, and macular edema secondary to retinovascular occlusive disease (i.e. branch and central retinal vein occlusion)), retinal neovascularization due to diabetes (e.g., retinal vein occlusion, uveitis, ocular ischemic syndrome from carotid artery disease, ophthalmic or retinal artery occlusion, sickle cell retinopathy, other ischemic or occlusive neovascular retinopathies, retinopathy of prematurity, or Eale's Disease), and genetic disorders (e.g., VonHippel-Lindau syndrome). In certain embodiments, the neovascular age-related macular degeneration is wet age-related macular degeneration. In certain embodiments, the neovascular age-related macular degeneration is dry age-related macular degeneration and the patient is characterized as being at increased risk of developing wet age-related macular degeneration.

In certain embodiments, the compounds disclosed herein can be used to treat viral infections (e.g., to prevent the initiation of viral protein synthesis). Exemplary viruses which can be treated using the compounds disclosed herein include, but are not limited to, picornaviridae (e.g., polioviruses), reoviridae (e.g., rotaviruses), togaviridae (e.g., encephalitis viruses, yellow fever virus, rubella virus, etc.), orthomyxoviridae (e.g., influenza viruses), paramyxoviridae (e.g., respiratory syncytial virus, measles virus, mumps virus, parainfluenza virus, etc.), rhabdoviridae (e.g., rabies virus), coronaviridae, bunyaviridae, flaviviridae, filoviridae, arenaviridae, bunyaviridae, and retroviridae (e.g., human T-cell lymphotropic viruses (HTLV), human immunodeficiency viruses (HIV), etc.), papovaviridae (e.g., papilloma viruses), adenoviridae (e.g., adenovirus), herpesviridae (e.g., herpes simplex viruses), and poxyiridae (e.g., variola viruses). In certain embodiments, the viral infection is caused by hepatitis B virus, hepatitis C virus, and/or HIV.

In certain embodiments, the compounds disclosed herein can be used to treat disorders associated with viral infections. Such disorders include, but are not limited to neurological symptoms (e.g., encephalitis, meningoencephalitis, paralysis, myelopathy, neuropathy, aseptic meningitis, hemiparesis, dementia, dysphagia, lack of muscular coordination, impaired vision, coma, etc.), wasting symptoms (e.g., inflammatory cell infiltration, perivascular cuffing of blood vessels, demyelination, necrosis, reactive gliosis, etc.), gastroenteritis symptoms (e.g., diarrhea, vomiting, cramps, etc.), hepatitis symptoms (nausea, vomiting, right upper quadrant pain, raised liver enzyme levels (e.g., AST, ALT, etc.), jaundice, etc.), hemorrhagic fever symptoms (e.g., headache, fever, chills body pains, diarrhea, vomiting, dizziness, confusion, abnormal behavior, pharyngitis, conjunctivitis, red face, red neck, hemorrhage, organ failure, etc.), oncogenic symptoms (e.g., sarcomas, leukemias, and the like, as well as "rare" malignancies, e.g., Kaposi's sarcoma, oral hairy leukoplasia, lymphomas, etc.), immunodeficiency symptoms (e.g., opportunistic infections, wasting, rare malignancies, neurological disease, fever, diarrhea, skin rashes, etc.), lesions (e.g., warts (e.g., common wart, flat wart, deep hyperkeratotic palmoplantar wart, superficial mosaic type palmoplantar wart, etc.)), epidermodysplasia, mucosal lesions, ulcers, and systemic symptoms (e.g., fever, chills, headache, muscle pain, bone pain, joint pain, pharyngitis, tonsillitis, sinusitis, otitis, bronchitis, pneumonia, bronchopneumonia, nausea, vomiting, increased salivation, rash, macules, lymphadenopathy, arthritis, ulcers, photosensitivity, weight loss, irritability, restlessness, anxiety, coma, death, etc.).

In certain embodiments, the compounds disclosed herein can be used to treat disorders characterized by unwanted synthesis and/or abnormal accumulation of one or more mutant and/or wild-type proteins. It is contemplated that the compounds disclosed herein that can inhibit translation initiation and thus can reduce the load on the protein-folding machinery and, accordingly, may reduce the severity of the disorder. Disorders associated with unwanted synthesis and/or abnormal accumulation of one or more mutant and/or wild-type proteins include, but are not limited to, Tay-Sachs disease, cystic fibrosis, phenylketonuria, Fabry disease, Alzheimer's disease, Huntington's disease, Parkinson's disease, frontotemporal dementia, congophilic angiopathy, prion related disorders (i.e., transmissible spongiform encephalopathies such as Creutzfeldt-Jacob disease, kuru, fatal familial insomnia, scrapie, bovine spongiform encephalopathy, etc.), and the like.

It is contemplated that the compounds and compositions disclosed herein are capable of inhibiting neuronal cell death, such as in prion disease. Generally, the method includes administering a therapeutically effective amount of a compound or composition as described herein, to a patient in need thereof.

In some embodiments, the disorder is a neurodegenerative disease. The term "neurodegenerative disease" refers to a disease or condition in which the function of a subject's nervous system becomes impaired. Examples of neurodegenerative diseases include, e.g., Alexander's disease, Alper's disease, Alzheimer's disease, amyotrophic lateral sclerosis, ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, narcolepsy, Neuroborreliosis, Parkinson's disease, Pelizaeus-Merzbacher Disease, Pick's disease, Primary lateral sclerosis, Prion diseases, Refsum's disease, Sandhoff's disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, vanishing white matter (VWM) disease, insulin resistance or Tabes dorsalis.

Other embodiments include use of the presently disclosed compounds in therapy. Some embodiments include their use in the treatment of a neurodegenerative disease.

In other embodiments, provided are the presently disclosed compounds for use in the treatment of Alzheimer's disease, Parkinson's disease, dementia, or ALS.

In other embodiments, provided is the use of the presently disclosed compounds or a pharmaceutically acceptable salt thereof, for the manufacture of a medicament for treating a neurodegenerative disease.

In other embodiments, provided is the use of the presently disclosed compounds or a pharmaceutically acceptable salt thereof, for the manufacture of a medicament for treating Alzheimer's disease, Parkinson's disease, dementia, or ALS.

In other embodiments, provided is the use of the presently disclosed compounds, or a pharmaceutically acceptable salt thereof, for the manufacture of a medicament for treating cancer.

In other embodiments, provided is the presently disclosed compounds, or pharmaceutically acceptable salt thereof, for use in therapy.

In other embodiments, provided is the presently disclosed compounds, or pharmaceutically acceptable salt thereof, for use in treating a neurodegenerative disease.

In other embodiments, provided is the presently disclosed compounds, or pharmaceutically acceptable salt thereof, for use in treating cancer.

4. Kits

Provided herein are also kits that include a compound of the disclosure, or a pharmaceutically acceptable salt, isotopically enriched analog, stereoisomer, mixture of stereoisomers, or prodrug thereof, and suitable packaging. In certain embodiments, a kit further includes instructions for use. In one aspect, a kit includes a compound of the disclosure, or a pharmaceutically acceptable salt, isotopically enriched analog, stereoisomer, mixture of stereoisomers, or prodrug thereof, and a label and/or instructions for use of the compounds in the treatment of the indications, including the diseases or conditions, described herein.

Provided herein are also articles of manufacture that include a compound described herein or a pharmaceutically acceptable salt, isotopically enriched analog, stereoisomer, mixture of stereoisomers, or prodrug thereof in a suitable container. The container may be a vial, jar, ampoule, preloaded syringe, or intravenous bag.

5. Pharmaceutical Compositions and Modes of Administration

Compounds provided herein are usually administered in the form of pharmaceutical compositions. Thus, provided herein are also pharmaceutical compositions that contain one or more of the compounds described herein a pharmaceutically acceptable salt, stereoisomer, mixture of stereoisomers, or prodrug thereof, and one or more pharmaceutically acceptable vehicles selected from carriers, adjuvants, and excipients. Suitable pharmaceutically acceptable vehicles may include, for example, inert solid diluents and fillers, diluents, including sterile aqueous solution and various organic solvents, permeation enhancers, solubilizers, and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal, and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, isotopically enriched analog, stereoisomer, mixture of stereoisomers, or prodrug thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include, e.g., lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl and propylhydroxy-benzoates; sweetening agents; and flavoring agents.

The compositions that include at least one compound described herein or a pharmaceutically acceptable salt, isotopically enriched analog, stereoisomer, mixture of stereoisomers, or prodrug thereof can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or a pharmaceutically acceptable salt, isotopically enriched analog, stereoisomer, mixture of stereoisomers, or prodrug thereof. When referring to these preformulation compositions as homogeneous, the active ingredient may be dispersed evenly throughout the composition so that the composition may be readily subdivided into equally effective unit dosage forms such as tablets, pills, and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

6. Dosing

The specific dose level of a compound of the present application for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate.

In other embodiments a dosage of between 0.5 and 60 mg/kg may be appropriate. In some embodiments, a dosage of from about 0.0001 to about 100 mg per kg of body weight per day, from about 0.001 to about 50 mg of compound per kg of body weight, or from about 0.01 to about 10 mg of compound per kg of body weight may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

7. Synthesis of the Compounds

The compounds may be prepared using the methods disclosed herein and routine modifications thereof, which will be apparent given the disclosure herein and methods well known in the art. Conventional and well-known synthetic methods may be used in addition to the teachings herein. The synthesis of typical compounds described herein may be accomplished as described in the following examples. If available, reagents and starting materials may be purchased commercially, e.g., from Sigma Aldrich or other chemical suppliers.

It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, conventional protecting groups ("PG") may be necessary to prevent certain functional groups from undergoing undesired reactions. Suitable protecting groups for various functional groups as well as suitable conditions for protecting and deprotecting particular functional groups are well known in the art. For example, numerous protecting groups are described in Wuts, P. G. M., Greene, T. W., & Greene, T. W. (2006). Greene's protective groups in organic synthesis. Hoboken, N.J., Wiley-Interscience, and references cited therein. For example, protecting groups for alcohols, such as hydroxyl, include silyl ethers (including trimethylsilyl (TMS), tert-butyldimethylsilyl (TBDMS), tri-iso-propylsilyloxymethyl (TOM), and triisopropylsilyl (TIPS) ethers), which can be removed by acid or fluoride ion, such as NaF, TBAF (tetra-n-butylammonium fluoride), HF-Py, or HF-NEt$_3$. Other protecting groups for alcohols include acetyl, removed by acid or base, benzoyl, removed by acid or base, benzyl, removed by hydrogenation, methoxyethoxymethyl ether, removed by acid, dimethoxytrityl, removed by acid, methoxymethyl ether, removed by acid, tetrahydropyranyl or tetrahydrofuranyl, removed by acid, and trityl, removed by acid. Examples of protecting groups for amines include carbobenzyloxy, removed by hydrogenolysis p-methoxybenzyl carbonyl, removed by hydrogenolysis, tert-butyloxycarbonyl, removed by concentrated strong acid (such as HCl or CF$_3$COOH), or by heating to greater than about 80° C., 9-fluorenylmethyloxycarbonyl, removed by base, such as piperidine, acetyl, removed by treatment with a base, benzoyl, removed by treatment with a base, benzyl, removed by hydrogenolysis, carbamate group, removed by acid and mild heating, p-methoxybenzyl, removed by hydrogenolysis, 3,4-dimethoxybenzyl, removed by hydrogenolysis, p-methoxyphenyl, removed by ammonium cenum(IV) nitrate, tosyl, removed by concentrated acid (such as HBr or H$_2$SO$_4$) and strong reducing agents (sodium in liquid ammonia or sodium naphthalenide), troc (trichloroethyl chloroformate), removed by Zn insertion in the presence of acetic acid, and sulfonamides (Nosyl & Nps), removed by samarium iodide or tributyltin hydride.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

General Synthesis

The following reaction shown in Scheme I illustrates a general method which can be employed for the synthesis of compounds disclosed herein. In Scheme I, z, $R^1$, $R^2$, $R^3$, $R^4$, $R^5$, ring A, ring B, $Q^1$, $Q^2$, L and $X^1$ are as defined herein, $R^{100}$ is halo, $R^{101}$ is the moiety

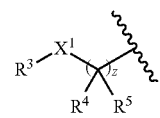

or a nitrogen protecting group, $R^{102}$ is $C_{1-6}$ alkyl, and LG is leaving group (e.g., $C_{1-6}$ alkoxy or halo). The coupling of compound of Formula 1 with the compound of Formula H-$Q^1$-L-$Q^2$-$R^2$ provide a compound of Formula 2, can be performed under standard coupling conditions (e.g., nucleophilc aromatic substitution reaction conditions). When $R^{101}$ is the moiety

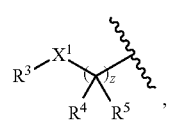

the resulting compound is of Formula I. When $R^{101}$ is a nitrogen protecting group, the method further comprises deprotecting the nitrogen atom and contacting the resulting intermediate with a compound of Formula 3, thus providing a compound of Formula I.

Scheme I

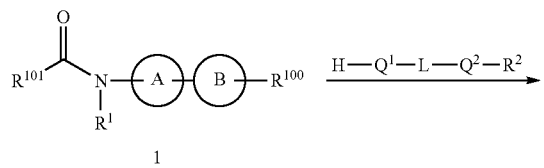

1

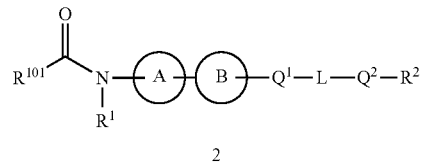

2

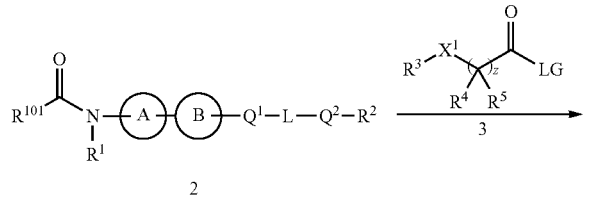

2

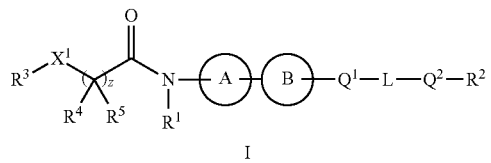

I

Accordingly, in certain embodiments, provided is a method of preparing a compound of Formula I, comprising coupling a compound of Formula 1:

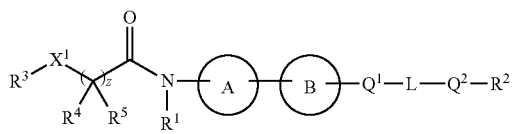

I comprising contacting a compound of Formula 1:

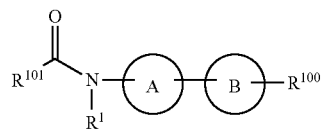

1 wherein $R^{100}$ is halo and $R^{101}$ is the moiety

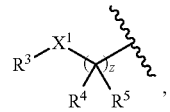

or a nitrogen protecting group; with a compound of Formula H-$Q^1$-L-$Q^2$-$R^2$, under conditions suitable to provide a compound of Formula 2:

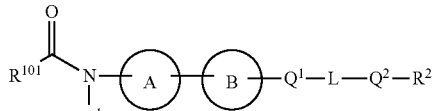

2 wherein:
a) when $R^{101}$ is the moiety

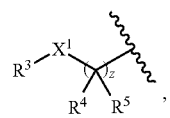

the method provides the compound of Formula I, or a salt, isotopically enriched analog, stereoisomer, or mixture of stereoisomers thereof, and b) when $R^{101}$ is a nitrogen protecting group, the method further comprises removing the nitrogen protecting group and contacting the compound of Formula 2 with a compound of Formula 3:

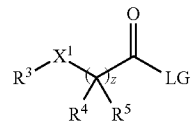

3 under conditions suitable to provide the compound of Formula I, or a salt, isotopically enriched analog, stereoisomer, or mixture of stereoisomers thereof, wherein z, $R^1$, $R^2$, $R^3$, $R^4$, $R^5$, ring A, ring B, $Q^1$, $Q^2$, L and $X^1$ are as defined herein, and LG is leaving group (e.g., —OH, $C_{1-6}$ alkoxy or halo).

The coupling of the compound of Formula 2 with the compound of Formula 3 typically employs a suitable reagent, such as a carbodiimide (e.g., N,N'-dicyclohexylcarbodiimide (DCC), N,N'-dicyclopentylcarbodiimide, N,N'-diisopropylcarbodiimide (DIC), 1-ethyl-3-(3-dimethylaminopropyl)carbodiimide (EDC), N-t-butyl-N-methylcarbodiimide (BMC), N-t-butyl-N-ethylcarbodiimide (BEC), 1,3-bis(2,2-dimethyl-1,3-dioxolan-4-ylmethyl)carbodiimide (BDDC), etc.), anhydrides (e.g., symmetric, mixed, or cyclic anhydrides), an activated ester (e.g., phenyl activated ester derivatives, p-hydroxamic activated ester, hexafluoroacetone (HFA), etc.), acylazoles (acylimidazoles using CDI, acylbenzotriazoles, etc.), acyl azides, acid halides, phosphonium salts (HOBt, PyBOP, HOAt, etc.), aminium/uronium salts (e.g., tetramethyl aminium salts, bispyrrolidino aminium salts, bispiperidino aminium salts, imidazolium uronium salts, pyrimidinium uronium salts, uronium salts derived from N,N,N'-trimethyl-N'-phenylurea, morpholino-based aminium/uronium coupling reagents, antimoniate uronium salts, etc.), an organophosphorus reagent (e.g., phosphinic and phosphoric acid derivatives, such as propylphosphonic anhydride), organosulfur reagents (e.g., sulfonic acid derivatives), a triazine coupling reagent (e.g., 2-chloro-4,6-dimethoxy-1,3,5-triazine, 4-(4,6-dimethoxy-1,3,5-triazin-2-yl)-4 methylmorpholinium chloride, 4-(4,6-dimethoxy-1,3,5-triazin-2-yl)-4 methylmorpholinium tetrafluoroborate, etc.), pyridinium coupling reagents (e.g., Mukaiyama's reagent, pyridinium tetrafluoroborate coupling reagents, etc.), and the like (see, e.g., El-Faham, et al. Chem. Rev., 2011, 111(11): 6557-6602; Han, et al. Tetrahedron, 2004, 60:2447-2467).

The following reaction shown in Scheme II illustrates exemplary general methods which can be employed for the synthesis of various B rings described herein, which methods can be utilized to prepare various compounds of Formula 1, which can be used in the methods described herein, e.g., Scheme I, to provide compounds of Formula I. In Scheme II, $R^1$ and ring A are as defined herein and $R^{101}$ is the moiety

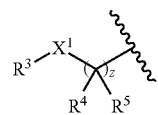

or a nitrogen protecting group. In Scheme II, compounds of Formula I where ring B is isoxazolyl can be prepared from the corresponding alkyne as in compounds of Formula 1-a. Compounds of Formula I where ring B is oxadiazolyl can be prepared from the corresponding ester (e.g., methyl ester) as in compounds of Formula 1-b. Compounds of Formula I where ring B is oxadiazolyl can be prepared from the corresponding hydrazinecarbonyl as in compounds of Formula 1-c, via the corresponding ester (e.g., methyl ester) as in compounds of Formula 1-b. Compounds of Formula I where ring B is oxadiazolyl can be prepared from the corresponding cyano-substituted intermediate as in compounds of Formula 1-d. Compounds of Formula I where ring B is oxazolyl can be prepared from the corresponding alpha-halo ester as in compounds of Formula 1-e. Alternatively, compounds of Formula I where ring B is isoxazolyl can be prepared from the corresponding methyl oxopropanoate as in compounds of Formula 1-f.

Scheme II

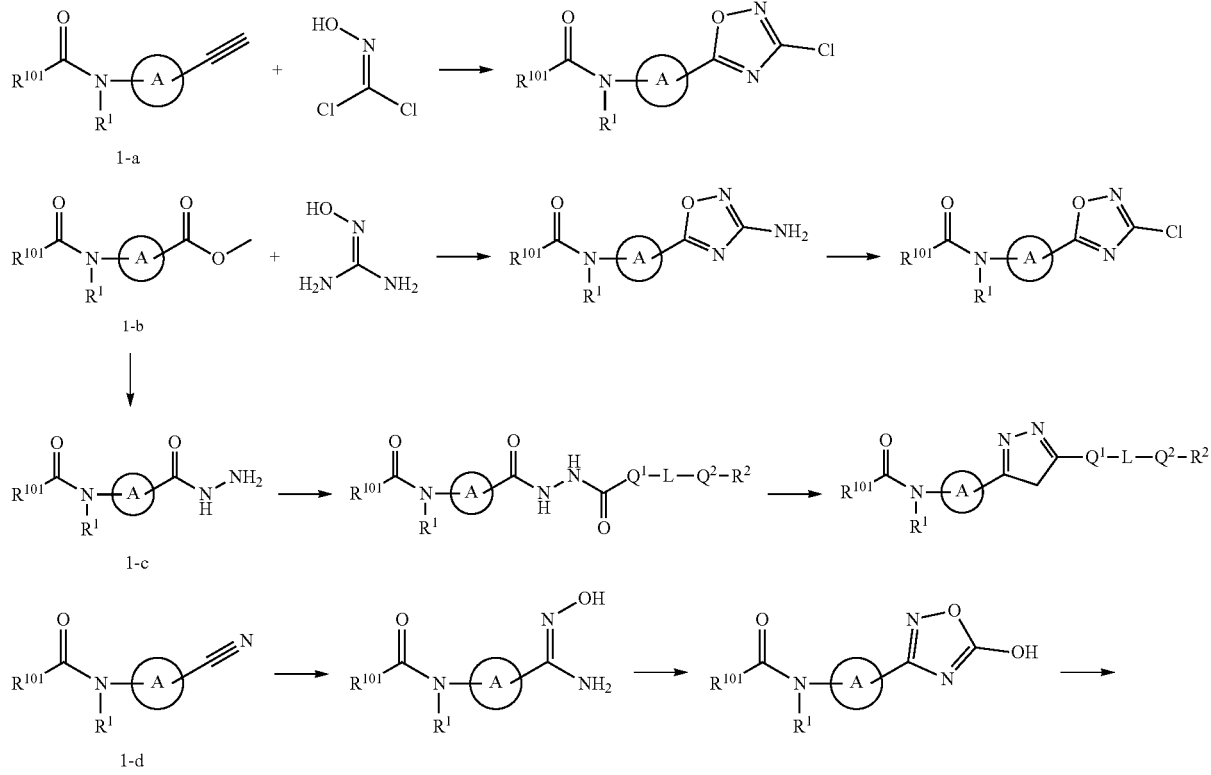

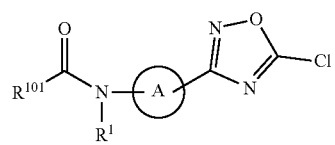

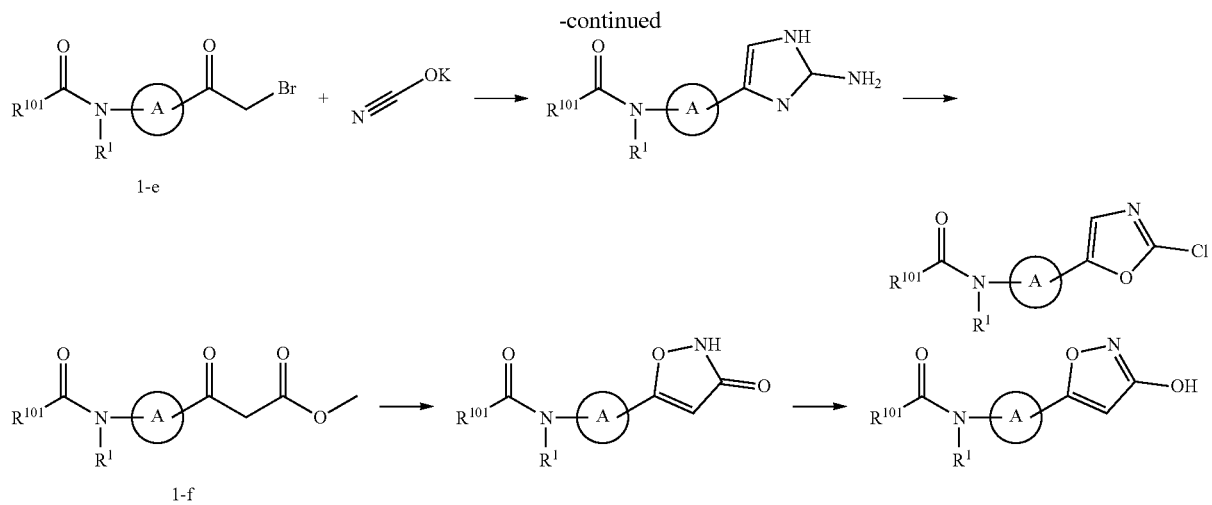

Appropriate starting materials and reagents (i.e., diamines, esters, and acids) can be purchased or prepared by methods known to one of skill in the art.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

General Experimental Methods

All solvents used were commercially available and were used without further purification. Reactions were typically run using anhydrous solvents under an inert atmosphere of nitrogen.

NMR Spectroscopy: $^1H$ Nuclear magnetic resonance (NMR) spectroscopy was carried out using a Bruker Avance III equipped with a BBFO 300 MHz probe operating at 300 MHz or one of the following instruments: a Bruker Avance 400 instrument equipped with probe DUAL 400 MHz S1, a Bruker Avance 400 instrument equipped with probe 6 S1 400 MHz 5 mm $^1H$-$^{13}C$ ID, a Bruker Avance III 400 instrument with nanobay equipped with probe Broadband BBFO 5 mm direct, a Bruker Mercury Plus 400 NMR spectrometer equipped with a Bruker 400 BBO probe with all operating at 400 MHz. All deuterated solvents contained typically 0.03% to 0.05% v/v tetramethylsilane, which was used as the reference signal (set at δ 0.00 for both $^1H$ and $^{13}C$). In certain cases, $^1H$ Nuclear magnetic resonance (NMR) spectroscopy was carried out using a Bruker Advance 400 instrument operating at 400 MHz using the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; br, broad.

Thin Layer Chromatography: Where thin layer chromatography (TLC) has been used it refers to silica gel TLC using silica gel F254 (Merck) plates, Rf is the distance travelled by the compound divided by the distance travelled by the solvent on a TLC plate. Column chromatography was performed using an automatic flash chromatography system over silica gel cartridges or in the case of reverse phase chromatography over C18 cartridges. Alternatively, thin layer chromatography (TLC) was performed on Alugram® (Silica gel 60 F254) from Mancherey-Nagel and UV was typically used to visualize the spots. Additional visualization methods were also employed in some cases. In these cases the TLC plate was developed with iodine (generated by adding approximately 1 g of $I_2$ to 10 g silica gel and thoroughly mixing), ninhydrin (available commercially from Aldrich), or Magic Stain (generated by thoroughly mixing 25 g $(NH_4)_6Mo_7O_{24} \cdot 4H_2O$, 5 g $(NH_4)_2Ce(IV)(NO_3)_6$ in 450 mL water and 50 mL concentrated $H_2SO_4$) to visualize the compound.

Liquid Chromatography-Mass Spectrometry and HPLC Analysis: HPLC analysis was performed on Shimadzu 20AB HPLC system with a photodiode array detector and Luna-C18(2) 2.0×50 mm, 5 μm column at a flow rate of 1.2 mL/min with a gradient solvent Mobile phase A (MPA, $H_2O$+0.037% (v/v) TFA): Mobile phase B (MPB, ACN+ 0.018% (v/v) TFA) (0.01 min, 10% MPB; 4 min, 80% MPB; 4.9 min, 80% MPB; 4.92 min, 10% MPB; 5.5 min, 10% MPB). LCMS was detected under 220 and 254 nm or used evaporative light scattering (ELSD) detection as well as positive electrospray ionization (MS). Semi-preparative HPLC was performed by either acidic or neutral conditions. Acidic: Luna C18 100×30 mm, 5 μm; MPA: HCl/ $H_2O$=0.04%, or formic acid/$H_2O$=0.2% (v/v); MPB: ACN. Neutral: Waters Xbridge 150×25, 5 μm; MPA: 10 mM $NH_4HCO_3$ in $H_2O$; MPB: ACN. Gradient for both conditions: 10% of MPB to 80% of MPB within 12 min at a flow rate of 20 mL/min, then 100% MPB over 2 min, 10% MPB over 2 min, UV detector. SFC analysis was performed on Thar analytical SFC system with a UV/Vis detector and series of chiral columns including AD-3, AS-H, OJ-3, OD-3, AY-3 and IC-3, 4.6×100 mm, 3 μm column at a flow rate of 4 mL/min with a gradient solvent Mobile phase A (MPA, $CO_2$): Mobile phase B (MPB, MeOH+0.05% (v/v) IPAm) (0.01 min, 10% MPB; 3 min, 40% MPB; 3.5 min, 40% MPB; 3.56-5 min, 10% MPB). SFC preparative was performed on Thar 80 preparative SFC system with a UV/Vis detector and series of chiral preparative columns including AD-H, AS-H, OJ-H, OD-H, AY-H and IC-H, 30×250 mm, 5 um column at a flow rate of 65 mL/min with a gradient solvent Mobile phase A (MPA, $CO_2$): Mobile phase B (MPB, MeOH+0.1% (v/v) $NH_3H_2O$) (0.01 min, 10% MPB; 5 min, 40% MPB; 6 min, 40% MPB; 6.1-10 min, 10% MPB). LC-MS data were also collected using an UPLC-MS Acquity™ system equipped with PDA detector and coupled to a Waters single quadrupole mass spectrometer operating in alternated positive and negative electrospray ionization mode. The column used was a Cortecs UPLC C18, 1.6 μm, 2.1×50 mm. A linear gradient was applied, starting at 95% A (A: 0.1% formic acid in water) and ending at 95% B (B: 0.1% formic acid in MeCN) over 2.0 min with a total run time of 2.5 min. The column temperature was at 40° C. with the flow rate of 0.8 mL/min.

General procedure A, T3P coupling: To a flask containing amine (1 eq), and carboxylic acid (1.5 eq) in DMF or EtOAc (0.1 M-0.2 M) were added either N-methylimidazole, diisopropylethylamine, or triethylamine (3.0-5.0 eq) followed by T3P solution (1.5-3.0 eq., 50% in EtOAc). The resulting reaction mixture was stirred at rt for 4 h, at which point 1M NaOH solution was added followed by EtOAc. The layers were separated, and the aqueous layer was extracted with EtOAc (3×). The combined organic layers were dried over anhydrous $MgSO_4$, filtered and concentrated under reduced pressure. The crude reaction mixture was purified employing silica flash chromatography or reverse-phase HPLC to provide the desired product.

General procedure B, Hydrazide Formation: To a suspension of the methyl ester (1 eq) in EtOH (0.25-0.1M) was added hydrazine hydrate (3-5 eq) and the reaction mixture was heated at 90° C. overnight. The reaction mixture was cooled to rt often causing the product to crystallize out of solution. This solid was collected by removal of the supernatant. If the product did not crystallize, the solution was concentrated, and the crude product was sufficiently pure to use in subsequent steps.

Intermediate 1: tert-butyl ((3R,6S)-6-(5-(2-(trifluoromethoxy)ethoxy)-1,3,4-oxadiazol-2-yl)tetrahydro-2H-pyran-3-yl)carbamate tert-butyl ((3R,6S)-6-(5-mercapto-1,3,4-oxadiazol-2-yl)tetrahydro-2H-pyran-3-yl)carbamate: To a mixture of tert-butyl ((3R,6S)-6-(hydrazinecarbonyl)tetrahydro-2H-pyran-3-yl)carbamate (1.0 g, 3.86 mmol) in MeOH (15 mL) was added KOH (260 mg, 4.63 mmol), the mixture was stirred at 25° C. for 0.5 h, $CS_2$ (587 mg, 7.71 mmol) was added and the mixture was stirred at 80° C. for 16 h. The reaction mixture was concentrated under reduced pressure to give a residue and the residue was redissolved with $H_2O$ (50 mL), and then adjusted pH=3, filtered and the filtered cake was concentrated under reduced pressure to give the desired product. LCMS: m/z=246.1 $[M-55]^+$. $^1H$ NMR (400 MHz, $CDCl_3$) δ=4.58-4.41 (m, 2H), 4.15 (br d, J=7.8 Hz, 1H), 3.76 (br d, J=18.3 Hz, 1H), 3.25 (br t, J=10.1 Hz, 1H), 2.27-1.95 (m, 3H), 1.46 (br s, 10H).

tert-butyl ((3R,6S)-6-(5-(methylthio)-1,3,4-oxadiazol-2-yl)tetrahydro-2H-pyran-3-yl)carbamate: To a mixture of tert-butyl ((3R,6S)-6-(5-mercapto-1,3,4-oxadiazol-2-yl)tetrahydro-2H-pyran-3-yl)carbamate (3.7 g, 12.28 mmol) in DMF (60 mL) was added $K_2CO_3$ (3.39 g, 24.56 mmol) and MeI (3.49 g, 24.56 mmol), and the mixture was stirred at 20° C. for 12 h. The reaction mixture was diluted with $H_2O$ (50 mL), and extracted with EtOAc (3×30 mL). The combined organic layers were washed with brine (50 mL), dried over anhydrous $Na_2SO_4$, filtered and concentrated under reduced pressure to give a residue, which was purified by silica gel column chromatography (PE:EtOAc=1:0 to 0:1) to afford the desired product. LCMS: m/z=260.1 $[M-55]^+$. $^1H$ NMR (400 MHz, $CDCl_3$) δ=4.62 (br dd, J=2.8, 9.5 Hz, 1H), 4.49 (br s, 1H), 4.14 (br dd, J=3.4, 10.9 Hz, 1H), 3.81-3.69 (m, 1H), 3.26 (br t, J=10.0 Hz, 1H), 2.72 (s, 3H), 2.27-2.00 (m, 3H), 1.56-1.39 (m, 10H).

tert-butyl ((3R,6S)-6-(5-(methylsulfonyl)-1,3,4-oxadiazol-2-yl)tetrahydro-2H-pyran-3-yl)carbamate: To a mixture of tert-butyl ((3R,6S)-6-(5-(methylthio)-1,3,4-oxadiazol-2-yl)tetrahydro-2H-pyran-3-yl)carbamate (2.6 g, 8.24 mmol) in DCM (40 mL) was added m-CPBA (7.11 g, 32.98 mmol, 80% purity) at 25° C. under $N_2$, and the mixture was stirred at 25° C. for 16 h. The reaction mixture was diluted with $Na_2S_2O_3$ solution (3×40 mL), was washed with $NaHCO_3$ solution (3×40 mL), and extracted with DCM (3×30 mL). The combined organic layers were washed with brine (30 mL), dried over anhydrous $Na_2SO_4$, filtered and concentrated under reduced pressure to give the desired product. LCMS: m/z=292.0 $[M-55]^+$. $^1H$ NMR (400 MHz, $CDCl_3$) δ=4.74 (dd, J=2.8, 10.2 Hz, 1H), 4.46 (br s, 1H), 4.19 (br dd, J=3.6, 10.7 Hz, 1H), 3.77 (br d, J=6.2 Hz, 1H), 3.48 (s, 3H), 3.29 (br t, J=10.0 Hz, 1H), 2.31-2.05 (m, 3H), 1.63-1.38 (m, 10H).

tert-butyl ((3R,6S)-6-(5-(2-(trifluoromethoxy)ethoxy)-1, 3,4-oxadiazol-2-yl)tetrahydro-2H-pyran-3-yl)carbamate: To a solution of 2-(trifluoromethoxy)ethanol (7.49 g, 2.88 mmol, 5% solution in THF) was added NaH (138 mg, 3.45 mmol, 60% in mineral oil), and the mixture was stirred at 0° C. for 0.5 h under $N_2$. Then tert-butyl ((3R,6S)-6-(5-(methylsulfonyl)-1,3,4-oxadiazol-2-yl)tetrahydro-2H-pyran-3-yl) carbamate (1.0 g, 2.88 mmol) was added, and the mixture was stirred at 25° C. for 2 h. The reaction mixture was diluted with $NH_4Cl$ (20 mL), and extracted with EtOAc (3×20 mL). The combined organic layers were washed with brine (20 mL), dried over anhydrous $Na_2SO_4$, and concentrated under reduced pressure to give a residue, which was purified by silica gel column chromatography (PE: EtOAc=1:0 to 1:1) to deliver the desired product. LCMS: m/z=342.1 $[M-55]^+$. $^1H$ NMR (400 MHz, $CDCl_3$) δ=4.73-4.67 (m, 2H), 4.51 (m, 2H), 4.37-4.31 (m, 2H), 4.17-4.13 (m, 1H), 3.72 (br s, 1H), 3.24 (br t, J=10.1 Hz, 1H), 2.28-2.00 (m, 3H), 1.44 (s, 10H).

Example 1: 2-(4-chlorophenoxy)-N-((3R,6S)-6-(5-(2-(trifluoromethoxy)ethoxy)-1,3,4-oxadiazol-2-yl) tetrahydro-2H-pyran-3-yl)acetamide

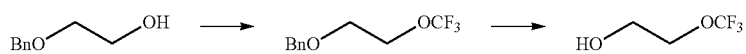

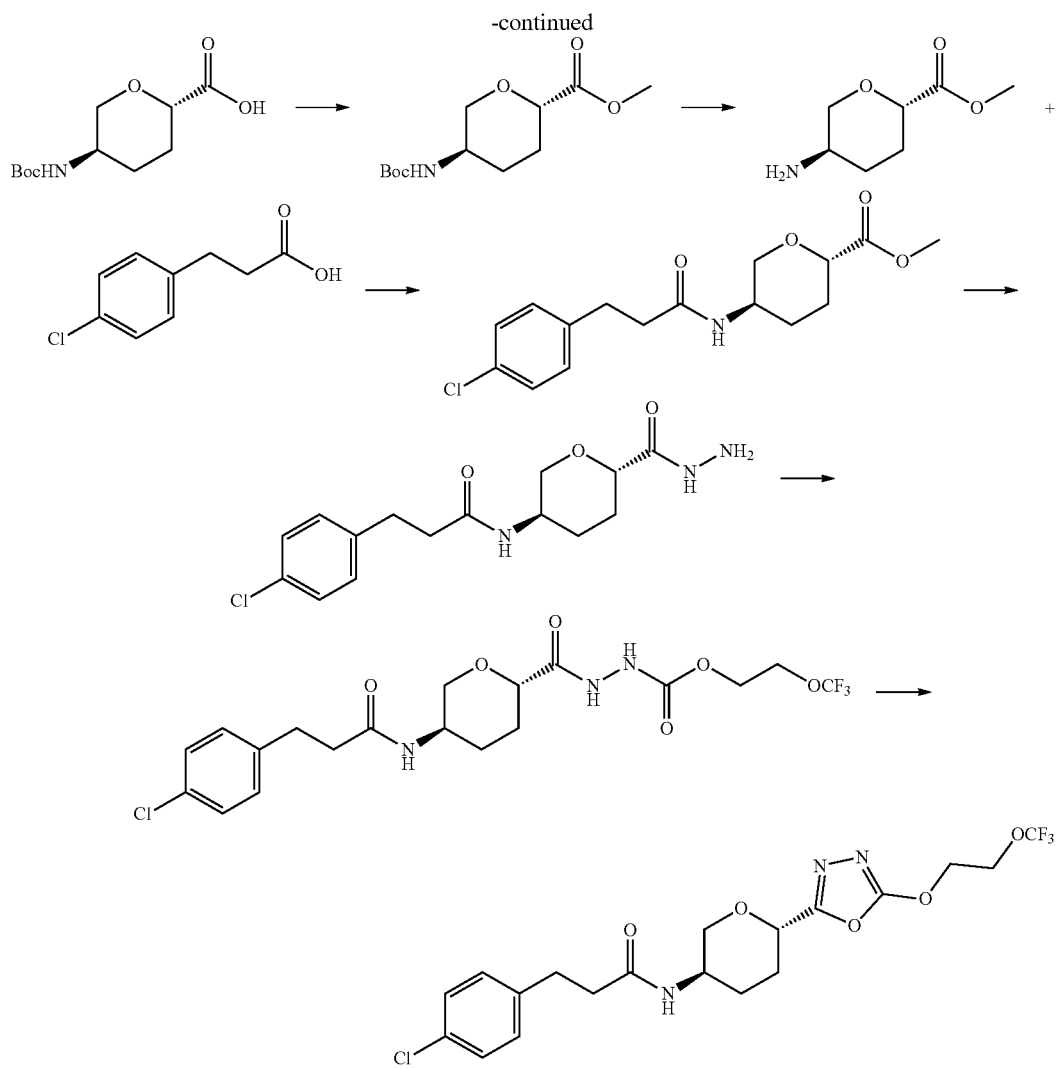

((2-(trifluoromethoxy)ethoxy)methyl)benzene: To a mixture of AgOTf (50.7 g, 197.1 mmol) in EtOAc (380 mL) under a nitrogen atmosphere were added 1-(chloromethyl)-4-fluoro-1,4-diazoniabicyclo[2.2.2]octane ditetrafluoroborate (52.4 g, 147.8 mmol), KF (17.2 g, 295.7 mmol), and 2-benzyloxyethanol (15.0 g, 98.6 mmol) in light resistant container followed by the addition of 2-fluoropyridine (16.9 mL, 197.1 mmol) and trimethyl(trifluoromethyl)silane (28.0 g, 197.1 mmol). The reaction mixture was stirred at 30° C. for 16 h. The reaction mixture was filtered through a pad of celite to give filtrate that was concentrated under reduced pressure. The crude residue was purified by silica gel column chromatography to give the desired product. $^1$H-NMR (400 MHz, CDCl$_3$): δ 7.40-7.28 (m, 5H), 4.60 (s, 2H), 4.16-4.10 (m, 2H), 3.74-3.67 (m, 2H).

2-(trifluoromethoxy)ethanol: To a suspension of palladium (500 mg, 10% purity on carbon) in EtOAc (10 mL) was added ((2-(trifluoromethoxy)ethoxy)methyl)benzene (2.0 g, 9.08 mmol). The reaction mixture was stirred at 35° C. for 24 h under H$_2$ (50 psi). The reaction mixture was filtered through celite to give filtrate that was concentrated under reduced pressure. The crude residue was used directly. $^1$H-NMR (400 MHz, CDCl$_3$): δ 4.00-3.96 (m, 2H), 3.76 (t, J=4.5 Hz, 2H).

methyl (2S,5R)-5-(tert-butoxycarbonylamino)tetrahydropyran-2-carboxylate: To a mixture of (2S,5R)-5-(tert-butoxycarbonylamino)tetrahydropyran-2-carboxylic acid (245 mg, 1.00 mmol) in DCM (4.0 mL) was added (trimethylsilyl)diazomethane (1.00 mL, 2.00 mmol, 2 M in hexanes) dropwise. The reaction mixture was stirred at 23° C. for 1 h and then concentrated under reduced pressure. The crude residue was used directly.

methyl (2R,5S)-5-aminotetrahydropyran-2-carboxylate: To a mixture of methyl (2R,5S)-5-(tert-butoxycarbonylamino)tetrahydropyran-2-carboxylate (1.05 g, 4.05 mmol) in DCM (13 mL) at 0° C. was added trifluoroacetic acid (3.1 mL, 40.5 mmol). The reaction mixture was stirred at 23° C. for 4 h and then the volatiles were removed under reduced pressure. The residue was then diluted with DCM (30 mL) and poured onto sat. aq. NaHCO$_3$ (50 mL). The organics were separated and the aqueous was extracted with using a 3:1 mixture of DCM:i-PrOH (3×30 mL). The combined organics were dried of anhydrous MgSO$_4$, filtered, and concentrated under reduced pressure. The residue was used directly. LCMS: m/z=160.2 [M+H]$^+$.

methyl (2S,5R)-5-[[2-(4-chlorophenoxy)acetyl]amino]tetrahydropyran-2-carboxylate: Prepared using General Procedure A employing methyl (2S,5R)-5-aminotetrahydropyran-2-carboxylate (644 mg, 4.05 mmol), 2-(4-chlorophenoxy)acetic acid (906 mg, 4.85 mmol), Et₃N (2.82 mL, 20.2 mmol), and T3P solution (7.23 mL, 12.1 mmol, 50% in EtOAc) in EtOAc (10.1 mL). The crude residue was purified by silica gel column chromatography to give the desired product. LCMS: m/z=328.3 [M+H]⁺.

2-(4-chlorophenoxy)-N-((3R,6S)-6-(hydrazinecarbonyl)tetrahydropyran-3-yl)acetamide: Prepared using General Procedure B employing methyl (2S,5R)-5-[[2-(4-chlorophenoxy)acetyl]amino]tetrahydropyran-2-carboxylate (622 mg, 1.9 mmol) and hydrazine hydrate in EtOH (12.7 mL). The reaction mixture was concentrated under reduced pressure and the crude residue was used directly. LCMS: m/z=328.3 [M+H]⁺.

2-(trifluoromethoxy)ethyl 2-((2S,5R)-5-(2-(4-chlorophenoxy)acetamido)tetrahydro-2H-pyran-2-carbonyl)hydrazinecarboxylate: To a solution of 2-(trifluoromethoxy)ethanol (100 mg, 0.76 mmol) and triphosgene (46 mg, 0.15 mmol) in THF (2.0 mL) at 0° C. was added pyridine (91 mg, 1.15 mmol) dropwise. The reaction mixture was stirred at 20° C. for 1 h and then 2-(4-chlorophenoxy)-N-((3R,6S)-6-(hydrazinecarbonyl)tetrahydro-2H-pyran-3-yl)acetamide (126 mg, 0.38 mmol) was added. The resultant mixture was stirred at 20° C. for a further 15 h. The reaction mixture quenched by the addition of H2O (10 mL) and extracted with EtOAc (2×5 mL). The combined organics were washed with brine (5 mL), dried over anhydrous Na₂SO₄, filtered, and concentrated under reduced pressure. The crude residue was purified employing reverse-phase HPLC to give the desired product. LCMS: m/z=484.1 [M+H]⁺.

2-(4-chlorophenoxy)-N-((3R,6S)-6-(5-(2-(trifluoromethoxy)ethoxy)-1,3,4-oxadiazol-2-yl)tetrahydro-2H-pyran-3-yl)acetamide: To a solution of 2-(trifluoromethoxy)ethyl 2-((2S,5R)-5-(2-(4-chlorophenoxy)acetamido)tetrahydro-2H-pyran-2-carbonyl)hydrazinecarboxylate (50 mg, 0.10 mmol) in MeCN (2.0 mL) was added p-TsCl (79 mg, 0.41 mmol) and Cs₂CO₃ (202 mg, 0.62 mmol). The reaction mixture was stirred at 15° C. for 16 h. The reaction mixture was poured onto ice-water (15 mL) and the aqueous was extracted with EtOAc (3×5 mL). The organic layers were washed with brine (5 mL), dried over anhydrous Na₂SO₄, filtered, and concentrated under reduced pressure. The crude residue was purified employing reverse-phase HPLC to give the desired product. LCMS: m/z=466.1 [M+H]⁺. ¹H-NMR (400 MHz, CDCl₃): δ 7.33-7.28 (m, 2H), 6.90-6.85 (m, 2H), 6.46 (br d, J=7.7 Hz, 1H), 4.75-4.69 (m, 2H), 4.62-4.57 (m, 1H), 4.47 (s, 2H), 4.37-4.32 (m, 2H), 4.22-4.10 (m, 2H), 3.41-3.34 (m, 1H), 2.31-2.21 (m, 1H), 2.16-2.06 (m, 2H), 1.72-1.62 (in, 1H).

Examples 2-5

The following compounds were, or can be, made via similar procedures as those described above.

| Ex. | Structure | LCMS m/z ([M + H]⁺) |
|---|---|---|
| 2 | (structure) | 500.3 |
| 3 | (structure) | 466.1 |
| 4 | (structure) | 482.2 |

| Ex. | Structure | LCMS m/z ([M + H]⁺) |
|---|---|---|
| 5 | 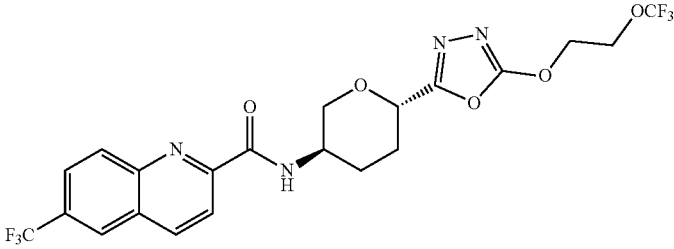 [SMILES: O=C(N[C@@H]1CC[C@@H](c2nnc(OCCOC(F)(F)F)o2)OC1)c1ccc2cc(C(F)(F)F)ccc2n1] | 521.5 |

Example 6: N-[(3R,6S)-6-[5-[2-(trifluoromethoxy)ethoxy]-1,3,4-oxadiazol-2-yl]tetrahydropyran-3-yl]-6-(trifluoromethyl)quinoxaline-2-carboxamide

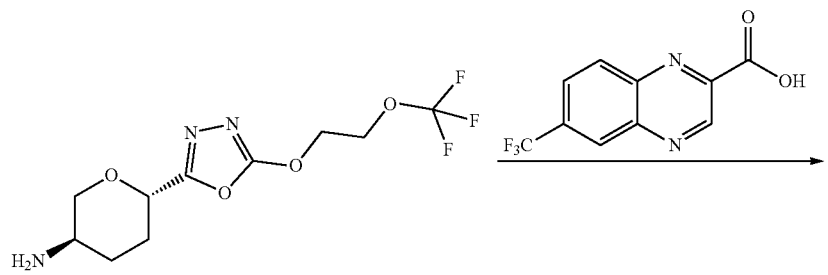

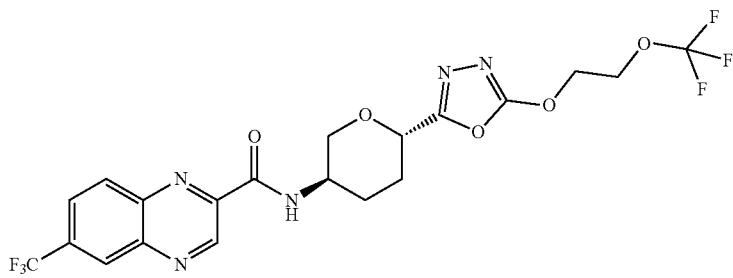

N-[(3R,6S)-6-[5-[2-(trifluoromethoxy)ethoxy]-1,3,4-oxadiazol-2-yl]tetrahydropyran-3-yl]-6-(trifluoromethyl)quinoxaline-2-carboxamide was prepared employing General Procedure A employing (3R,6S)-6-(5-(2-(trifluoromethoxy)ethoxy)-1,3,4-oxadiazol-2-yl)tetrahydro-2H-pyran-3-amine (50 mg, 0.122 mmol), 6-(trifluoromethyl)quinoxaline-2-carboxylic acid (35.4 mg, 0.146 mmol), NEt₃ (61.5 mg, 0.61 mmol) and T3P solution (77 mg, 0.243 mmol, 0.145 mL, 50% in EtOAc) in EtOAc (0.82 mL) at 25° C. for 16 h. The residue was purified by reverse-phase HPLC to give the desired product. LC-MS: m/z=522.2. ¹H-NMR (400 MHz; CDCl₃): δ 8.54 (s, 1H), 8.31 (d, J=8.8 Hz, 1H), 8.06 (dd, J=8.9, 2.0 Hz, 1H), 7.94 (d, J=8.4 Hz, 1H), 4.77-4.70 (m, 3H), 4.41-4.28 (m, 4H), 3.58 (dd, J=11.1, 8.8 Hz, 1H), 2.46-2.40 (m, 1H), 2.30-2.17 (m, 2H), 1.93-1.84 (m, 1H).

Examples 7-20

The following compounds were, or can be, made via similar procedures as those described above.

| Ex. | Structure | LCMS m/z ([M + H]+) |
|---|---|---|
| 7 | 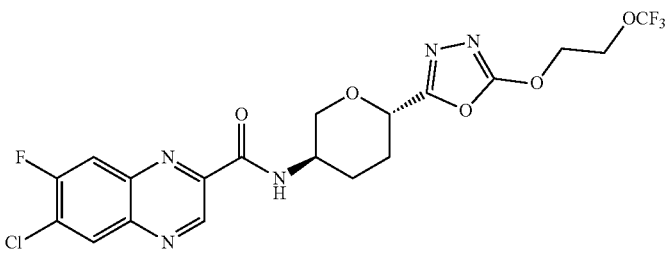 [SMILES: O=C(N[C@@H]1CC[C@@H](c2nnc(OCCOC(F)(F)F)o2)OC1)c1cnc2cc(Cl)c(F)cc2n1] | 506.1 |
| 8 | 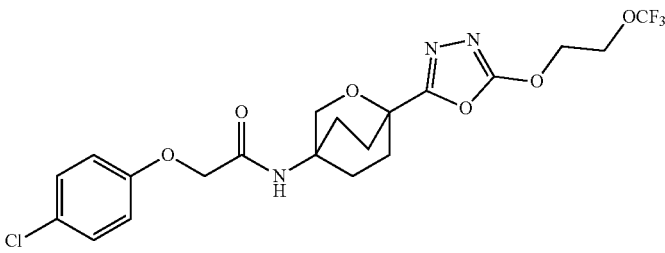 [SMILES: O=C(COc1ccc(Cl)cc1)NC12CCC(c3nnc(OCCOC(F)(F)F)o3)(CC1)OC2] | |
| 9 | 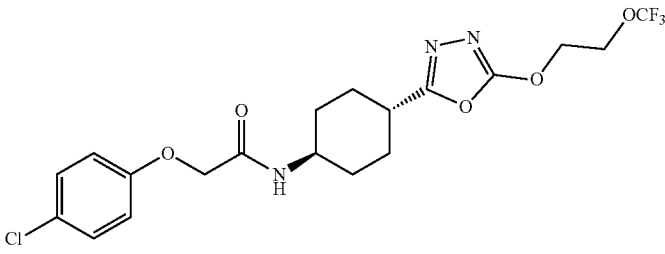 [SMILES: O=C(COc1ccc(Cl)cc1)N[C@H]1CC[C@H](c2nnc(OCCOC(F)(F)F)o2)CC1] | |
| 10 | 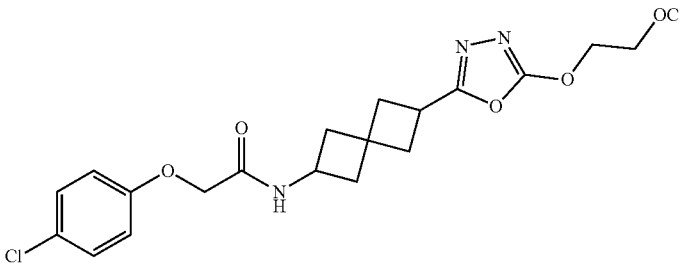 | |
| 11 | 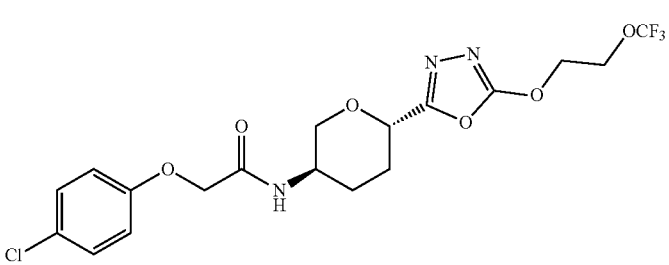 | |
| 12 | 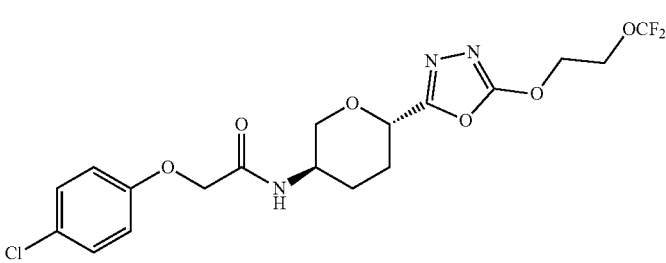 [SMILES: O=C(COc1ccc(Cl)cc1)N[C@@H]1CC[C@@H](c2nnc(OCCOC(F)(F)F)o2)OC1] | |

| Ex. | Structure | LCMS m/z ([M + H]+) |
|---|---|---|
| 13 | 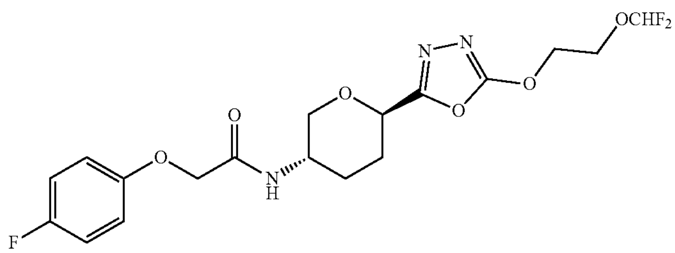 [SMILES: O=C(COc1ccc(F)cc1)N[C@H]1CC[C@H](c2nnc(OCCOC(F)F)o2)OC1] | |
| 14 | 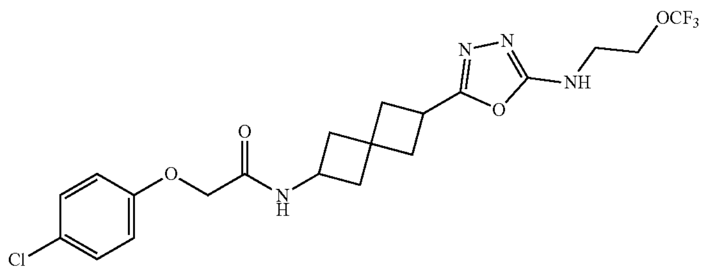 [SMILES: O=C(COc1ccc(Cl)cc1)NC1CC2(C1)CC(c1nnc(NCCOC(F)(F)F)o1)C2] | |
| 15 | 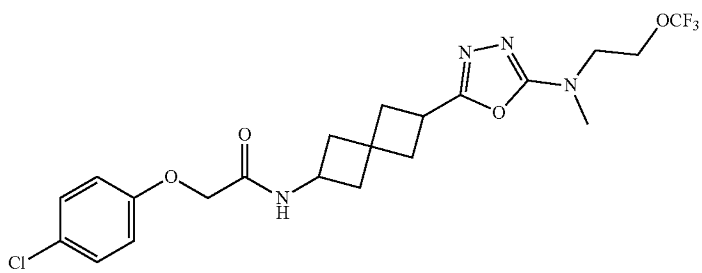 [SMILES: CN(CCOC(F)(F)F)c1nnc(C2CC3(CC(NC(=O)COc4ccc(Cl)cc4)C3)C2)o1] | |
| 16 | 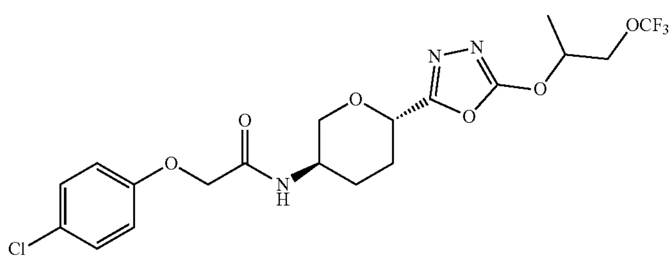 [SMILES: CC(COC(F)(F)F)Oc1nnc([C@@H]2CC[C@@H](NC(=O)COc3ccc(Cl)cc3)CO2)o1] | |
| 17 | 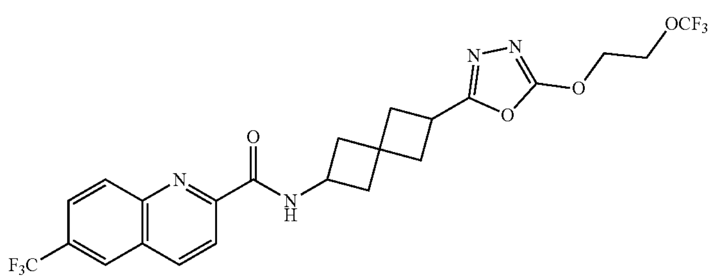 [SMILES: O=C(NC1CC2(C1)CC(c1nnc(OCCOC(F)(F)F)o1)C2)c1ccc2cc(C(F)(F)F)ccc2n1] | |

| Ex. | Structure | LCMS m/z ([M + H]+) |
|---|---|---|
| 18 | 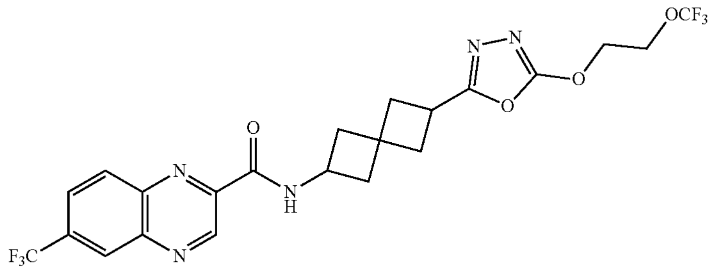 | |
| 19 | 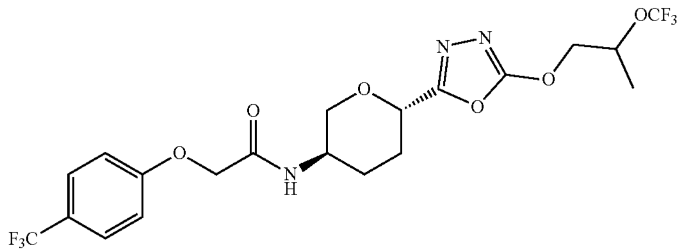 [SMILES: CC(COc1nnc([C@@H]2CC[C@@H](NC(=O)COc3ccc(C(F)(F)F)cc3)CO2)o1)OC(F)(F)F] | |
| 20 | 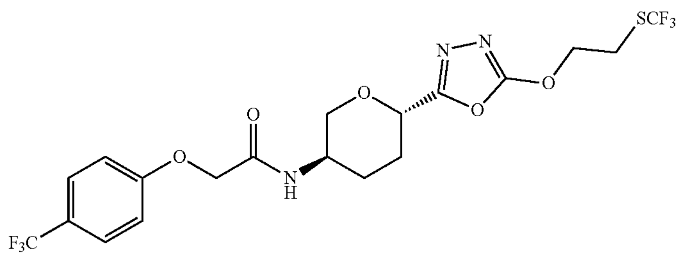 | |
Example 21: 2-(4-chlorophenoxy)-N-((3R,6S)-6-(5-(3-(trifluoromethoxy)propyl)-1,3,4-oxadiazol-2-yl)tetrahydro-2H-pyran-3-yl)acetamide
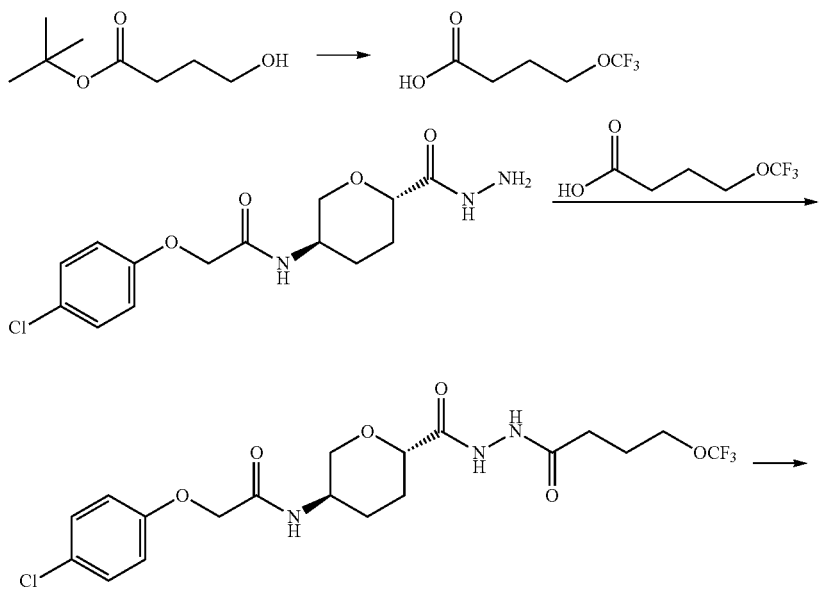

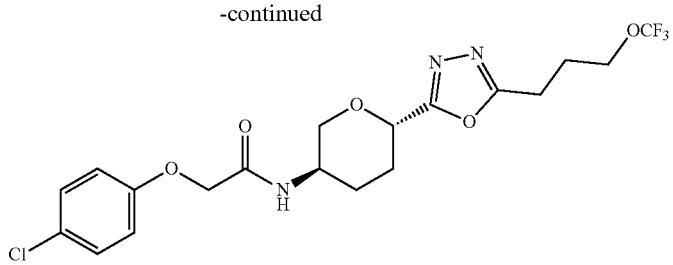

4-(trifluoromethoxy)butanoic acid: To a flask in the dark were added KF (3.55 g, 60.0 mmol), SelectFluor (15.9 g, 45.0 mmol), AgOTf (11.6 g, 45.0 mmol), and tert-butyl 4-hydroxybutanoate (2.4 g, 15.0 mmol). The mixture was then dissolved in EtOAc (73 mL) followed by the addition of 2-fluoropyridine (3.87 mL, 45.0 mmol) and trimethyl (trifluoromethyl)silane (6.65 mL, 45.0 mmol). The reaction mixture was stirred for 16 h at 23° C. and then filtered through a plug of celite and concentrated under reduced pressure. The residue was suspended in 1:1 mixture of Et$_2$O and hexanes. The suspension was filtered through a pad of silica and was concentrated under reduced pressure. The residue was dissolved in DCM (10 mL) and TFA (10 mL) at 23° C. and was stirred for 4 h. The mixture was then concentrated under reduced pressure and the residue was partitioned between Et$_2$O (25 mL) and water (25 mL). The layers were separated and the aqueous layer was extracted with Et$_2$O (3×10 mL). The combined organic layers were dried over anhydrous MgSO$_4$, filtered, and concentrated under reduced pressure. The crude residue was used directly.

2-(4-chlorophenoxy)-N-[(3S,6R)-6-[[4-(trifluoromethoxy)butanoylamino]carbamoyl]tetrahydropyran-3-yl]acetamide: 2-(4-chlorophenoxy)-N-[(3S,6R)-6-(hydrazinecarbonyl)tetrahydropyran-3-yl]acetamide (400 mg, 1.22 mmol) was suspended in MeCN (12.2 mL) and 4-(trifluoromethoxy)butanoic acid (315 mg, 1.83 mmol), NEt$_3$ (0.85 mL, 6.1 mmol), and T3P solution (1.09 mL, 3.66 mmol, 50% in EtOAc) were added. The resulting reaction mixture was stirred at 23° C. for 12 h. The reaction mixture was quenched by the addition of sat. aq. NaHCO$_3$ (5 mL) and DCM (10 mL). The layers were separated and the aqueous layer was extracted with 3:1 DCM:i-PrOH (3×10 mL). The combined organic layers were dried over anhydrous MgSO$_4$, filtered, and concentrated under reduced pressure. The crude residue was used directly.

2-(4-chlorophenoxy)-N-((3R,6S)-6-(5-(3-(trifluoromethoxy)propyl)-1,3,4-oxadiazol-2-yl)tetrahydro-2H-pyran-3-yl)acetamide: 2-(4-chlorophenoxy)-N-[(3R,6S)-6-[[4-(trifluoromethoxy)butanoylamino]carbamoyl] tetrahydropyran-3-yl]acetamide (588 mg, 1.22 mmol) was suspended in MeCN (5.5 mL) and p-TsCl (558 mg, 2.93 mmol) and Cs$_2$CO$_3$ (1.60 g, 4.88 mmol) were added. The reaction mixture was stirred overnight at 80° C. The reaction mixture was diluted with brine (10 mL) and EtOAc (10 mL). The layers were separated and the aqueous layer was extracted with EtOAc (3×10 mL). The combined organic layers were dried over anhydrous MgSO$_4$, filtered, and concentrated under reduced pressure. The crude reaction mixture was purified employing silica gel column chromatography and then further purified by reverse-phase preparative HPLC to provide the desired product. LCMS: m z=464.4 [M+H]$^+$. $^1$H-NMR (400 MHz, CDCl$_3$): δ 7.33-7.29 (m, 2H), 6.91-6.87 (m, 2H), 6.47 (d, J=8.0 Hz, 1H), 4.72 (dd, J=9.1, 3.8 Hz, 1H), 4.48-4.47 (m, 2H), 4.22-4.11 (m, 4H), 3.42-3.37 (m, 1H), 3.03 (t, J=7.4 Hz, 2H), 2.31-2.09 (m, 5H), 1.74-1.66 (m, 1H).

Example 22: N-[(3S,6R)-6-[5-[3-(trifluoromethoxy) propyl]-1,3,4-oxadiazol-2-yl]tetrahydropyran-3-yl]-2-[4-(trifluoromethyl)phenoxy]acetamide

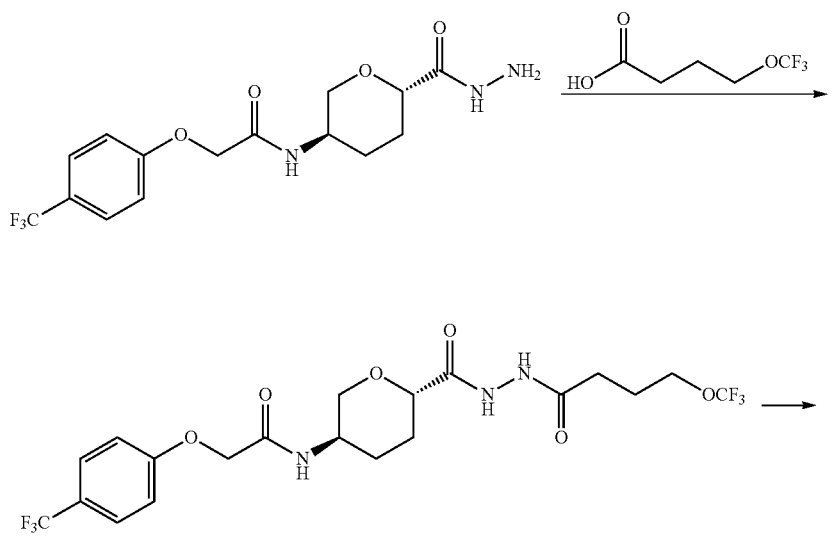

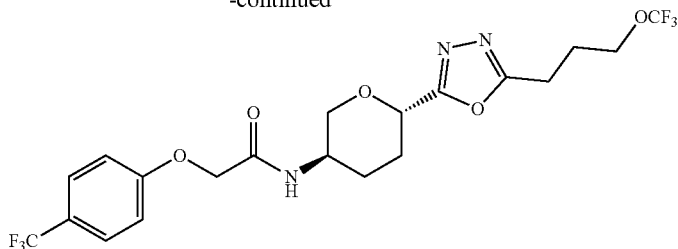

N-[(3S,6R)-6-[[4-(trifluoromethoxy)butanoylamino]carbamoyl]tetrahydropyran-3-yl]-2-[4-(trifluoromethyl)phenoxy]acetamide: N-[(3S,6R)-6-(hydrazinecarbonyl)tetrahydropyran-3-yl]-2-[4-(trifluoromethyl)phenoxy]acetamide (150 mg, 0.42 mmol) was suspended in MeCN (4.5 mL) and 4-(trifluoromethoxy)butanoic acid (107 mg, 0.62 mmol) and NEt$_3$ (0.29 mL, 2.1 mmol) and T3P solution (0.37 mL, 1.25 mmol, 50% in EtOAc) were added. The resulting reaction mixture was stirred at 23° C. for 12 h. The reaction mixture was quenched by the addition of sat. aq. NaHCO$_3$ (5 mL) and DCM (10 mL). The layers were separated and the aqueous layer was extracted with 3:1 DCM:i-PrOH (3×10 mL). The combined organic layers were dried over anhydrous MgSO$_4$, filtered, and concentrated under reduced pressure. The crude residue was purified by silica gel chromatography.

N-[(3S,6R)-6-[5-[3-(trifluoromethoxy)propyl]-1,3,4-oxadiazol-2-yl]tetrahydropyran-3-yl]-2-[4-(trifluoromethyl)phenoxy]acetamide: N-[(3S,6R)-6-[[4-(trifluoromethoxy)butanoylamino]carbamoyl]tetrahydropyran-3-yl]-2-[4-(trifluoromethyl)phenoxy]acetamide (180 mg, 0.35 mmol) was suspended in MeCN (1.7 mL) and p-TsCl (160 mg, 0.84 mmol) and Cs$_2$CO$_3$ (458 mg, 1.4 mmol) were added. The reaction mixture was stirred at 80° C. for 16 h. The reaction mixture was diluted with brine (10 mL) and EtOAc (10 mL). The layers were separated and the aqueous layer was extracted with EtOAc (3×10 mL). The combined organic layers were dried over anhydrous MgSO$_4$, filtered, and concentrated under reduced pressure. The crude reaction mixture was purified employing reverse-phase preparative HPLC to provide the desired product. LCMS: m z=498.4 [M+H]$^+$. $^1$H-NMR (400 MHz, CDCl$_3$): δ 7.63-7.61 (m, 2H), 7.03 (dd, J=9.0, 0.6 Hz, 2H), 6.49 (d, J=7.8 Hz, 1H), 4.72 (dd, J=9.1, 3.8 Hz, 1H), 4.56 (s, 2H), 4.24-4.15 (m, 2H), 4.12 (t, J=6.0 Hz, 2H), 3.44-3.38 (m, 1H), 3.03 (dd, J=8.2, 6.6 Hz, 2H), 2.32-2.10 (m, 5H), 1.76-1.66 (m, 1H).

Example 23: 6-chloro-7-fluoro-N-((3R,6S)-6-(5-(2-(trifluoromethoxy)ethoxy)-1,3,4-oxadiazol-2-yl)tetrahydro-2H-pyran-3-yl)quinoline-2-carboxamide

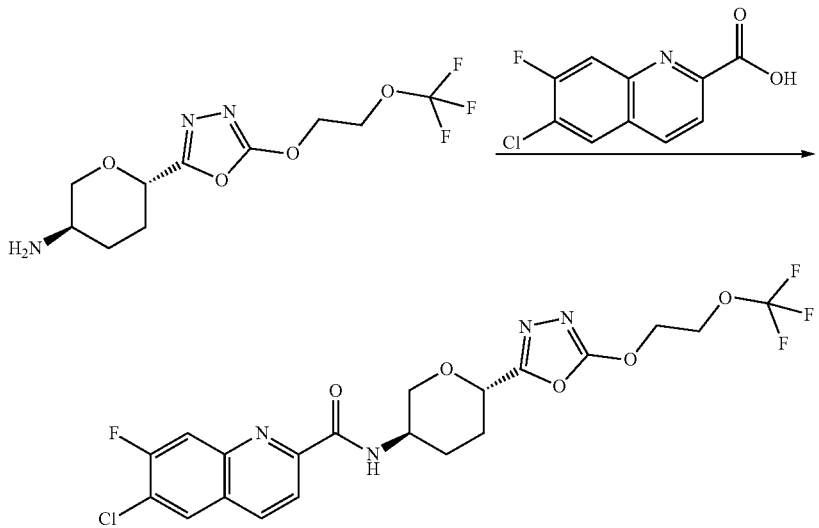

Prepared employing General Procedure A employing (3R, 6S)-6-(5-(2-(trifluoromethoxy)ethoxy)-1,3,4-oxadiazol-2-yl)tetrahydro-2H-pyran-3-amine (50 mg, 0.168 mmol), 6-chloro-7-fluoroquinoline-2-carboxylic acid (45.54 mg, 0.201 mmol), NEt$_3$ (68.09 mg, 0.672 mmol) and T3P solution (321.14 mg, 0.504 mmol, 0.300 mL, 50% in EtOAc) in EtOAc (2 mL) at 25° C. for 16 h. The residue was purified by prep-HPLC with the following conditions: column: Waters Xbridge Prep OBD C18 150*40 mm*10 μm; mobile phase: [water (10 mM NH$_4$HCO$_3$)-ACN]; B %: 45%-75%, 8 min to give the desired product. LC-MS: m/z=505.1, 507.1 [M+H]$^+$. $^1$H-NMR (400 MHz, CDCl$_3$): δ 8.33-8.24 (m, 2H), 8.10 (br d, J=7.6 Hz, 1H), 7.98 (d, J=7.7 Hz, 1H), 7.87 (d, J=9.7 Hz, 1H), 4.76-4.71 (m, 2H), 4.68 (dd, J=3.7, 9.1 Hz, 1H), 4.39-4.34 (m, 2H), 4.34-4.26 (m, 2H), 3.57-3.50 (m, 1H), 2.40 (br d, J=12.1 Hz, 1H), 2.29-2.13 (m, 2H), 1.91-1.78 (m, 1H).

Example 24: N-((3R,6S)-6-(5-(2-(trifluoromethoxy)ethoxy)-1,3,4-oxadiazol-2-yl)tetrahydro-2H-pyran-3-yl)-6-(trifluoromethyl)quinazoline-2-carboxamide

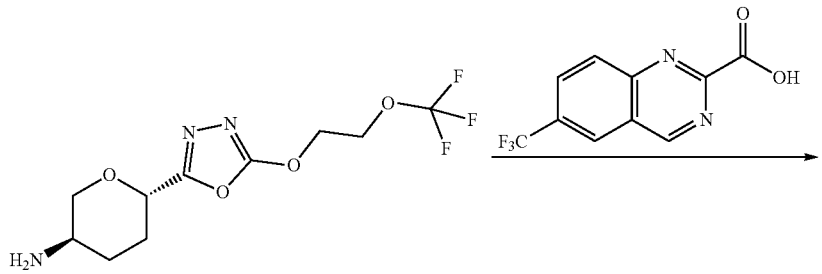

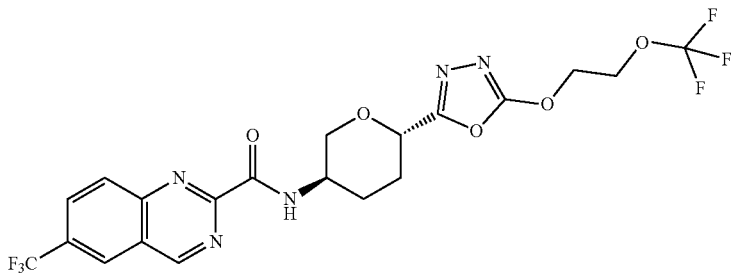

Prepared employing General Procedure A employing (3R,6S)-6-(5-(2-(trifluoromethoxy)ethoxy)-1,3,4-oxadiazol-2-yl)tetrahydro-2H-pyran-3-amine (59 mg, 0.20 mmol), 6-(trifluoromethyl)quinazoline-2-carboxylic acid (48 mg, 0.20 mmol), DIEA (103 mg, 0.79 mmol) and T3P solution (253 mg, 0.40 mmol, 0.24 mL, 50% in EtOAc) in EtOAc (5 mL) for 5 h at 20° C. The residue was purified by silica gel column chromatography (PE:EtOAc=1:0 to 0:1) to give the desired product. LC-MS: m/z=522.1 [M+H]$^+$. $^1$H NMR (400 MHz, CDCl$_3$): δ 9.64 (s, 1H), 8.43-8.36 (m, 2H), 8.27-8.16 (m, 2H), 4.78-4.61 (m, 3H), 4.44-4.27 (m, 4H), 3.54 (dd, J=8.9, 11.1 Hz, 1H), 2.47-2.36 (m, 1H), 2.28-2.11 (m, 2H), 1.93-1.78 (m, 1H).

Example 25: 2-(4-bromophenoxy)-N-((3R,6S)-6-(5-(2-(trifluoromethoxy)ethoxy)-1,3,4-oxadiazol-2-yl)tetrahydro-2H-pyran-3-yl)acetamide

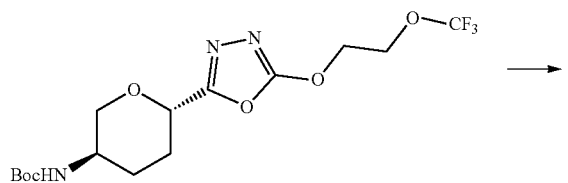

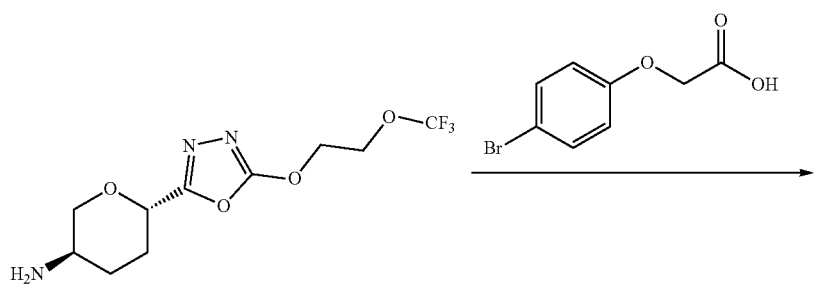

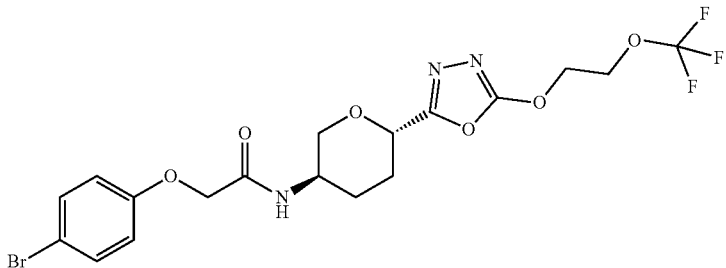

(3R,6S)-6-(5-(2-(trifluoromethoxy)ethoxy)-1,3,4-oxadiazol-2-yl)tetrahydro-2H-pyran-3-amine: To tert-butyl ((3R,6S)-6-(5-(2-(trifluoromethoxy)ethoxy)-1,3,4-oxadiazol-2-yl)tetrahydro-2H-pyran-3-yl)carbamate (50 mg, 0.13 mmol) in DCM (2 mL) was added TFA (440 mg, 3.86 mmol, 0.29 mL) at 25° C., and the mixture was stirred for 2 h. The reaction mixture was diluted with sat. NaHCO$_3$ (10 mL), and was extracted with DCM (2×10 mL). The combined organic layers were washed with brine (10 mL), dried over anhydrous Na$_2$SO$_4$, filtered and concentrated under reduced pressure to give the title compound.

2-(4-bromophenoxy)-N-((3R,6S)-6-(5-(2-(trifluoromethoxy)ethoxy)-1,3,4-oxadiazol-2-yl)tetrahydro-2H-pyran-3-yl)acetamide: Prepared employing General Procedure A employing (3R,6S)-6-(5-(2-(trifluoromethoxy)ethoxy)-1,3,4-oxadiazol-2-yl)tetrahydro-2H-pyran-3-amine (30 mg, 0.10 mmol), 2-(4-bromophenoxy)acetic acid (28 mg, 0.12 mmol), NEt$_3$ (41 mg, 0.40 mmol) and T3P solution (193 mg, 0.30 mmol, 0.18 mL, 50% in EtOAc) in EtOAc (2 mL) at 25° C. for 16 h. The residue was purified by prep-HPLC with the following conditions: column: Waters Xbridge BEH C18 100*30 mm*10 μm; mobile phase: [water (10 mM NH$_4$HCO$_3$)-ACN]; B %: 40%-70%, 10 min to give the title compound. LCMS: m/z=510.1, 512.1 [M+H]$^+$. $^1$H-NMR (400 MHz, CDCl$_3$): δ 7.44 (d, J=8.8 Hz, 2H), 6.83 (d, J=8.9 Hz, 2H), 6.45 (br d, J=7.9 Hz, 1H), 4.75-4.69 (m, 2H), 4.60 (t, J=6.3 Hz, 1H), 4.47 (s, 2H), 4.38-4.31 (m, 2H), 4.14 (br d, J=8.2 Hz, 2H), 3.37 (br t, J=10.9 Hz, 1H), 2.26 (br d, J=12.1 Hz, 1H), 2.17-2.09 (m, 2H), 1.66 (br s, 1H).

Example 26: 2-(3-fluoro-4-(trifluoromethyl)phenoxy)-N-((3R,6S)-6-(5-(2-(2,2,2-trifluoroethoxy)ethoxy)-1,3,4-oxadiazol-2-yl)tetrahydro-2H-pyran-3-yl)acetamide

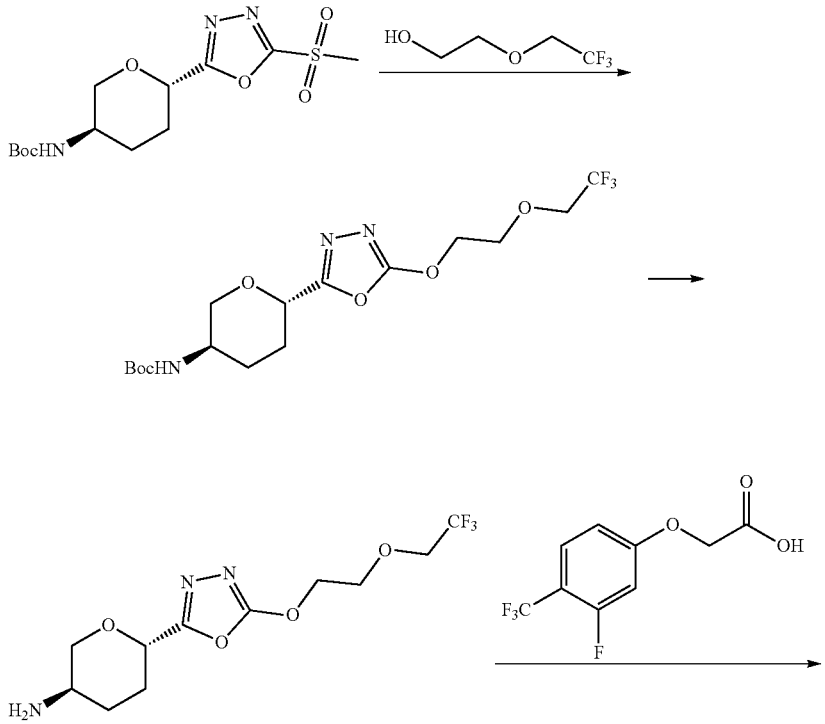

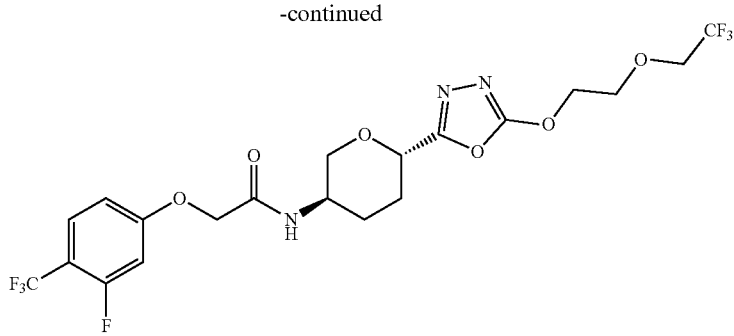

tert-butyl ((3R,6S)-6-(5-(2-(2,2,2-trifluoroethoxy) ethoxy)-1,3,4-oxadiazol-2-yl)tetrahydro-2H-pyran-3-yl)carbamate: To a solution of 2-(2,2,2-trifluoroethoxy)ethanol (40 mg, 0.28 mmol) in THF (2.0 mL) was added NaH (13.3 mg, 0.33 mmol, 60% in mineral oil) at 0° C., and the mixture was stirred at 0° C. for 30 min. tert-Butyl N-[(3R,6S)-6-(5-methylsulfonyl-1,3,4-oxadiazol-2-yl)tetrahydropyran-3-yl] carbamate (96.43 mg, 0.28 mmol) was added at 0° C., and the mixture was stirred at 18° C. for 2 h. The mixture was poured into sat. NH₄Cl solution (10 mL). The aqueous phase was extracted with EtOAc (3×8 mL). The combined organic phases were washed with brine (5 mL), dried over anhydrous Na₂SO₄, filtered and concentrated under reduced pressure. The residue was purified by prep-TLC (SiO₂, PE:EtOAc=1:3) to give the title compound. ¹H-NMR (400 MHz, CDCl₃): δ 4.69-4.61 (m, 2H), 4.55-4.42 (m, 2H), 4.17-4.11 (m, 1H), 4.04-3.99 (m, 2H), 3.92 (q, J=8.6 Hz, 2H), 3.73 (br s, 1H), 3.25 (br t, J=10.1 Hz, 1H), 2.29-2.16 (m, 1H), 2.15-1.98 (m, 2H), 1.57-1.42 (m, 10H).

(3R,6S)-6-(5-(2-(2,2,2-trifluoroethoxy)ethoxy)-1,3,4-oxadiazol-2-yl)tetrahydro-2H-pyran-3-amine: To a solution of tert-butyl ((3R,6S)-6-(5-(2-(2,2,2-trifluoroethoxy) ethoxy)-1,3,4-oxadiazol-2-yl)tetrahydro-2H-pyran-3-yl)carbamate (54 mg, 0.13 mmol) in DCM (2 mL) was added TFA (0.4 mL) and stirred at 20° C. for 1 h. The mixture was concentrated under reduced pressure to give the desired product.

2-(3-fluoro-4-(trifluoromethyl)phenoxy)-N-((3R,6S)-6-(5-(2-(2,2,2-trifluoroethoxy)ethoxy)-1,3,4-oxadiazol-2-yl) tetrahydro-2H-pyran-3-yl)acetamide: Prepared employing General Procedure A employing (3R,6S)-6-(5-(2-(2,2,2-trifluoroethoxy)ethoxy)-1,3,4-oxadiazol-2-yl)tetrahydro-2H-pyran-3-amine (40 mg, 0.13 mmol), 2-[3-fluoro-4-(trifluoromethyl)phenoxy]acetic acid (31 mg, 0.13 mmol), DIEA (67 mg, 0.51 mmol) and T3P (164 mg, 0.26 mmol, 50% in EtOAc) in EtOAc (2 mL) for 16 h at 20° C. The mixture was purified by p-HPLC with the following conditions: column: Waters Xbridge BEH C18 100*25 mm*5 μm; mobile phase: [water (10 mM NH₄HCO₃)-ACN]; B %: 30%-60%, 10 min to give the title compound. LCMS: m/z=532.1 [M+H]⁺. ¹H NMR (400 MHz, CDCl₃): δ 7.59 (t, J=8.3 Hz, 1H), 6.80 (br d, J=9.9 Hz, 2H), 6.40 (br d, J=7.7 Hz, 1H), 4.69-4.64 (m, 2H), 4.61 (t, J=6.2 Hz, 1H), 4.53 (s, 2H), 4.23-4.11 (m, 2H), 4.05-4.00 (m, 2H), 3.93 (q, J=8.6 Hz, 2H), 3.43-3.35 (m, 1H), 2.33-2.22 (m, 1H), 2.18-2.07 (m, 2H), 1.71-1.62 (m, 1H).

Example 27: 2-[3-fluoro-4-(trifluoromethyl)phenoxy]-N-[(3R,6S)-6-[5-[3-(trifluoromethoxy)cyclobutyl]-1,3,4-oxadiazol-2-yl]tetrahydropyran-3-yl] acetamide

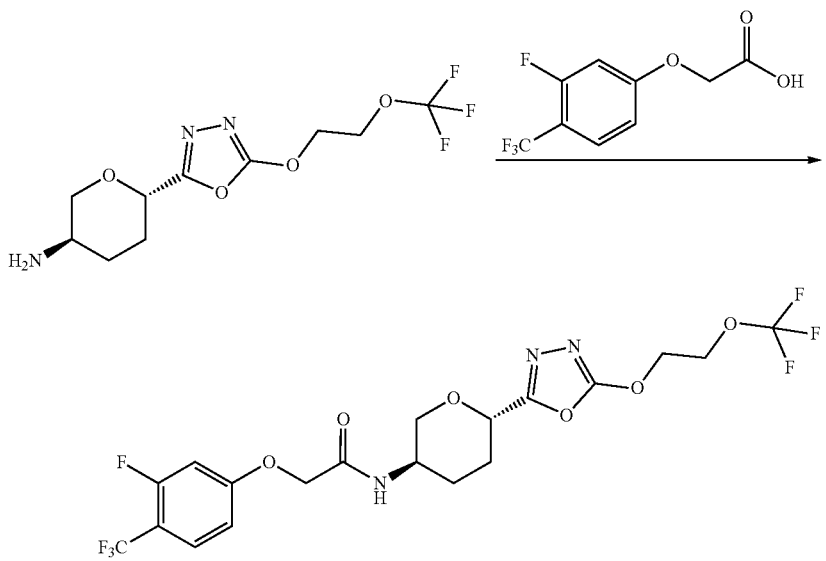

Prepared employing General Procedure A employing (3R,6S)-6-(5-(2-(trifluoromethoxy)ethoxy)-1,3,4-oxadiazol-2-yl)tetrahydro-2H-pyran-3-amine (200 mg, 0.650 mmol), 2-[3-fluoro-4-(trifluoromethyl)phenoxy]acetic acid (186 mg, 0.781 mmol), NEt$_3$ (329 mg, 3.25 mmol) and T3P solution (414 mg, 1.30 mmol, 0.300 mL, 50% in EtOAc) in EtOAc (3.5 mL) at 25° C. for 16 h. The residue was purified by column chromatography (0→100% EtOAc/hexanes) and then recrystallized from diethyl ether to give the desired product. LC-MS: m/z=518.71. $^1$H-NMR (400 MHz; CDCl$_3$): δ 7.60 (t, J=8.3 Hz, 1H), 6.82 (s, 1H), 6.80 (s, 1H), 6.42 (d, J=7.7 Hz, 1H), 4.75-4.72 (m, 2H), 4.64-4.61 (m, 1H), 4.54 (s, 2H), 4.37-4.35 (m, 2H), 4.22-4.14 (m, 2H), 3.43-3.38 (m, 1H), 2.32-2.25 (m, 1H), 2.14 (dt, J=9.7, 5.1 Hz, 2H), 1.74-1.63 (m, 1H).

Example 28: N-((3R,6S)-6-(5-(2-(2,2,2-trifluoroethoxy)ethoxy)-1,3,4-oxadiazol-2-yl)tetrahydro-2H-pyran-3-yl)-2-(4-(trifluoromethyl)phenoxy)acetamide 2-(2,2,2-trifluoroethoxy)ethyl 2-((2S,5R)-5-((tert-butoxycarbonyl)amino)tetrahydro-2H-pyran-2-carbonyl)hydrazinecarboxylate: To a solution of 2-(2,2,2-trifluoroethoxy)ethanol (300 mg, 2.08 mmol) in THF (5 mL) was added bis(trichloromethyl) carbonate (216 mg, 0.73 mmol), followed by dropwise pyridine (988 mg, 12.49 mmol, 1.01 mL) at 0° C. under N$_2$. The mixture was stirred at 20° C. for 2 h. The mixture was added tert-butyl N-[(3R,6S)-6-(hydrazinecarbonyl)tetrahydropyran-3-yl]carbamate (378 mg, 1.46 mmol) at 20° C. and stirred for 14 h. The mixture was poured into ice-water (45 mL), extracted with EtOAc (3×15 mL). The combined organic layers were washed with brine (15 mL), dried over anhydrous Na$_2$SO$_4$, filtered and concentrated under reduced pressure to afford the desired product. LCMS: m/z=374.1 [M+H]$^1$. $^1$H NMR (400 MHL-z, DMSO-d$_6$): δ 9.57 (br s, 1H), 9.10 (br s, 1H), 6.82 (br d, J=7.8 Hz, 1H), 4.17-4.05 (m, 4H), 3.92-3.68 (m, 4H), 3.42-3.34 (m, 1H), 3.07-2.94 (m, 1H), 1.89 (br d, J=7.9 Hz, 2H), 1.54-1.41 (m, 2H), 1.38 (s, 9H).

tert-butyl ((3R,6S)-6-(5-(2-(2,2,2-trifluoroethoxy)ethoxy)-1,3,4-oxadiazol-2-yl)tetrahydro-2H-pyran-3-yl)car-

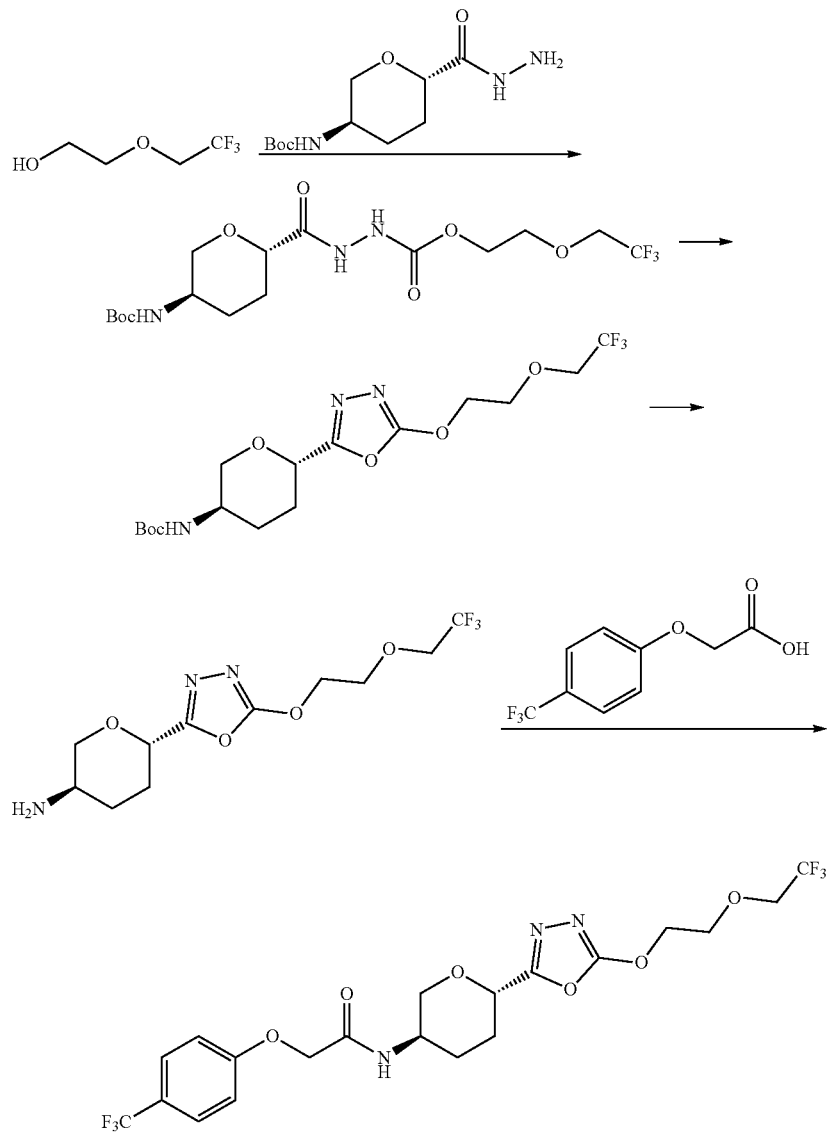

bamate: To a solution of 2-(2,2,2-trifluoroethoxy)ethyl 2-((2S,5R)-5-((tert-butoxycarbonyl)amino)tetrahydro-2H-pyran-2-carbonyl)hydrazinecarboxylate (600 mg, 1.40 mmol) in MeCN (10 mL) was added Cs$_2$CO$_3$ (1.82 g, 5.59 mmol) and p-TsCl (533 mg, 2.79 mmol) at 20° C. under N$_2$. The mixture was stirred for 16 h. The mixture was poured onto water (30 mL), and was extracted with EtOAc (3×15 mL). The combined organic layers were washed with brine (15 mL), dried over anhydrous Na$_2$SO$_4$, filtered and concentrated under reduced pressure. The residue was purified by silica gel column chromatography (PE:EtOAc=1:0 to 0:1) to give the desired product. LCMS: m/z=412.2 [M+H]$^1$. $^1$H NMR (400 MHL-z, CDCl$_3$): δ 4.69-4.61 (m, 2H), 4.56-4.48 (m, 1H), 4.45 (br s, 1H), 4.19-4.13 (m, 1H), 4.06-3.98 (m, 2H), 3.97-3.87 (m, 2H), 3.81-3.62 (m, 1H), 3.25 (br t, J=10.3 Hz, 1H), 2.28-2.18 (m, 1H), 2.16-2.07 (m, 1H), 1.46 (s, 11H).

(3R,6S)-6-(5-(2-(2,2,2-trifluoroethoxy)ethoxy)-1,3,4-oxadiazol-2-yl)tetrahydro-2H-pyran-3-amine: To a solution of tert-butyl ((3R,6S)-6-(5-(2-(2,2,2-trifluoroethoxy)ethoxy)-1,3,4-oxadiazol-2-yl)tetrahydro-2H-pyran-3-yl)carbamate (110 mg, 0.27 mmol) in DCM (2 mL) was added TFA (0.4 mL) at 20° C., and the mixture was stirred for 1 h. The mixture was concentrated under reduced pressure, the residue was poured into water, adjusted to pH=8 by addition of NH$_3$.H$_2$O, and was extracted with DCM:i-PrOH (3×5 mL, v:v=3:1). The combined organic layers were washed with brine (5 mL), dried over anhydrous Na$_2$SO$_4$, filtered and concentrated under reduced pressure to give the desired product.

N-((3R,6S)-6-(5-(2-(2,2,2-trifluoroethoxy)ethoxy)-1,3,4-oxadiazol-2-yl)tetrahydro-2H-pyran-3-yl)-2-(4-(trifluoromethyl)phenoxy)acetamide: Prepared employing General Procedure A employing (3R,6S)-6-(5-(2-(2,2,2-trifluoroethoxy)ethoxy)-1,3,4-oxadiazol-2-yl)tetrahydro-2H-pyran-3-amine (83 mg, 0.27 mmol), 2-[4-(trifluoromethyl)phenoxy]acetic acid (59 mg, 0.27 mmol), DIEA (207 mg, 1.60 mmol, 0.28 mL) and T3P (509 mg, 0.80 mmol, 0.48 mL, 5000 in EtOAc) in EtOAc (3 mL) at 20° C. for 5 h. The mixture was purified by p-TLC (PE:EtOAc=0:1) to give the title compound. LCMS: m/z=514.1 [M+H]$^+$. $^1$H NMR (400 MHz, DMSO): δ 7.61 (d, J=8.7 Hz, 2H), 7.02 (d, J=8.7 Hz, 2H), 6.48 (br d, J=7.7 Hz, 1H), 4.68-4.62 (m, 2H), 4.62-4.56 (m, 1H), 4.54 (s, 2H), 4.23-4.10 (m, 2H), 4.06-3.98 (m, 2H), 3.92 (q, J=8.6 Hz, 2H), 3.43-3.32 (m, 1H), 2.30-2.20 (m, 1H), 2.16-2.04 (m, 2H), 1.70-1.61 (m, 1H).

Examples 29-31

The following compounds were, or can be, made via similar procedures as those described above.

| Ex. | Structure | LCMS m/z ([M + H]$^+$) |
|---|---|---|
| 29 | 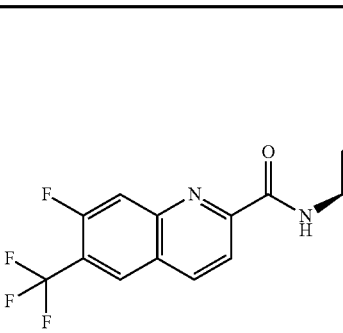 | 539.0 |
| 30 | 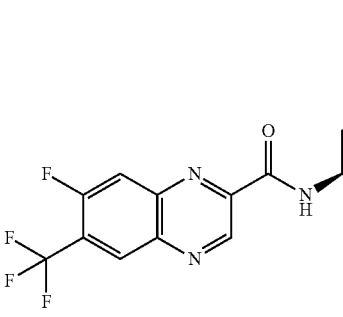 | 540.1 |
| 31 | 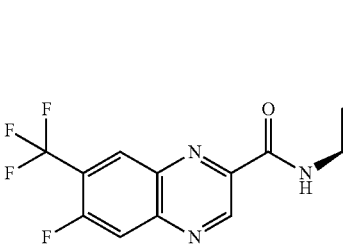 | 540.1 |

Example 32: N-((3R,6S)-6-(5-(2-(trifluoromethoxy)ethoxy)-1,3,4-thiadiazol-2-yl)tetrahydro-2H-pyran-3-yl)-6-(trifluoromethyl)quinoxaline-2-carboxamide (32)

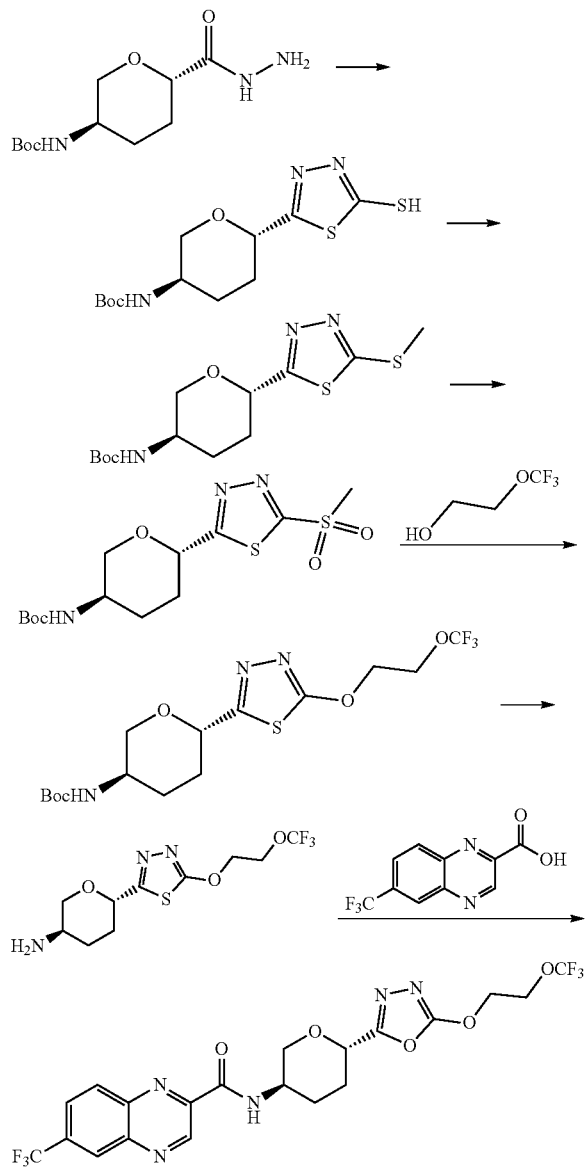

tert-butyl ((3R,6S)-6-(5-mercapto-1,3,4-thiadiazol-2-yl)tetrahydro-2H-pyran-3-yl)carbamate: To a mixture of tert-butyl ((3R,6S)-6-(hydrazinecarbonyl)tetrahydro-2H-pyran-3-yl)carbamate (7.6 g, 29.3 mmol) in MeOH (60 mL) was added KOH (4.11 g, 73.3 mmol) at 25° C. under N₂. The mixture was stirred at 25° C. for 0.5 h, CS₂ (8.93 g, 117 mmol, 7.08 mL) was added, and the mixture was stirred at 80° C. for 15.5 h. The reaction mixture was concentrated under reduced pressure to give a residue. The residue was added H₂O (250 mL) at 25° C. and then adjusted to pH=3 with HCl (3 M). The mixture was filtered and the filtered cake was concentrated under reduced pressure to give the title compound.

tert-butyl ((3R,6S)-6-(5-(methylthio)-1,3,4-thiadiazol-2-yl)tetrahydro-2H-pyran-3-yl)carbamate: To a solution of tert-butyl ((3R,6S)-6-(5-mercapto-1,3,4-thiadiazol-2-yl)tetrahydro-2H-pyran-3-yl)carbamate (5.0 g, 15.8 mmol) in DMF (40 mL) was added K₂CO₃ (4.35 g, 31.5 mmol) at 0° C. under N₂. MeI (4.47 g, 31.5 mmol) was added drop-wise at 0° C., and the mixture was stirred at 25° C. for 15 h. The mixture was poured into water (150 mL), and the aqueous phase was extracted with EtOAc (3×30 mL). The combined organic phases were washed with brine (10 mL), dried over anhydrous Na₂SO₄, filtered and concentrated under reduced pressure. The residue was purified by silica gel column chromatography (PE:EtOAc=50:1 to 1:1) to give the title compound. $^1$H NMR (400 MHz, CDCl₃): δ 4.71 (dd, J=2.4, 10.7 Hz, 1H), 4.40 (br s, 1H), 4.19 (ddd, J=2.0, 4.4, 11.0 Hz, 1H), 3.70 (br d, J=5.6 Hz, 1H), 3.30-3.18 (m, 1H), 2.77 (s, 3H), 2.33 (br dd, J=2.8, 13.6 Hz, 1H), 2.25-2.16 (m, 1H), 1.89-1.75 (m, 1H), 1.45 (m, 10H).

tert-butyl ((3R,6S)-6-(5-(methylsulfonyl)-1,3,4-thiadiazol-2-yl)tetrahydro-2H-pyran-3-yl)carbamate: To a solution of tert-butyl ((3R,6S)-6-(5-(methylthio)-1,3,4-thiadiazol-2-yl)tetrahydro-2H-pyran-3-yl)carbamate (1.6 g, 4.83 mmol) in DCM (30 mL) was added m-CPBA (5.21 g, 24.1 mmol, 80% purity) at 0° C. The mixture was stirred at 25° C. for 15 h. The mixture was poured into sat. Na₂S₂O₃ (30 mL) and then adjusted to pH=7-8 with sat.NaHCO₃. The aqueous phase was extracted with DCM (3×15 mL). The combined organic phase was washed with brine (10 mL), dried over anhydrous Na₂SO₄, filtered and concentrated under reduced pressure. The residue was purified by silica gel column chromatography (PE:EtOAc=20:1 to 1:1) to give the title compound. $^1$H NMR (400 MHz, CDCl₃): δ 4.81 (dd, J=2.8, 11.2 Hz, 1H), 4.36 (br s, 1H), 4.31-4.22 (m, 1H), 3.76 (br d, J=13.2 Hz, 1H), 3.46 (s, 3H), 3.27 (t, J=10.8 Hz, 1H), 2.50-2.42 (m, 1H), 2.30-2.20 (m, 1H), 1.88-1.74 (m, 1H), 1.57-1.52 (m, 1H), 1.46 (s, 9H).

tert-butyl ((3R,6S)-6-(5-(2-(trifluoromethoxy)ethoxy)-1,3,4-thiadiazol-2-yl)tetrahydro-2H-pyran-3-yl)carbamate: To a solution of 2-(trifluoromethoxy)ethanol (180 mg, 1.38 mmol) in THF (5 mL) was added NaH (66 mg, 1.66 mmol, 60% in mineral oil) at 0° C., and the mixture was stirred at 0° C. for 30 min. Then tert-butyl ((3R,6S)-6-(5-(methylsulfonyl)-1,3,4-thiadiazol-2-yl)tetrahydro-2H-pyran-3-yl)carbamate (502 mg, 1.38 mmol) was added at 0° C., and the mixture was stirred at 25° C. for 1 h. The mixture was poured into sat. NH₄Cl (15 mL), the aqueous phase was extracted with EtOAc (3×8 mL). The combined organic phases were washed with brine (5 mL), dried over anhydrous Na₂SO₄, filtered and concentrated under reduced pressure to give the title compound. $^1$H NMR (400 MHz, CDCl₃): δ 4.77-4.71 (m, 2H), 4.60 (dd, J=2.8, 10.8 Hz, 1H), 4.42-4.31 (m, 3H), 4.21-4.14 (m, 1H), 3.72 (br s, 1H), 3.21 (t, J=10.8 Hz, 1H), 2.30 (br dd, J=2.8, 13.6 Hz, 1H), 2.25-2.16 (m, 1H), 1.89-1.76 (m, 1H), 1.55-1.43 (m, 10H).

(3R,6S)-6-(5-(2-(trifluoromethoxy)ethoxy)-1,3,4-thiadiazol-2-yl)tetrahydro-2H-pyran-3-amine: To a solution of tert-butyl ((3R,6S)-6-(5-(2-(trifluoromethoxy)ethoxy)-1,3,4-thiadiazol-2-yl)tetrahydro-2H-pyran-3-yl)carbamate (100 mg, 0.24 mmol) in DCM (5.0 mL) was added TFA (1.0 mL), and the mixture was stirred at 25° C. for 1 h. The mixture was adjusted to pH=7-8 with sat. NaHCO₃. The aqueous phase was extracted with DCM/i-PrOH (3×5 mL, v:v=3:1). The combined organic phases were dried over anhydrous Na₂SO₄, filtered and concentrated under reduced pressure to give the title compound.

N-((3R,6S)-6-(5-(2-(trifluoromethoxy)ethoxy)-1,3,4-thiadiazol-2-yl)tetrahydro-2H-pyran-3-yl)-6-(trifluoromethyl)quinoxaline-2-carboxamide: To a solution of (3R,6S)-6-(5-(2-(trifluoromethoxy)ethoxy)-1,3,4-thiadiazol-2-yl)

tetrahydro-2H-pyran-3-amine (60 mg, 0.19 mmol) and 6-(trifluoromethyl)quinoxaline-2-carboxylic acid (46 mg, 0.19 mmol) in EtOAc (5 mL) was added T3P solution (0.38 mmol, 0.23 mL, 50% in EtOAc) and DIEA (99 mg, 0.76 mmol), and the mixture was stirred at 25° C. for 2 h. The mixture was poured into water (15 mL). The aqueous phase was extracted with EtOAc (3×5 mL). The combined organic phase was washed with brine (5 mL), dried over anhydrous $Na_2SO_4$, filtered and concentrated under reduced pressure. The residue was purified by prep-HPLC (neutral) under the following conditions: column: Welch Xtimate C18 150*25 mm*5 m; mobile phase: [water (10 mM $NH_4HCO_3$)-ACN]; B %: 45%-70%, 10 min to give the title compound. LC-MS: m/z: 538.0 [M+H]$^+$. $^1$H NMR (400 MHz, $CDCl_3$): δ 9.78 (s, 1H), 8.53 (s, 1H), 8.28 (d, J=8.8 Hz, 1H), 8.05 (dd, J=1.6, 8.8 Hz, 1H), 7.82 (br d, J=7.6 Hz, 1H), 4.81-4.70 (m, 3H), 4.44-4.27 (m, 4H), 3.58-3.45 (m, 1H), 2.49-2.30 (m, 2H), 2.05-1.93 (m, 1H), 1.92-1.80 (m, 1H).

Example 33: 2-(3-fluoro-4-(trifluoromethyl)phenoxy)-N-((3R,6S)-6-(5-(2-(trifluoromethoxy)ethoxy)-1,3,4-thiadiazol-2-yl)tetrahydro-2H-pyran-3-yl)acetamide (33)

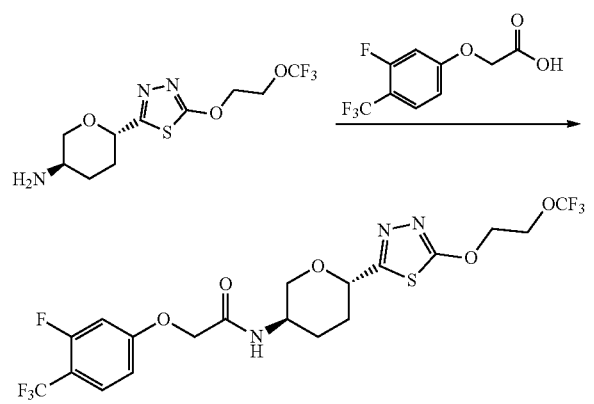

2-(3-fluoro-4-(trifluoromethyl)phenoxy)-N-((3R,6S)-6-(5-(2-(trifluoromethoxy)ethoxy)-1,3,4-thiadiazol-2-yl)tetrahydro-2H-pyran-3-yl)acetamide: To a solution of (3R,6S)-6-(5-(2-(trifluoromethoxy)ethoxy)-1,3,4-thiadiazol-2-yl)tetrahydro-2H-pyran-3-amine (75 mg, 0.24 mmol) in EtOAc (3.0 mL) was added 2-[3-fluoro-4-(trifluoromethyl)phenoxy]acetic acid (57 mg, 0.24 mmol), DIEA (124 mg, 0.96 mmol, 0.17 mL) and T3P solution (305 mg, 0.48 mmol, 0.28 mL, 50% in EtOAc) at 0° C. under $N_2$. The mixture was stirred at 25° C. for 2 h. The mixture was poured into $NaHCO_3$ (30 mL), extracted with EtOAc (3×10 mL). The combined organic layers were washed with brine (10 mL), dried over $Na_2SO_4$, filtered and concentrated under reduced pressure. The residue was purified by p-HPLC (neutral) under the following conditions: column: Welch Xtimate C18 150×25 mm×5 m; mobile phase: [water (10 mM $NH_4HCO_3$)-ACN]; B %: 45%-70%, 10 min to give 2-(3-fluoro-4-(trifluoromethyl)phenoxy)-N-((3R,6S)-6-(5-(2-(trifluoromethoxy)ethoxy)-1,3,4-thiadiazol-2-yl)tetrahydro-2H-pyran-3-yl)acetamide. LCMS: m/z=534.1 [M+H]$^+$. $^1$H NMR (400 MHz, $CDCl_3$): δ 7.58 (t, J=8.3 Hz, 1H), 6.79 (d, J=9.9 Hz, 2H), 6.30 (br d, J=7.9 Hz, 1H), 4.78-4.72 (m, 2H), 4.67 (dd, J=2.8, 10.4 Hz, 1H), 4.53 (s, 2H), 4.38-4.32 (m, 2H), 4.24-4.11 (m, 2H), 3.39-3.29 (m, 1H), 2.37-2.29 (m, 1H), 2.28-2.19 (m, 1H), 1.97-1.84 (m, 1H), 1.72-1.62 (m, 1H).

Biological Example 1

Biochemical Assay of the Compounds

Cellular stress leads to activation of the integrated stress response pathway through one of four eukaryotic initiation factor 2α kinases and halts global translation, while allowing for the translation of select transcripts like ATF4 (activating transcription factor 4) that are important for the response to cellular stress. During normal conditions, small open reading frames (ORFs) in the 5' UTR of ATF4 occupy the ribosome and prevent translation of the coding sequence of ATF4. During stress conditions however, the ribosome scans past these upstream ORFs and preferentially begins translation at the coding sequence of ATF4. In this way, the translation, and thus protein level of ATF4 is a readout of ISR pathway activation. Thus, a fusion of the uORFs and the beginning of the coding sequence of ATF to a common cellular reporter like nano-luciferase allows for a sensitive and high-throughput readout of ISR pathway activity.

Compounds as provided herein were tested in the following assay. The ATF4 Nano Luciferase reporter was constructed by fusing the human full length 5' untranslated region (5'-UTR) and a small portion of the coding sequence of the ATF4 gene upstream of the Nano Luciferase (NLuc) coding sequence lacking it's start codon. Specifically, nucleotides +1 through +364 (relative to the transcriptional start site) of ATF4 transcript variant 2 (NCBI NM_182810.2) flanked 5' by EcoRI and 3' by BamHI restriction enzyme sites were synthesized and cloned into the EcoRI/BamHI cloning sites of pLVX-EF1a-IRES-Puro lentivirus vector (Clontech). Lentiviral particles were produced with Lenti-X single shots (VSV-G, Clontech) according to the manufacturer's instructions and used to transduce a human H4 neuroglioma cell line (ATCC HTB-148). H4 cells were selected with 1.25 µg/mL Puromycin, and clonal cell lines generated by limiting dilution. This cell line was utilized to generate an integrated stress response (ISR) assay to evaluate the activity of ISR pathway inhibitors via luminescence readout. The H4 ATF4-NLuc (clone 17) cell line was plated at a density of 15,000 or 2.50 cells in 96-well or 384-well respectively in DMEM+10% fetal bovine serum. 24-hours later test compounds diluted in dimethyl sulfoxide (DMSO) were added for 30 minutes at 37° C., followed by ISR pathway activation with 50 µm sodium arsenite aqueous solution for 6 additional hours. Nano Glo luciferase reagent (N1150, Promega) was added according to manufacturer instructions and the luminescence signal (corresponding to the level of ATF4 translation and thus ISR pathway activation) was read with a standard plate reader with luminescence detection capabilities.

In the table below, activity of the tested compounds is provided.

TABLE 3

| Ex. | Activity (nM) |
| --- | --- |
| 1 | 1.2 |
| 2 | 5.0 |
| 3 | 11.4 |
| 4 | 53.2 |
| 5 | 13.6 |

TABLE 3-continued

| Ex. | Activity (nM) |
|---|---|
| 6 | 11 |
| 7 | 3.8 |
| 21 | 7.9 |
| 22 | 14.9 |
| 23 | 1 |
| 24 | 27 |
| 25 | 2 |
| 26 | 7.9 |
| 27 | 1.2 |
| 28 | 15.5 |
| 29 | 1.4 |
| 30 | 2.8 |
| 31 | 7.2 |
| 32 | 173 |
| 33 | 5.9 |

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation.

Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

What is claimed is:
1. A compound of Formula I:

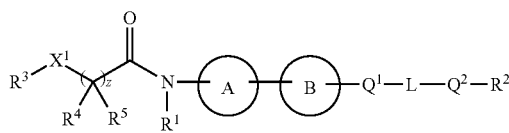

or a pharmaceutically acceptable salt, isotopically enriched analog, stereoisomer, mixture of stereoisomers, or prodrug thereof, wherein:
ring A is $C_{3-10}$ cycloalkyl or heterocyclyl, provided ring A is not bicyclo[1.1.1]pentanyl or bicyclo[2.1.1]hexanyl; wherein the $C_{3-10}$ cycloalkyl or heterocyclyl is optionally substituted with one to six $R^{14}$;

ring B is

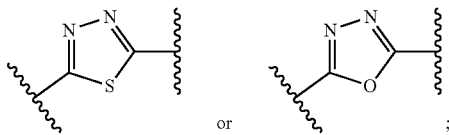 [SMILES: *c1nnc(*)s1 ; *c1nnc(*)o1]

$Q^1$ and $Q^2$ are each independently O, S, or $NR^{15}$;
L is a $C_{1-6}$ alkylene linker, optionally substituted with one to three substituents independently selected from halo, cyano, nitro, —$OR^6$, —$SR^6$, —$SF_5$, —$NR^6R^7$, $C_{1-6}$ alkyl, $C_{2-6}$ alkenyl, $C_{2-6}$ alkynyl, —$C(O)R^6$, —$C(O)OR^6$, —$OC(O)OR^6$, —$OC(O)R^6$, —$C(O)NR^6R^7$, —$OC(O)NR^6R^7$, —$NR^6C(O)NR^7R^8$, —$S(O)_{1-2}R^6$, —$S(O)_{1-2}NR^6R^7$, —$NR^6S(O)_{1-2}R^7$, —$NR^6S(O)_{1-2}NR^7R^8$, —$NR^6C(O)R^7$, and —$NR^6C(O)OR^7$;
z is 0 or 1;
$X^1$ is O, $NR^9$, or a bond;
$R^1$ is hydrogen, $C_{1-12}$ alkyl, $C_{2-12}$ alkenyl, $C_{2-12}$ alkynyl, $C_{3-10}$ cycloalkyl, or heterocyclyl, each of which, other than hydrogen, is optionally substituted with one to three $R^{11}$;
$R^2$ is $C_{1-6}$ haloalkyl;
$R^3$ is hydrogen, $C_{1-12}$ alkyl, $C_{2-12}$ alkenyl, $C_{2-12}$ alkynyl, $C_{3-10}$ cycloalkyl, heterocyclyl, aryl, or heteroaryl, each of which, other than hydrogen, is optionally substituted with one to five $R^{11}$;
$R^4$ and $R^5$ are independently hydrogen, $C_{1-12}$ alkyl, $C_{2-12}$ alkenyl, or $C_{2-12}$ alkynyl, each of which, other than hydrogen, is independently optionally substituted with one to five $R^{11}$;
or $R^3$ and $R^4$, together with the atoms to which they are attached, join to form a $C_{3-10}$ cycloalkyl or heterocyclyl, each of which is optionally substituted with one to five $R^{11}$;
or $R^4$ and $R^5$, together with the atoms to which they are attached, join to form a $C_{3-10}$ cycloalkyl or heterocyclyl, each of which is optionally substituted with one to five $R^{11}$;
each of $R^6$, $R^7$, and $R^8$ is independently hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{20}$, —$C(O)OR^{20}$, —$C(O)NR^{20}R^{21}$, —$S(O)_{1-2}R^{20}$, or —$S(O)_{1-2}NR^{20}R^{21}$, wherein each alkyl, alkenyl, alkynyl, cycloalkyl, heterocyclyl, aryl, and heteroaryl of $R^6$, $R^7$, and $R^8$ is independently optionally substituted with one to five $R^{12}$; or two of $R^6$, $R^7$, and $R^8$ are taken together with the atoms to which they are attached to form heterocyclyl independently optionally substituted by one to three halo, oxo, or $C_{1-12}$ alkyl independently optionally substituted by one to three oxo, halo, hydroxyl, or amino;
$R^9$ is hydrogen, $C_{1-12}$ alkyl, $C_{2-12}$ alkenyl, $C_{2-12}$ alkynyl, $C_{3-10}$ cycloalkyl, or heterocyclyl, each of which, other than hydrogen, is optionally substituted with one to three $R^{11}$;
each $R^{11}$ is independently halo, cyano, nitro, oxo, —$OR^6$, —$SR^6$, —$SF_5$, —$NR^6R^7$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^6$, —$C(O)OR^6$, —$OC(O)OR^6$, —$OC(O)R^6$, —$C(O)NR^6R^7$, —$OC(O)NR^6R^7$, —$NR^6C(O)NR^7R^8$, —$S(O)_{1-2}R^6$, —$S(O)_{1-2}NR^6R^7$, —$NR^6S(O)_{1-2}R^7$, —$NR^6S(O)_{1-2}NR^7R^8$, —$NR^6C(O)R^7$, or —$NR^6C(O)OR^7$, wherein each alkyl, alkenyl, alkynyl, cycloalkyl, heterocyclyl, aryl, and heteroaryl of $R^{11}$ is independently optionally substituted with one to five $R^{12}$;

each $R^{12}$ is independently halo, cyano, nitro, oxo, —$OR^{30}$, —$SR^{30}$, —$SF_5$, —$NR^{30}R^{31}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{30}$, —$C(O)OR^{30}$, —$OC(O)OR^{30}$, —$OC(O)R^{30}$, —$C(O)NR^{30}R^{31}$, —$OC(O)NR^{30}R^{31}$, —$OC(O)NR^{30}R^{31}$, —$NR^{30}C(O)NR^{30}R^{31}$; —$S(O)_{1-2}R^{30}$, —$S(O)_{1-2}NR^{30}R^{31}$, —$NR^{30}S(O)_{1-2}R^{31}$, —$NR^{30}S(O)_{1-2}NR^{30}R^{31}$, —$NR^{30}C(O)R^{31}$, or —$NR^{30}C(=O)OR^{31}$, wherein each alkyl, alkenyl, alkynyl, cycloalkyl, heterocyclyl, aryl, and heteroaryl of $R^{12}$ is independently optionally substituted with one to three halo or $C_{1-12}$ alkyl independently optionally substituted by one to three oxo, halo, hydroxyl, or amino;

each $R^{14}$ is independently halo, cyano, —$NR^6R^7$, $C_{1-6}$ alkyl, $C_{1-6}$ alkoxy, or $C_{1-6}$ haloalkyl, or two $R^{14}$ together with the atoms to which they are attached form a ring or a C=O;

each $R^{15}$ is independently hydrogen, $C_{1-6}$ alkyl, or $C_{1-6}$ haloalkyl;

each $R^{20}$ and $R^{21}$ is independently hydrogen or $C_{1-12}$ alkyl independently optionally substituted with one to three oxo, halo, hydroxyl, or amino; or $R^{20}$ and $R^{21}$ are taken together with the atoms to which they are attached to form heterocyclyl independently optionally substituted by one to three halo or $C_{1-12}$ alkyl independently optionally substituted by one to three oxo, halo, hydroxyl, or amino; and each $R^{30}$ and $R^{21}$ is independently hydrogen or $C_{1-12}$ alkyl independently optionally substituted with one to three oxo, halo, hydroxyl, or amino; or $R^{30}$ and $R^{31}$ are taken together with the atoms to which they are attached to form heterocyclyl independently optionally substituted by one to three halo or $C_{1-12}$ alkyl independently optionally substituted by one to three oxo, halo, hydroxyl, or amino.

2. The compound of claim 1, or a pharmaceutically acceptable salt, isotopically enriched analog, stereoisomer, mixture of stereoisomers, or prodrug thereof, wherein ring A is monocyclic cycloalkyl, fused bicyclic cycloalkyl, or spiro bicyclic cycloalkyl, wherein each is optionally substituted with one to six $R^{14}$.

3. The compound of claim 1, or a pharmaceutically acceptable salt, isotopically enriched analog, stereoisomer, mixture of stereoisomers, or prodrug thereof, wherein ring A is heterocyclyl, wherein each is optionally substituted with one to six $R^{14}$.

4. The compound of claim 1, or a pharmaceutically acceptable salt, isotopically enriched analog, stereoisomer, mixture of stereoisomers, or prodrug thereof, wherein ring A is selected from

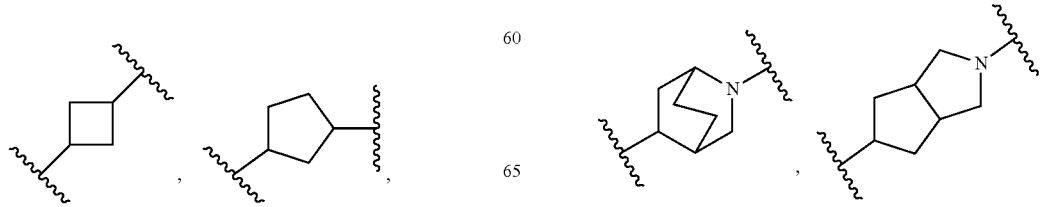

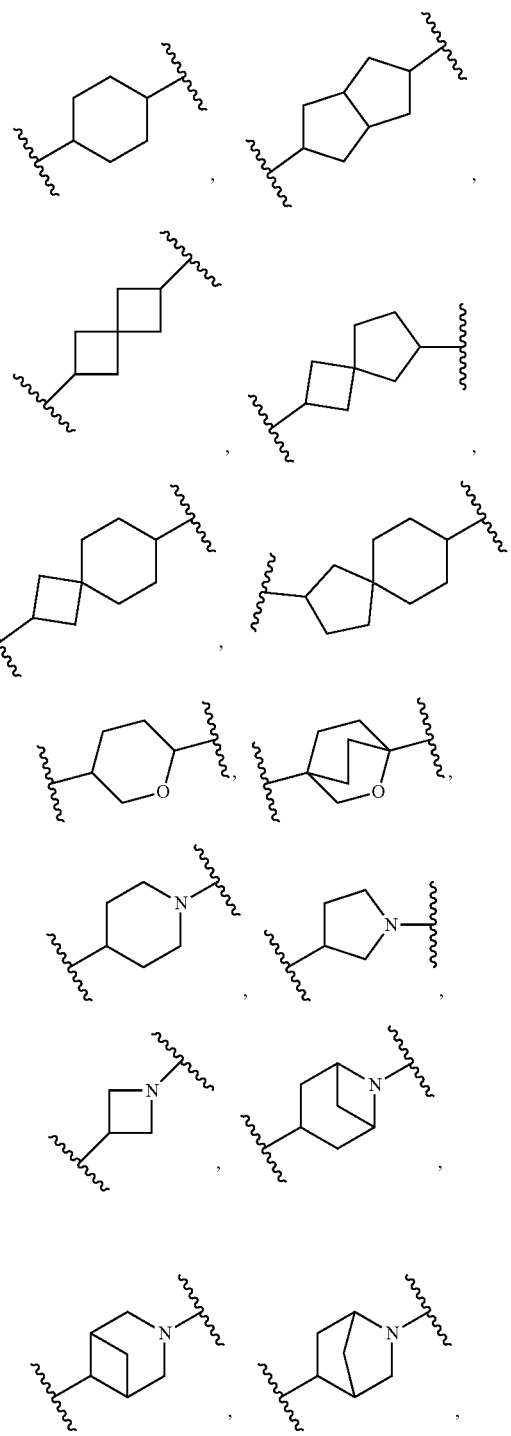

-continued

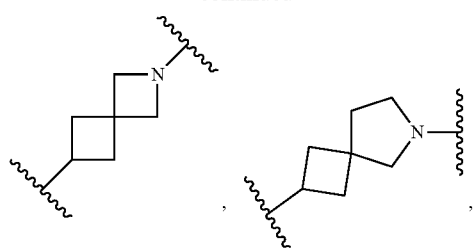

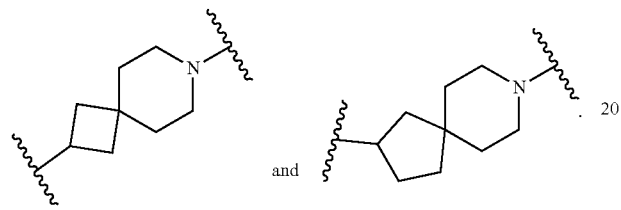

and wherein each is independently optionally substituted with one to four halo.

5. The compound of claim 1, or a pharmaceutically acceptable salt, isotopically enriched analog, stereoisomer, mixture of stereoisomers, or prodrug thereof, wherein ring B is

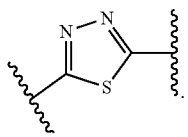 [SMILES: *c1nnc(*)s1]

6. The compound of claim 1, or a pharmaceutically acceptable salt, isotopically enriched analog, stereoisomer, mixture of stereoisomers, or prodrug thereof, wherein ring B is

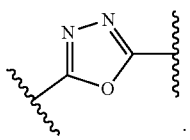 [SMILES: *c1nnc(*)o1]

7. A compound of Formula II:

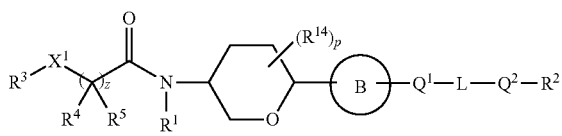

II or a pharmaceutically acceptable salt, isotopically enriched analog, stereoisomer, mixture of stereoisomers, or prodrug thereof, wherein:

p is 0, 1, 2, 3, 4, 5, or 6;
ring B is

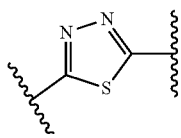 [SMILES: *c1nnc(*)s1]

or

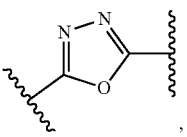 [SMILES: *c1nnc(*)o1]

, $Q^1$ and $Q^2$ are each independently O, S, or $NR^{15}$;

L is a $C_{1-6}$ alkylene linker, optionally substituted with one to three substituents independently selected from halo, cyano, nitro, —$OR^6$, —$SR^6$, —$SF_5$, —$NR^6R^7$, $C_{1-6}$ alkyl, $C_{2-6}$ alkenyl, $C_{2-6}$ alkynyl, —$C(O)R^6$, —$C(O)OR^6$, —$OC(O)OR^6$, —$OC(O)R^6$, —$C(O)NR^6R^7$, —$OC(O)NR^6R^7$, —$NR^6C(O)NR^7R^8$, —$S(O)_{1-2}R^6$, —$S(O)_{1-2}NR^6R^7$, —$NR^6S(O)_{1-2}R^7$, —$NR^6S(O)_{1-2}NR^7R^8$, —$NR^6C(O)R^7$, and —$NR^6C(O)OR^7$;

z is 0 or 1;

$X^1$ is O, $NR^9$, or a bond;

$R^1$ is hydrogen, $C_{1-12}$ alkyl, $C_{2-12}$ alkenyl, $C_{2-12}$ alkynyl, $C_{3-10}$ cycloalkyl, or heterocyclyl, each of which, other than hydrogen, is optionally substituted with one to three $R^{11}$;

$R^2$ is $C_{1-6}$ haloalkyl;

$R^3$ is hydrogen, $C_{1-12}$ alkyl, $C_{2-12}$ alkenyl, $C_{2-12}$ alkynyl, $C_{3-10}$ cycloalkyl, heterocyclyl, aryl, or heteroaryl, each of which, other than hydrogen, is optionally substituted with one to five $R^{11}$;

$R^4$ and $R^5$ are independently hydrogen, $C_{1-12}$ alkyl, $C_{2-12}$ alkenyl, $C_{2-12}$ alkynyl, each of which, other than hydrogen, is independently optionally substituted with one to five $R^{11}$;

or $R^3$ and $R^4$, together with the atoms to which they are attached, join to form a $C_{3-10}$ cycloalkyl or heterocyclyl, each of which is optionally substituted with one to five $R^{11}$;

or $R^4$ and $R^5$, together with the atoms to which they are attached, join to form a $C_{3-10}$ cycloalkyl or heterocyclyl, each of which is optionally substituted with one to five $R^{11}$;

each of $R^6$, $R^7$, and $R^8$ is independently hydrogen, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{20}$, —$C(O)OR^{20}$, —$C(O)NR^{20}R^{21}$, —$S(O)_{1-2}R^{20}$, or —$S(O)_{1-2}NR^{20}R^{21}$, wherein each alkyl, alkenyl, alkynyl, cycloalkyl, heterocyclyl, aryl, and heteroaryl of $R^6$, $R^7$, and $R^8$ is independently optionally substituted with one to five $R^{12}$; or two of $R^6$, $R^7$, and $R^8$ are taken together with the atoms to which they are attached to form heterocyclyl independently optionally substituted by one to three halo, oxo, or $C_{1-12}$ alkyl independently optionally substituted by one to three oxo, halo, hydroxyl, or amino;

$R^9$ is hydrogen, $C_{1-12}$ alkyl, $C_{2-12}$ alkenyl, $C_{2-12}$ alkynyl, $C_{3-10}$ cycloalkyl, or heterocyclyl, each of which, other than hydrogen, is optionally substituted with one to three $R^{11}$;

each $R^{11}$ is independently halo, cyano, nitro, oxo, —$OR^6$, —$SR^6$, —$SF_5$, —$NR^6R^7$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^6$, —$C(O)OR^6$, —$OC(O)OR^6$, —$OC(O)R^6$, —$C(O)NR^6R^7$, —$OC(O)NR^6R^7$, —$NR^6C(O)NR^7R^8$, —$S(O)_{1-2}R^6$, —$S(O)_{1-2}NR^6R^7$, —$NR^6S(O)_{1-2}R^7$, —$NR^6S(O)_{1-2}NR^7R^8$, —$NR^6C(O)R^7$, or —$NR^6C(O)OR^7$, wherein each alkyl, alkenyl, alkynyl, cycloalkyl, heterocyclyl, aryl, and heteroaryl of $R^{11}$ is independently optionally substituted with one to five $R^{12}$;

each $R^{12}$ is independently halo, cyano, nitro, oxo, —$OR^{30}$, —$SR^{30}$, —$SF_5$, —$NR^{30}R^{31}$, $C_{1-12}$ alkyl, $C_{2-12}$ alkenyl, $C_{2-12}$ alkynyl, $C_{3-10}$ cycloalkyl, heterocyclyl, aryl, heteroaryl, —$C(O)R^{30}$, —$C(O)OR^{30}$, —$OC(O)OR^{30}$, —$OC(O)R^{30}$, —$C(O)NR^{30}R^{31}$, —$OC(O)NR^{30}R^{31}$, —$NR^{30}C(O)NR^{30}R^{31}$, —$S(O)_{1-2}R^{30}$, —$S(O)_{1-2}NR^{30}R^{31}$, —$NR^{30}S(O)_{1-2}R^{31}$, —$NR^{30}S(O)_{1-2}NR^{30}R^{31}$, —$NR^{30}C(O)R^{31}$, or —$NR^{30}C(=O)OR^{31}$, wherein each alkyl, alkenyl, alkynyl, cycloalkyl, heterocyclyl, aryl, and heteroaryl of $R^{12}$ is independently optionally substituted with one to three halo or $C_{1-12}$ alkyl independently optionally substituted by one to three oxo, halo, hydroxyl, or amino;

each $R^{14}$ is independently halo, cyano, —$NR^6R^7$, $C_{1-6}$ alkyl, $C_{1-6}$ alkoxy, or C1-6 haloalkyl, or two $R^{14}$ together with the atoms to which they are attached form a ring or a C=O;

each $R^{15}$ is independently hydrogen, $C_{1-6}$ alkyl, or $C_{1-6}$ haloalkyl;

each $R^{20}$ and $R^{21}$ is independently hydrogen or $C_{1-12}$ alkyl independently optionally substituted with one to three oxo, halo, hydroxyl, or amino; or $R^{20}$ and $R^{21}$ are taken together with the atoms to which they are attached to form heterocyclyl independently optionally substituted by one to three halo or $C_{1-12}$ alkyl independently optionally substituted by one to three oxo, halo, hydroxyl, or amino; and each $R^{30}$ and $R^{31}$ is independently hydrogen or $C_{1-12}$ alkyl independently optionally substituted with one to three oxo, halo, hydroxyl, or amino; or $R^{30}$ and $R^{31}$ are taken together with the atoms to which they are attached to form heterocyclyl independently optionally substituted by one to three halo or $C_{1-12}$ alkyl independently optionally substituted by one to three oxo, halo, hydroxyl, or amino.

8. The compound of claim 1, or a pharmaceutically acceptable salt, isotopically enriched analog, stereoisomer, mixture of stereoisomers, or prodrug thereof, wherein $R^2$ is —$CHF_2$, —$CF_3$, or —$CH_2CF_3$.

9. The compound of claim 1, or a pharmaceutically acceptable salt, isotopically enriched analog, stereoisomer, mixture of stereoisomers, or prodrug thereof, wherein $Q^1$ is O.

10. The compound of claim 1, or a pharmaceutically acceptable salt, isotopically enriched analog, stereoisomer, mixture of stereoisomers, or prodrug thereof, wherein $Q^1$ is $NR^{15}$, and $Q^2$ is O.

11. The compound of claim 1, or a pharmaceutically acceptable salt, isotopically enriched analog, stereoisomer, mixture of stereoisomers, or prodrug thereof, wherein $Q^1$ and $Q^2$ are each O.

12. The compound of claim 1, or a pharmaceutically acceptable salt, isotopically enriched analog, stereoisomer, mixture of stereoisomers, or prodrug thereof, wherein L is —$CH_2CH_2$—.

13. The compound of claim 1, or a pharmaceutically acceptable salt, isotopically enriched analog, stereoisomer, mixture of stereoisomers, or prodrug thereof, wherein the moiety —$Q^1$—L—$Q^2$—$R^2$ is —$OCH_2CH_2OCF_3$ or —$NR^{15}CH_2CH_2OCF_3$.

14. The compound of claim 7, or a pharmaceutically acceptable salt, isotopically enriched analog, stereoisomer, mixture of stereoisomers, or prodrug thereof, wherein the moiety —$Q^1$—L—$Q^2$—$R^2$ is —$OCH_2CH_2OCF_3$.

15. The compound of claim 1, or a pharmaceutically acceptable salt, isotopically enriched analog, stereoisomer, mixture of stereoisomers, or prodrug thereof, wherein $X^1$ is O.

16. The compound of claim 1, or a pharmaceutically acceptable salt, isotopically enriched analog, stereoisomer, mixture of stereoisomers, or prodrug thereof, wherein $R^3$ is $C_{3-10}$ cycloalkyl, heterocyclyl, aryl, or heteroaryl, each of which is optionally substituted with one to five $R^{11}$.

17. The compound of claim 1, or a pharmaceutically acceptable salt, isotopically enriched analog, stereoisomer, mixture of stereoisomers, or prodrug thereof, wherein $R^3$ is $C_{3-10}$ cycloalkyl, aryl, or heteroaryl, each of which is optionally substituted with one to five $R^{11}$.

18. The compound of claim 1, or a pharmaceutically acceptable salt, isotopically enriched analog, stereoisomer, mixture of stereoisomers, or prodrug thereof, wherein $R^3$ is aryl or heteroaryl, each of which is optionally substituted with one to five $R^{11}$.

19. The compound of claim 14, or a pharmaceutically acceptable salt, isotopically enriched analog, stereoisomer, mixture of stereoisomers, or prodrug thereof, wherein $R^3$ is aryl or heteroaryl, each of which is optionally substituted with one to five $R^{11}$.

20. The compound of claim 1, or a pharmaceutically acceptable salt, isotopically enriched analog, stereoisomer, mixture of stereoisomers, or prodrug thereof, wherein $R^3$ is aryl or heteroaryl, each of which is optionally substituted with chloro, fluoro, —$CF_3$, or a combination thereof.

21. The compound of claim 1, or a pharmaceutically acceptable salt, isotopically enriched analog, stereoisomer, mixture of stereoisomers, or prodrug thereof, wherein $R^3$ is

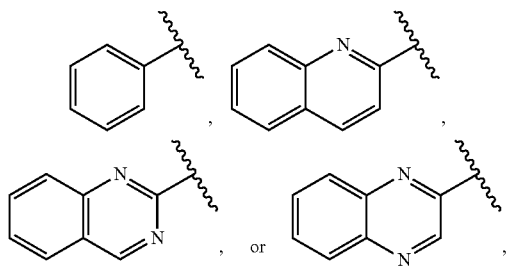

each of which is optionally substituted with one to five $R^{11}$.

22. The compound of claim 1, or a pharmaceutically acceptable salt, isotopically enriched analog, stereoisomer, mixture of stereoisomers, or prodrug thereof, wherein $R^4$ and $R^5$ are hydrogen.

23. The compound of claim 1, or a pharmaceutically acceptable salt, isotopically enriched analog, stereoisomer, mixture of stereoisomers, or prodrug thereof, wherein $R^1$ is hydrogen.
24. A compound, or a pharmaceutically acceptable salt, isotopically enriched analog, stereoisomer, mixture of stereoisomers, or prodrug thereof, selected from the group consisting of:
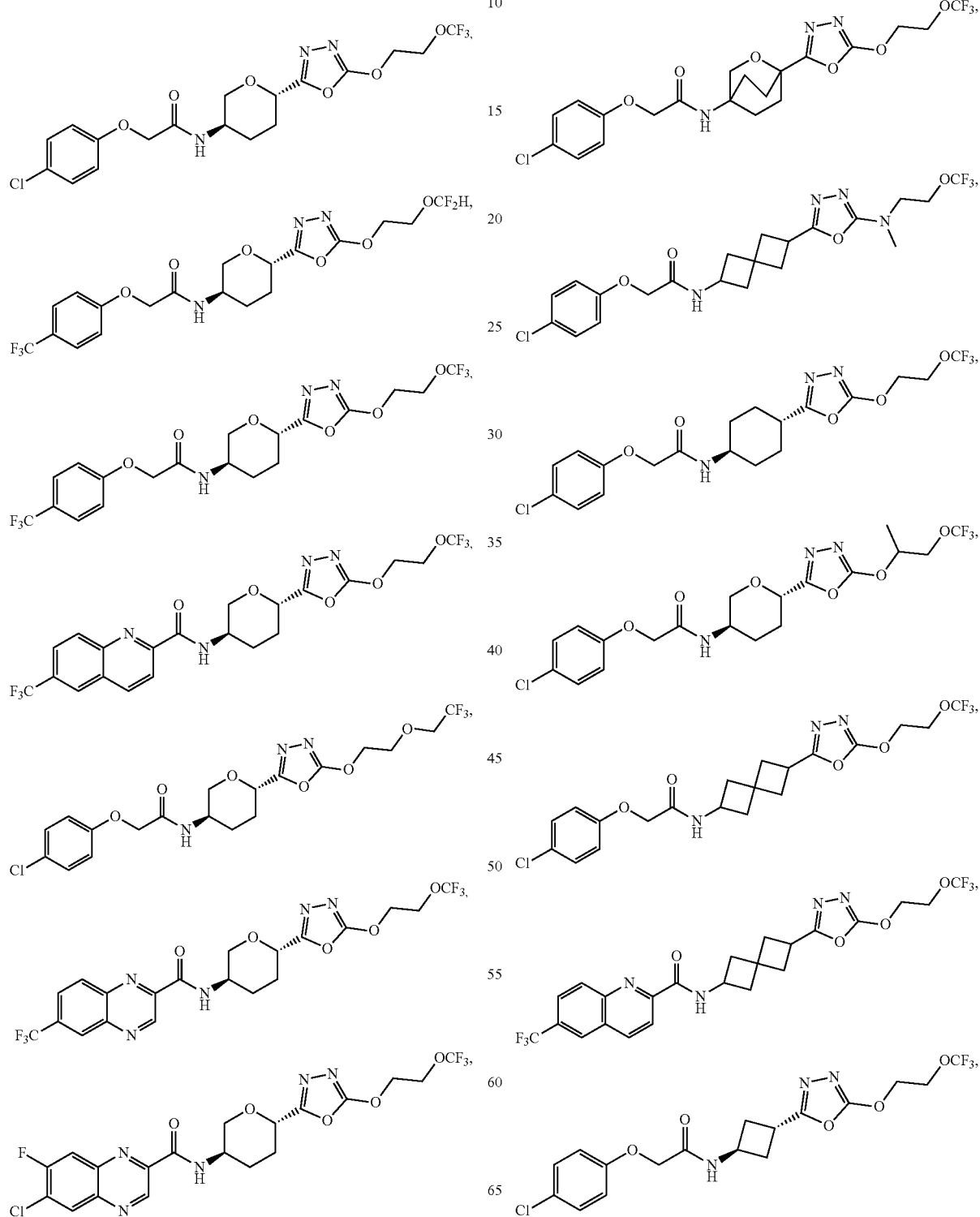

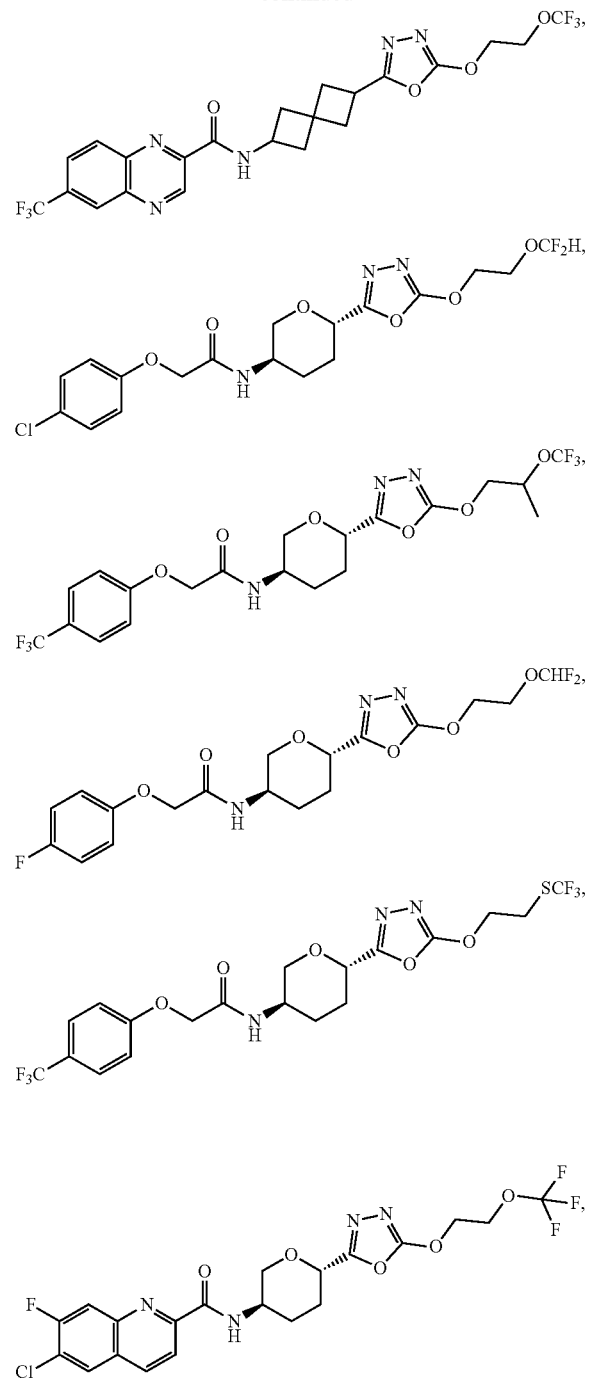
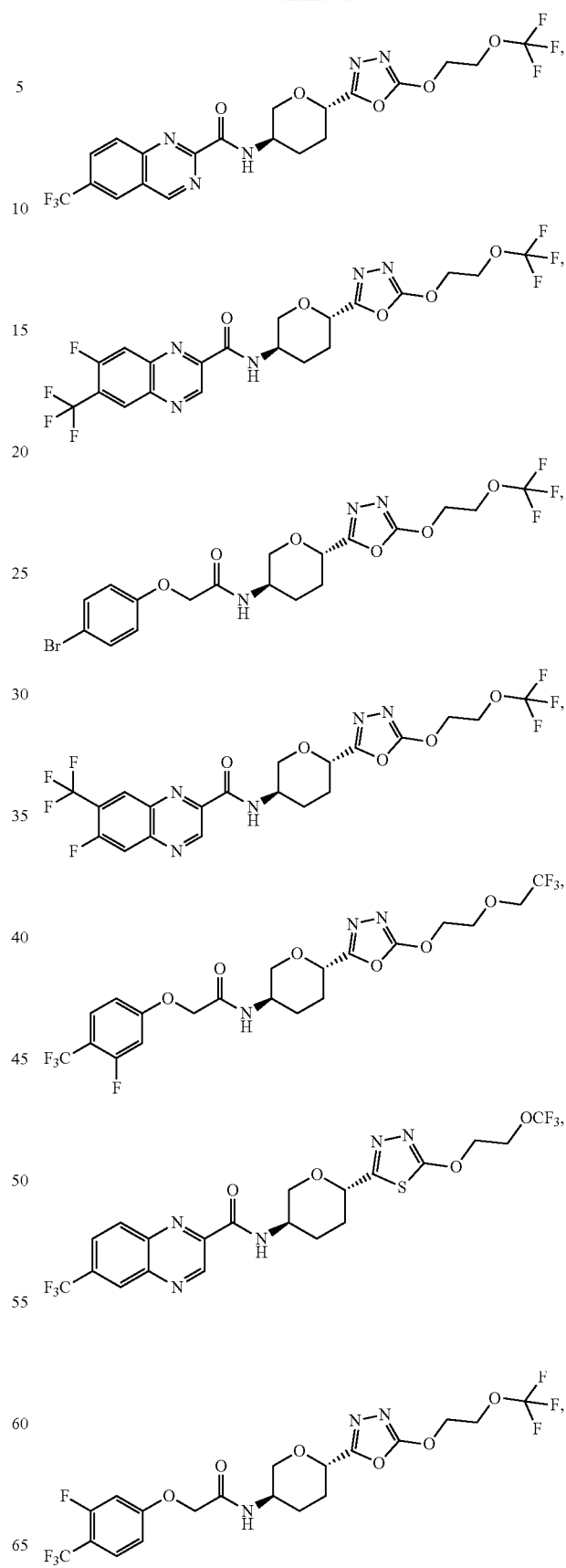

103
-continued
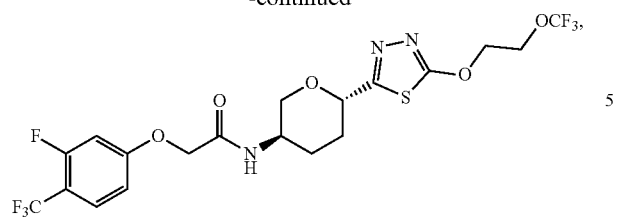
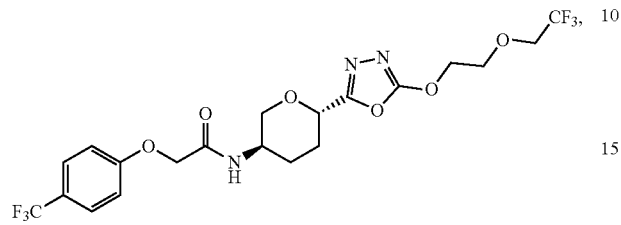
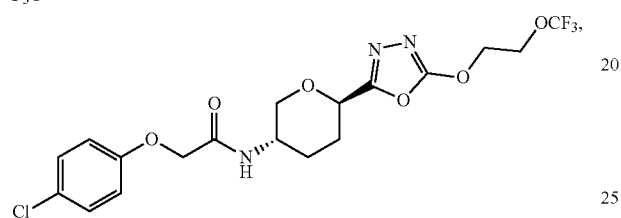
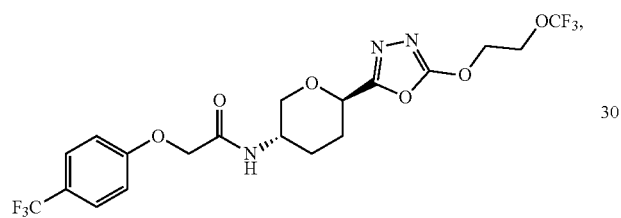
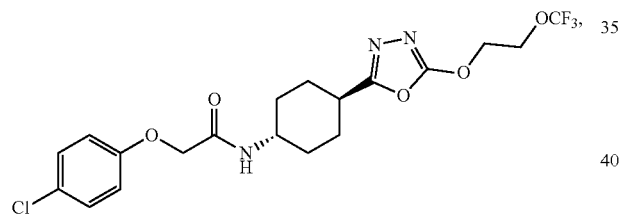
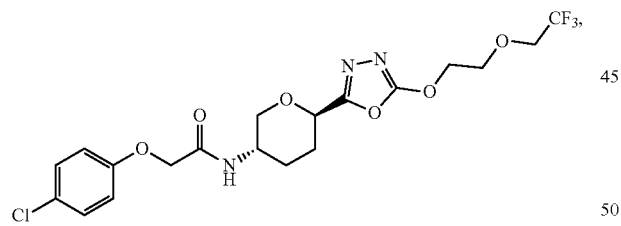
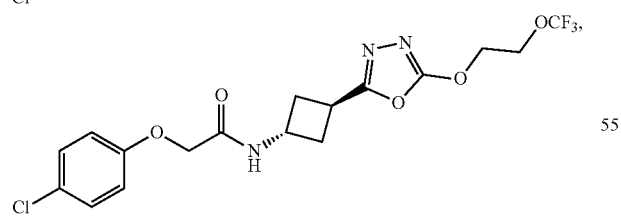
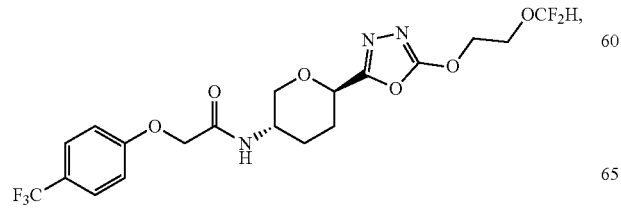
104
-continued
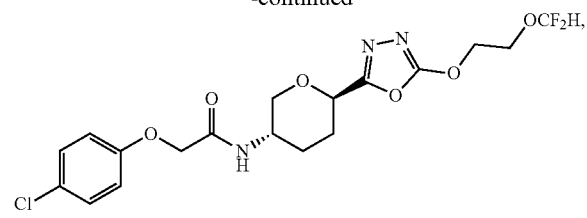
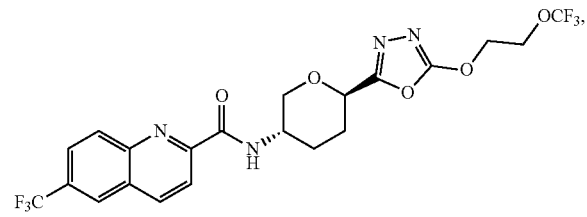
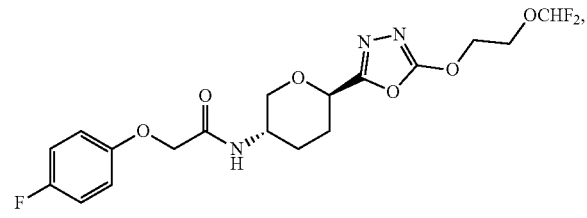
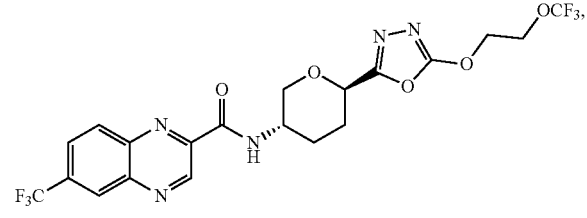
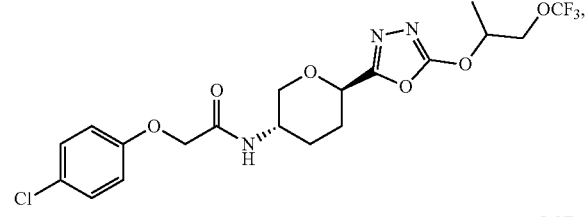
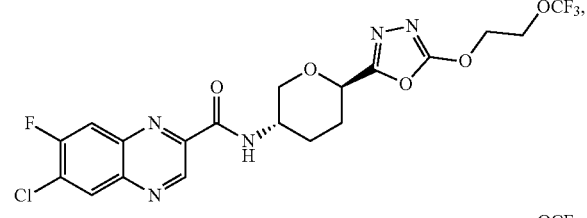
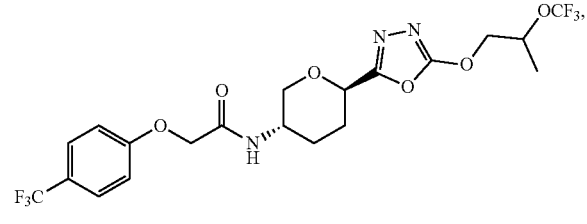
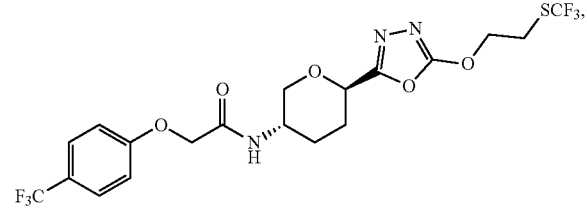

-continued
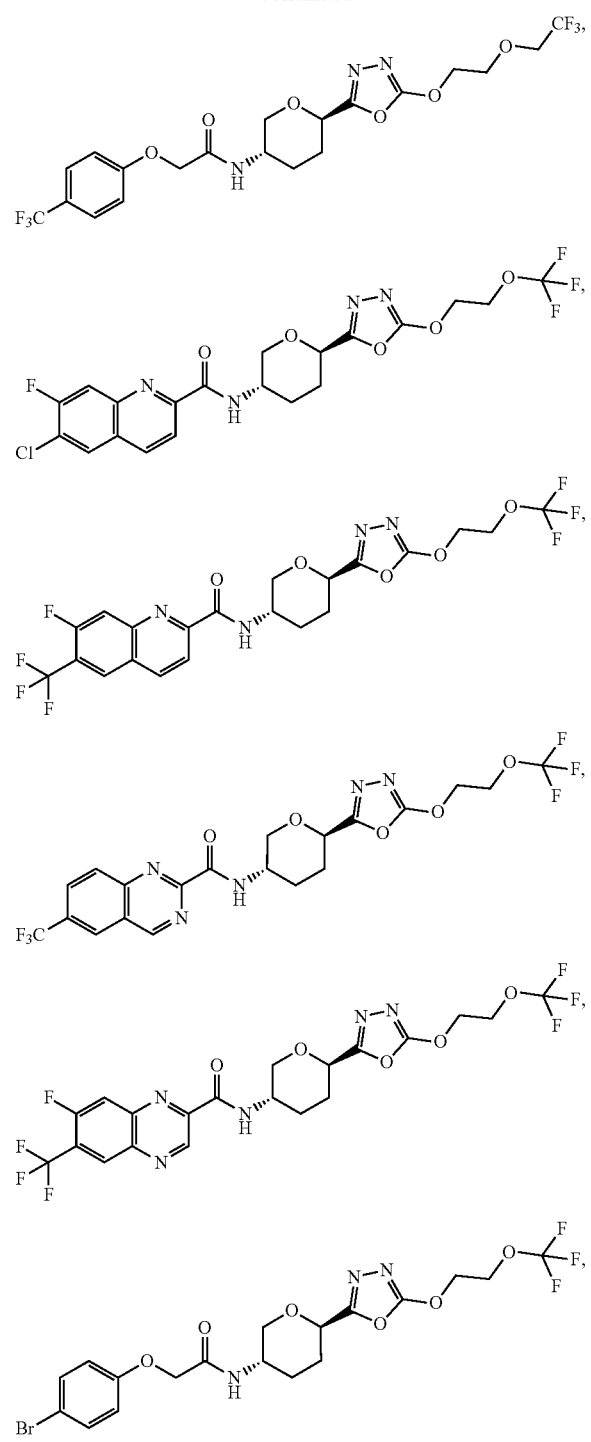
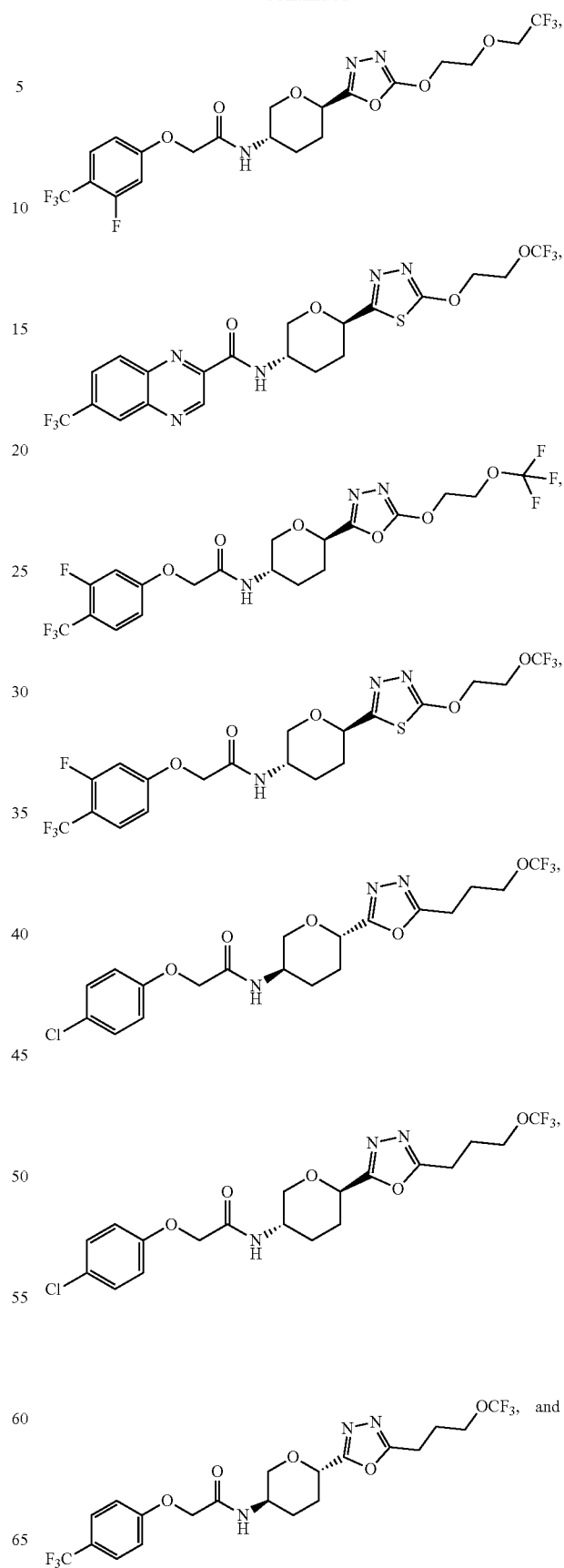

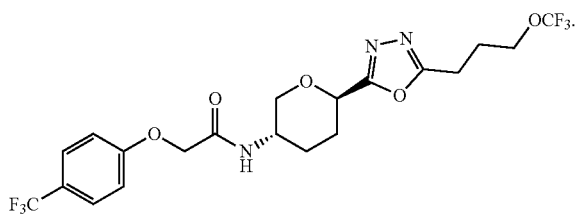

25. A pharmaceutical composition comprising a compound of claim 1, or a pharmaceutically acceptable salt, stereoisomer, mixture of stereoisomers, or prodrug thereof, and a pharmaceutically acceptable carrier.

26. A method for treating a disease or condition mediated, at least in part, by eukaryotic initiation factor 2B, the method comprising administering an effective amount of the pharmaceutical composition of claim 25 to a subject in need thereof, wherein the disease is Alexander's disease, Alper's disease, Alzheimer's disease, amyotrophic lateral sclerosis, ataxia telangiectasia, Batten disease (also known as Spielmeyer-Vogt-Sjogren-Batten disease), bovine spongiform encephalopathy (BSE), Canavan disease, Cockayne syndrome, Corticobasal degeneration, Creutzfeldt-Jakob disease, frontotemporal dementia, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), multiple sclerosis, multiple system atrophy, narcolepsy, neuroborreliosis, Parkinson's disease, Pelizaeus-Merzbacher Disease, Pick's disease, primary lateral sclerosis, prion disease, Refsum's disease, Sandhoffs disease, Schilder's disease, Subacute combined degeneration of spinal cord secondary to pernicious anemia, schizophrenia, spinocerebellar ataxia (multiple types with varying characteristics), spinal muscular atrophy, Steele-Richardson-Olszewski disease, vanishing white matter (VWM) disease, insulin resistance, or Tabes dorsalis.

27. The method of claim 26, wherein the disease is amyotrophic lateral sclerosis (ALS).

28. A compound having the structure:

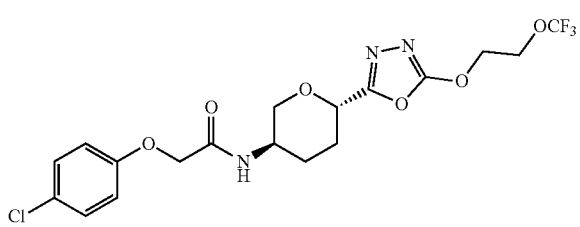 [SMILES: O=C(COc1ccc(Cl)cc1)N[C@@H]1CC[C@@H](c2nnc(OCCOC(F)(F)F)o2)OC1]

or a pharmaceutically acceptable salt thereof.

29. A pharmaceutical composition comprising a compound of claim 28, or a pharmaceutically acceptable salt thereof, and a pharmaceutically acceptable carrier.

30. A compound having the structure:

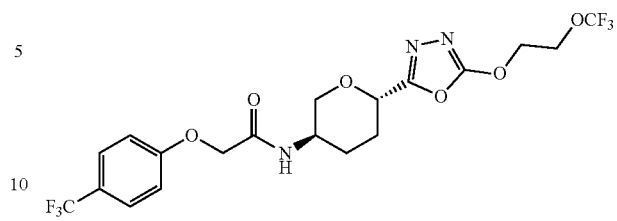

or a pharmaceutically acceptable salt thereof.

31. A pharmaceutical composition comprising a compound of claim 30, or a pharmaceutically acceptable salt thereof, and a pharmaceutically acceptable carrier.

32. A compound having the structure:

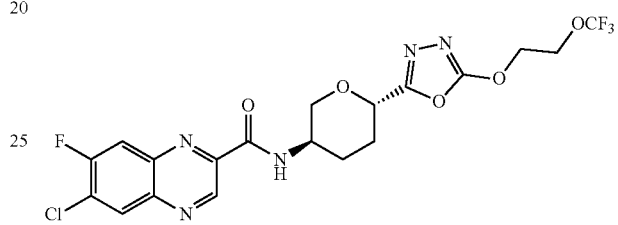

or a pharmaceutically acceptable salt thereof.

33. A pharmaceutical composition comprising a compound of claim 32, or a pharmaceutically acceptable salt thereof, and a pharmaceutically acceptable carrier.

34. A compound having the structure:

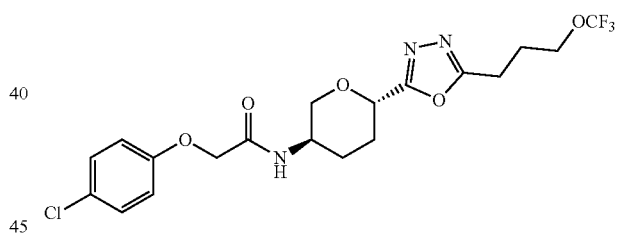

or a pharmaceutically acceptable salt thereof.

35. A pharmaceutical composition comprising a compound of claim 34, or a pharmaceutically acceptable salt thereof, and a pharmaceutically acceptable carrier.

36. A compound having the structure:

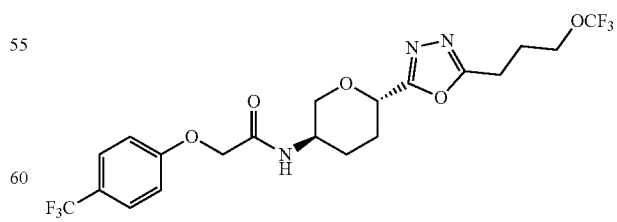

or a pharmaceutically acceptable salt thereof.

37. A pharmaceutical composition comprising a compound of claim 36, or a pharmaceutically acceptable salt thereof, and a pharmaceutically acceptable carrier.

38. A compound having the structure:

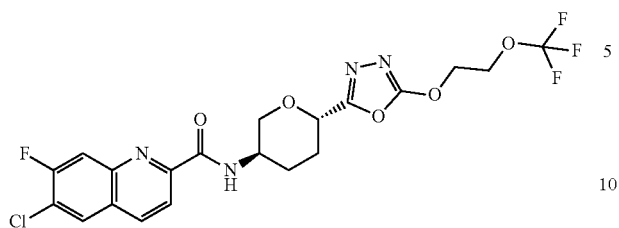

or a pharmaceutically acceptable salt thereof.

39. A pharmaceutical composition comprising a compound of claim 38, or a pharmaceutically acceptable salt thereof, and a pharmaceutically acceptable carrier.

40. A compound having the structure:

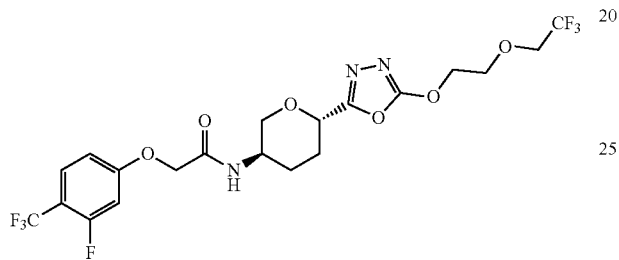

or a pharmaceutically acceptable salt thereof.

41. A pharmaceutical composition comprising a compound of claim 40, or a pharmaceutically acceptable salt thereof, and a pharmaceutically acceptable carrier.

42. A compound having the structure:

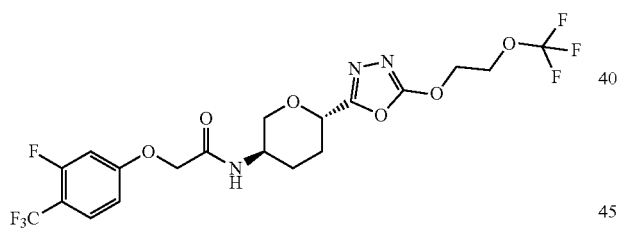

or a pharmaceutically acceptable salt thereof.

43. A pharmaceutical composition comprising a compound of claim 42, or a pharmaceutically acceptable salt thereof, and a pharmaceutically acceptable carrier.

44. A compound having the structure:

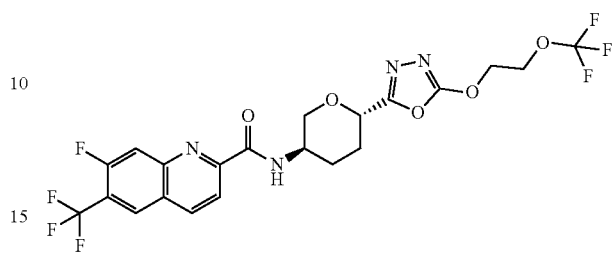

or a pharmaceutically acceptable salt thereof.

45. A pharmaceutical composition comprising a compound of claim 44, or a pharmaceutically acceptable salt thereof, and a pharmaceutically acceptable carrier.

46. A compound having the structure:

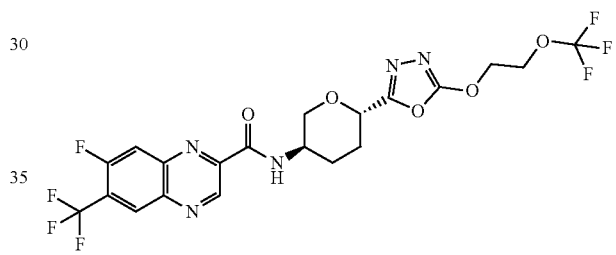

or a pharmaceutically acceptable salt thereof.

47. A pharmaceutical composition comprising a compound of claim 46, or a pharmaceutically acceptable salt thereof, and a pharmaceutically acceptable carrier.

* * * * *